US012629526B2

(12) United States Patent
Wade et al.

(10) Patent No.: US 12,629,526 B2
(45) Date of Patent: May 19, 2026

(54) PATIENT TREATMENT SYSTEMS FOR SENSING CARDIAC DEPOLARIZATION AND/OR STIMULATING THE CAROTID SINUS NERVE, AND ASSOCIATED DEVICES AND METHODS

(71) Applicant: THE ALFRED E. MANN FOUNDATION FOR SCIENTIFIC RESEARCH, Valencia, CA (US)

(72) Inventors: Molly Wade, Carver, MN (US); Mark Gryzwa, Woodbury, MN (US); Eric Lovett, Mendola Heights, MN (US); Adam W. Cates, Atlanta, GA (US)

(73) Assignee: THE ALFRED E. MANN FOUNDATION FOR SCIENTIFIC RESEARCH, Valencia, CA (US)

( * ) Notice: Subject to any disclaimer, the term of this patent is extended or adjusted under 35 U.S.C. 154(b) by 0 days.

(21) Appl. No.: 18/333,416

(22) Filed: Jun. 12, 2023

(65) Prior Publication Data

US 2023/0405329 A1     Dec. 21, 2023

Related U.S. Application Data

(60) Provisional application No. 63/496,349, filed on Apr. 14, 2023, provisional application No. 63/351,748, filed on Jun. 13, 2022.

(51) Int. Cl.
*A61N 1/36* (2006.01)
*A61N 1/05* (2006.01)
(52) U.S. Cl.
CPC ..... *A61N 1/36139* (2013.01); *A61N 1/36057* (2013.01); *A61N 1/3614* (2017.08);
(Continued)

(58) Field of Classification Search
None
See application file for complete search history.

(56) References Cited

U.S. PATENT DOCUMENTS 5,456,866 A * 10/1995 Kanome .................. G11B 7/26
                                                    425/363
6,292,703 B1     9/2001 Meier
                        (Continued)

FOREIGN PATENT DOCUMENTS

DE          19847446 B4     4/2010
JP       2008546444 A1     12/2008
                    (Continued)

OTHER PUBLICATIONS

Borst, C. et al., "Optimal frequency of carotid sinus nerve stimulation in treatment of angina pectoris." Cardiovasc Res. 1974; 8(5); 674-680.
(Continued)

*Primary Examiner* — Erica S Lee
(74) *Attorney, Agent, or Firm* — Michael J. Bolan; Vista IP Law Group, LLP

(57) ABSTRACT

Patient treatment systems and methods for sensing cardiac depolarization and/or stimulating the carotid sinus nerve are disclosed herein. Exemplary patient treatment systems can include a neuromodulator and an implantable signal delivery device electrically coupleable to the neuromodulator. The signal delivery device comprises a lead body including a first region, a second region positionable over the first region, and lead electrodes. The patient treatment system further comprises computer-readable media having instructions that cause the patient treatment system to perform operations comprising: (i) obtaining a physiological parameter of the patient, (ii) generating neuromodulation pulses based on the obtained physiological parameter, and (iii) delivering the neuromodulation pulses to the CSN afferent
(Continued)

fibers via one or more of the lead electrodes. The physiological parameter can include at least one of blood pressure, heart rate, bioimpedance, or activity level of the patient.

34 Claims, 19 Drawing Sheets

(52) U.S. Cl.
CPC ...... *A61N 1/36171* (2013.01); *A61N 1/36117* (2013.01); *A61N 1/36175* (2013.01)

(56) References Cited

U.S. PATENT DOCUMENTS

| | | | | |
|---|---|---|---|---|
| 6,456,866 | B1 * | 9/2002 | Tyler | A61N 1/0556 |
| | | | | 600/377 |
| 7,509,166 | B2 * | 3/2009 | Libbus | A61N 1/3627 |
| | | | | 607/9 |
| 8,620,422 | B2 | 12/2013 | Kieval et al. | |
| 9,272,143 | B2 | 3/2016 | Libbus et al. | |
| 9,763,586 | B2 | 9/2017 | Mokelke et al. | |
| 10,918,865 | B2 | 2/2021 | Georgakopoulos et al. | |
| 11,819,682 | B2 * | 11/2023 | Cates | A61N 1/36175 |
| 2002/0103516 | A1 | 8/2002 | Patwardhan | |
| 2006/0041277 | A1 | 2/2006 | Deem | |
| 2006/0282145 | A1 | 12/2006 | Caparso | |
| 2008/0140141 | A1 | 6/2008 | Ben-David et al. | |
| 2009/0099439 | A1 | 4/2009 | Barolat | |
| 2009/0275997 | A1 | 11/2009 | Faltys et al. | |
| 2009/0276025 | A1 | 11/2009 | Burnes et al. | |
| 2010/0228310 | A1 | 9/2010 | Shuros et al. | |
| 2011/0046432 | A1 | 2/2011 | Simon | |
| 2012/0033080 | A1 | 2/2012 | Watanabe et al. | |
| 2012/0245656 | A1 * | 9/2012 | Brockway | A61B 5/02405 |
| | | | | 607/62 |
| 2013/0131761 | A1 * | 5/2013 | Della Santina | A61N 1/36036 |
| | | | | 607/62 |
| 2013/0204328 | A1 | 8/2013 | Stahmann | |
| 2014/0257426 | A1 | 9/2014 | Arcot-Krishnamurthy | |
| 2015/0174396 | A1 * | 6/2015 | Fisher | A61N 1/3605 |
| | | | | 600/377 |
| 2015/0202444 | A1 | 7/2015 | Mandred et al. | |
| 2016/0250474 | A1 | 9/2016 | Stack et al. | |
| 2017/0173340 | A1 * | 6/2017 | Gupte | A61N 1/36114 |
| 2017/0216601 | A1 | 8/2017 | Zhou et al. | |
| 2017/0281931 | A1 * | 10/2017 | Durand | A61B 17/12 |
| 2017/0304630 | A1 | 10/2017 | Plachta et al. | |
| 2018/0056074 | A1 * | 3/2018 | Clark | A61N 1/3787 |
| 2018/0104491 | A1 | 4/2018 | Lerner | |
| 2018/0221667 | A1 * | 8/2018 | Libbus | A61N 1/37235 |
| 2020/0246623 | A1 | 8/2020 | Libbus et al. | |
| 2021/0145289 | A1 * | 5/2021 | Thakur | A61B 5/0205 |
| 2021/0178153 | A1 * | 6/2021 | Zaidi | A61N 1/0556 |
| 2021/0205621 | A1 | 7/2021 | Georgakopoulos et al. | |
| 2021/0290957 | A1 * | 9/2021 | Schulhauser | A61B 5/0205 |
| 2022/0118250 | A1 * | 4/2022 | Libbus | A61N 1/36175 |
| 2022/0134101 | A1 * | 5/2022 | Scheiner | A61N 1/3601 |
| | | | | 607/42 |
| 2022/0212006 | A1 * | 7/2022 | Rondoni | A61P 11/16 |
| 2023/0233095 | A1 | 7/2023 | Cezo | |
| 2024/0399150 | A1 | 12/2024 | Georgakopoulos et al. | |
| 2025/0161687 | A1 | 5/2025 | Wade et al. | |

FOREIGN PATENT DOCUMENTS

| | | |
|---|---|---|
| WO | 97018856 A1 | 5/1997 |
| WO | 20150108909 A1 | 7/2015 |

OTHER PUBLICATIONS

Examination Report mailed Mar. 20, 2024 in European Patent Application No. 19729887.0, 4 pages.
International Search Report and Written Opinion mailed Sep. 11, 2019 in International Patent Application No. PCT/US19/28935, 14 pages.
International Search Report and Written Opinion mailed Sep. 22, 2023 in International Patent Application No. PCT/US3/68319, 15 pages.
International Search Report and Written Opinion mailed Feb. 28, 2025 in International Patent Application No. PCT/US24/56122, 10 pages.

* cited by examiner

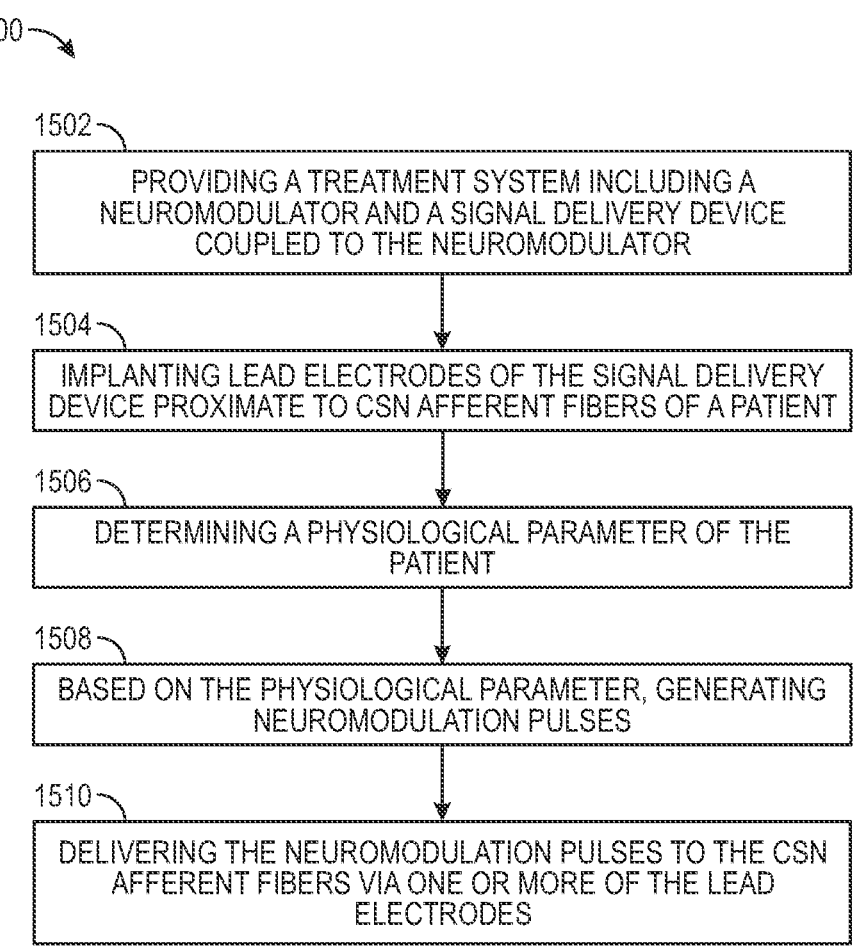

1500

1502

PROVIDING A TREATMENT SYSTEM INCLUDING A NEUROMODULATOR AND A SIGNAL DELIVERY DEVICE COUPLED TO THE NEUROMODULATOR

1504

IMPLANTING LEAD ELECTRODES OF THE SIGNAL DELIVERY DEVICE PROXIMATE TO CSN AFFERENT FIBERS OF A PATIENT

1506

DETERMINING A PHYSIOLOGICAL PARAMETER OF THE PATIENT

1508

BASED ON THE PHYSIOLOGICAL PARAMETER, GENERATING NEUROMODULATION PULSES

1510

DELIVERING THE NEUROMODULATION PULSES TO THE CSN AFFERENT FIBERS VIA ONE OR MORE OF THE LEAD ELECTRODES

1602 ⟍
PROVIDING A TREATMENT SYSTEM INCLUDING A NEUROMODULATOR AND A SIGNAL DELIVERY DEVICE COUPLED TO THE NEUROMODULATOR

1604 ⟍
IMPLANTING LEAD ELECTRODES OF THE SIGNAL DELIVERY DEVICE WITHIN A PATIENT

1606 ⟍
DELIVERING FIRST NEUROMODULATION PULSES TO NERVE FIBERS OF THE PATIENT VIA ONE OR MORE OF THE LEAD ELECTRODES ACCORDING TO FIRST STIMULATION PARAMETERS

1608 ⟍
SENSING, VIA A VECTOR OF THE TREATMENT SYSTEM, A PARAMETER ASSOCIATED WITH A CARDIAC DEPOLARIZATION EVENT

1610 ⟍
BASED ON THE SENSED PARAMETER, ADJUSTING ONE OR MORE OF THE FIRST STIMULATION PARAMETERS TO DEFINE SECOND STIMULATION PARAMETERS

1612 ⟍
DELIVERING SECOND NEUROMODULATION PULSES TO NERVE FIBERS OF THE PATIENT VIA ONE OR MORE OF THE LEAD ELECTRODES ACCORDING TO THE SECOND STIMULATION PARAMETERS

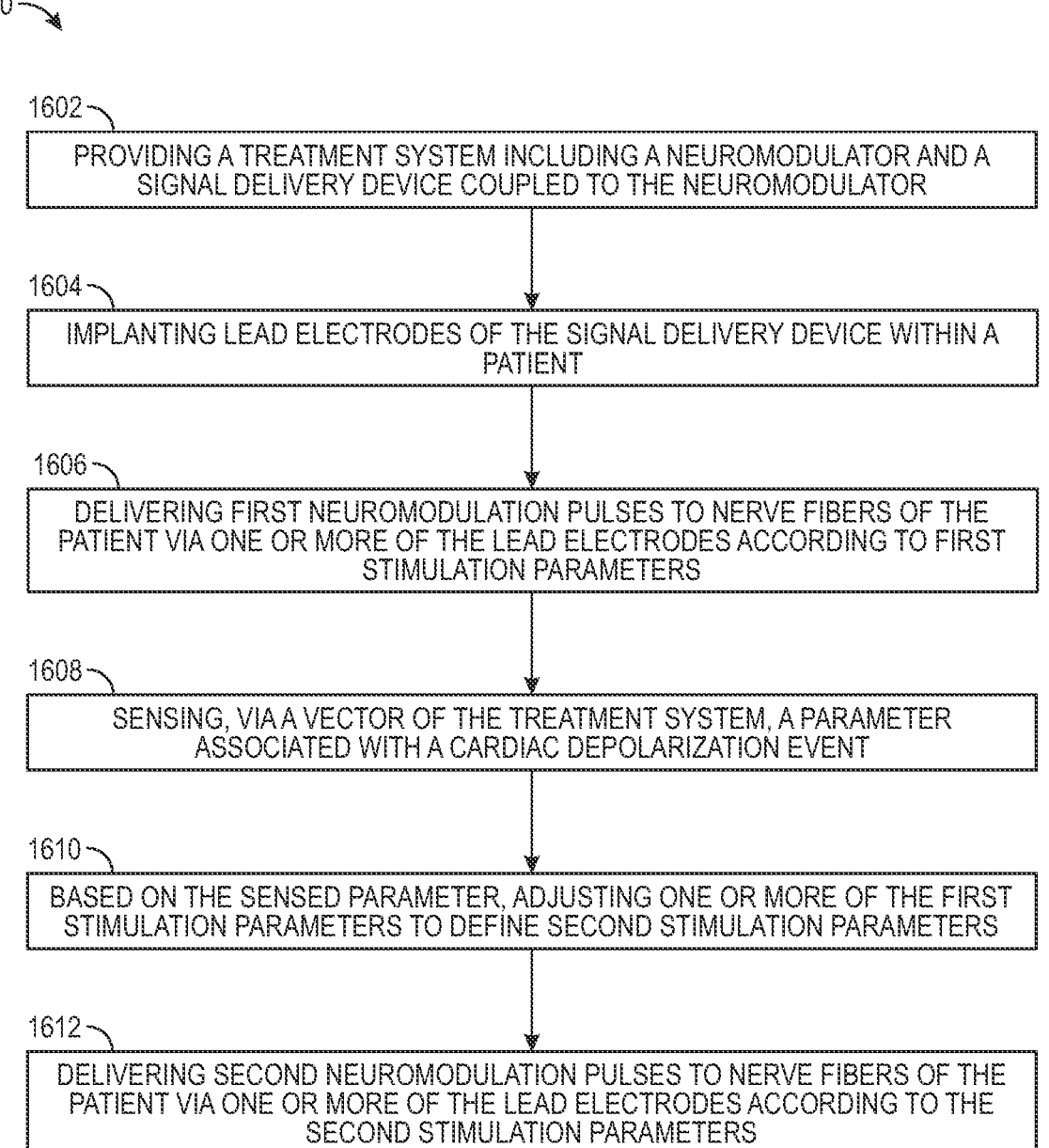

*FIG. 16*

PATIENT TREATMENT SYSTEMS FOR SENSING CARDIAC DEPOLARIZATION AND/OR STIMULATING THE CAROTID SINUS NERVE, AND ASSOCIATED DEVICES AND METHODS

CROSS-REFERENCE TO RELATED APPLICATIONS

The present application is related to U.S. patent application Ser. No. 16/393,536 (now U.S. Pat. No. 10,918,865), filed Apr. 24, 2019, and claims priority to U.S. Provisional Patent App. No. 63/351,748, filed Jun. 13, 2022, and U.S. Provisional Patent App. No. 63/496,349, filed Apr. 14, 2023, the disclosures of which are each incorporated herein by reference in their entireties.

TECHNICAL FIELD

This present disclosure relates to patient treatment systems for sensing cardiac depolarization and/or stimulating the carotid sinus nerve, and associated devices and methods.

BACKGROUND

Millions of patients worldwide suffer from cardiovascular diseases, such as hypertension (i.e., high blood pressure) and heart failure. Many different pharmaceutical and medical device treatments have been developed to treat hypertension and heart failure, but many of these treatments have been either completely ineffective or at least ineffective in large subsets of patients. For example, approximately one in ten people with high blood pressure are treatment resistant, in that pharmaceuticals do not help to reduce their blood pressure. Approximately one hundred million people worldwide suffer from treatment resistant high blood pressure, and these patients are three times more likely to suffer from a cardiovascular event, such as a heart attack, compared to patients whose blood pressure can be controlled with medications.

Several different medical devices and procedures have been tried to treat drug resistant high blood pressure. One example is a procedure in which a catheter is threaded into the arteries leading to the kidneys, and radiofrequency energy is applied to the vessel wall to denervate the small nerves surrounding the arteries. Another example is an implantable stimulator for stimulating baroreceptors in the neck by applying energy to the wall of the carotid artery. Unfortunately, these devices and procedures have not been proven to be as effective as desired. Currently, hundreds of millions of patients suffer from currently untreatable high blood pressure, which very often leads to serious cardiovascular consequences. Unfortunately, other serious health conditions, such as congestive heart failure and kidney failure, have similar stories. Therefore, a need exists for improved devices, systems, and methods for treating hypertension, heart failure. and/or other cardiovascular conditions.

BRIEF DESCRIPTION OF THE DRAWINGS

Features, aspects, and advantages of the presently disclosed technology may be better understood with regard to the following drawings.

FIG. 15 is a flow diagram of a method for stimulating a carotid sinus nerve of a patient via a patient treatment system, in accordance with embodiments of the present technology.

FIG. 16 is a flow diagram of a method for sensing cardiac depolarization of a patient via a patient treatment system, in accordance with embodiments of the present technology.

Figure 1B:
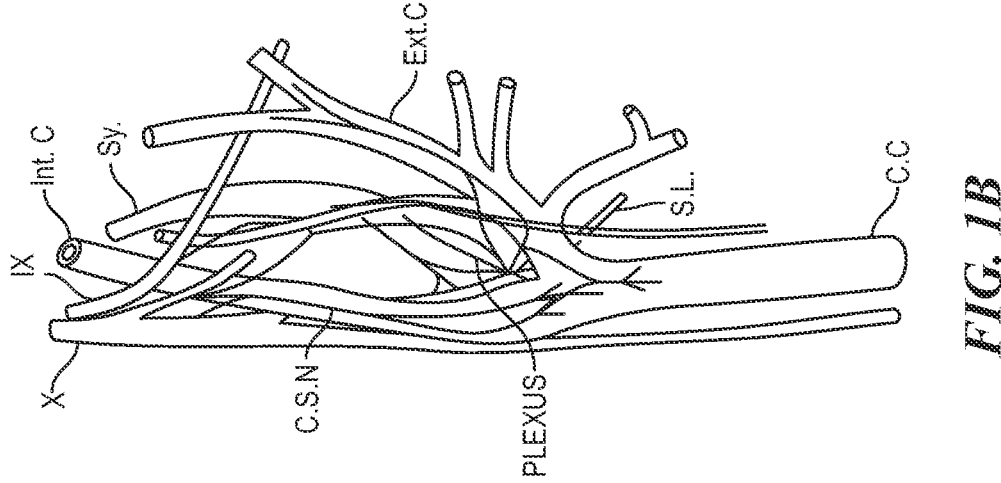
FIGS. 1A and 1B are anatomical illustrations of the carotid sinus and surrounding nerves in the anatomical area.

A person skilled in the relevant art will understand that the features shown in the drawings are for purposes of illustrations, and variations, including different and/or additional features and arrangements thereof, are possible.

DETAILED DESCRIPTION

I. Overview

Embodiments of the present disclosure relate to patient treatment systems for sensing cardiac depolarization events and/or providing non-tonic therapy to carotid sinus nerve (CSN) afferent fibers of patients based on one or more physiological parameters (e.g., heart rate, R-R wave interval, blood pressure, etc.) obtained from the patients. It is generally known that baroreceptors on the carotid sinus contain stretch receptors that respond to cardiac depolarization and the resultant pressure wave in the carotid sinus by relaying associated signals to the brain. In patients with hypertension, the mechanism for relaying such signals may be abnormal and therein limit the natural ability of the patients to regulate heart rate. Current devices that attempt to provide therapy to patients to treat hypertension via stimulation provide tonic therapy (i.e., a set frequency, amplitude, pulse width, etc.) that does not change based on patient activity, and that is provided to anatomy that has a less effective or desirable response to therapy.

Embodiments of the present disclosure address at least some of the above-described issues for patients with hypertension. For example, embodiments of the present disclosure utilize neuromodulation of the CSN to alter a patient's abnormal response and therein lower blood pressure. As disclosed herein, patient treatment systems of the present technology can map a patient's tissue by sensing cardiac depolarization and the associated electrical and/or acoustic signals, and position lead electrodes of the patient treatment system at least substantially proximate the CSN afferent fibers. Once positioned, the patient treatment system can determine one or more physiological parameters of the patient, and provide stimulation to the patient based at least in part on the one or more physiological parameters. Additionally, due in part to the ability to sense cardiac depolarization, the patient treatment system can provide neuromodulation pulses having stimulation characteristics (e.g., frequency, amplitude, pulse width, delay, etc.) that in some embodiments mimic a natural and desirable baroreceptor response (e.g., the response of patients without hypertension). In doing so, embodiments of the present technology can automatically (e.g., without user input) adjust stimulation parameters based at least in part on a patient's activity, and therein provide non-tonic therapy that is not generally diluted by a patient's activity. For these and other reasons disclosed herein, embodiments of the present technology offer patient therapy that is an improvement over existing devices and methods.

In the Figures, identical reference numbers identify generally similar, and/or identical, elements. Many of the details, dimensions, and other features shown in the Figures are merely illustrative of particular embodiments of the disclosed technology. Accordingly, other embodiments can have other details, dimensions, and features without departing from the spirit or scope of the disclosure. In addition, those of ordinary skill in the art will appreciate that further embodiments of the various disclosed technologies can be practiced without several of the details described below.

II. Anatomy of the Carotid Sinus Nerve and Vagus Nerve

Disclosed herein are methods, devices, and systems for sensing cardiac depolarization and/or stimulating nerves to treat hypertension, coronary heart disease, heart failure, kidney disease, and/or any of a number of other disease states in humans or animals. Although the following description will focus on the treatment of drug-resistant hypertension or high blood pressure, the aspects and principles described below may be used to treat, or be adapted for use to treat, several cardiovascular or other conditions. Therefore, despite the focus of the following description on one disease state, the scope of this disclosure and the methods, devices, and systems described herein are not limited to any one disease or condition.

Figure 1A:
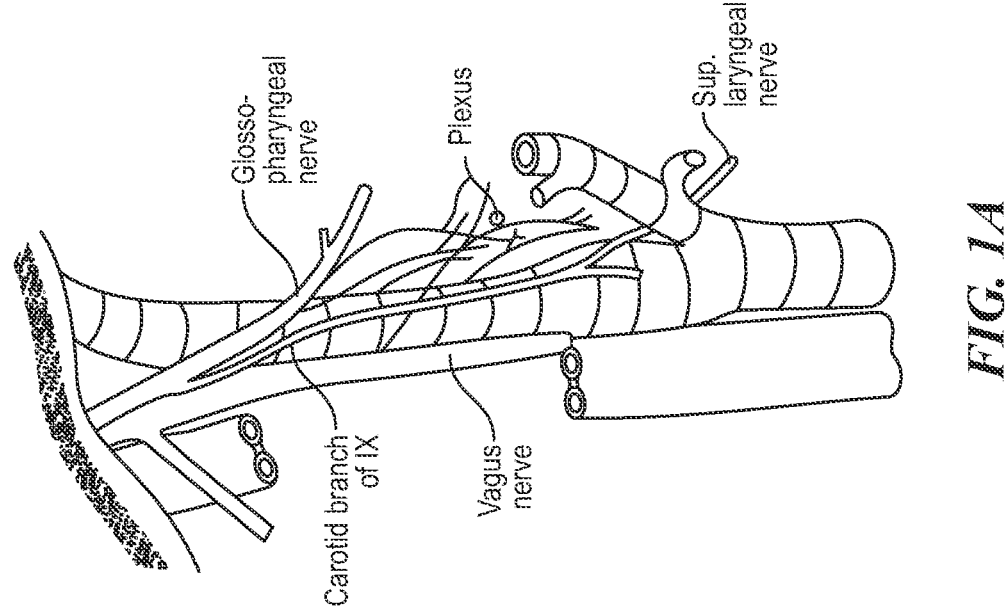
Figure 2A:
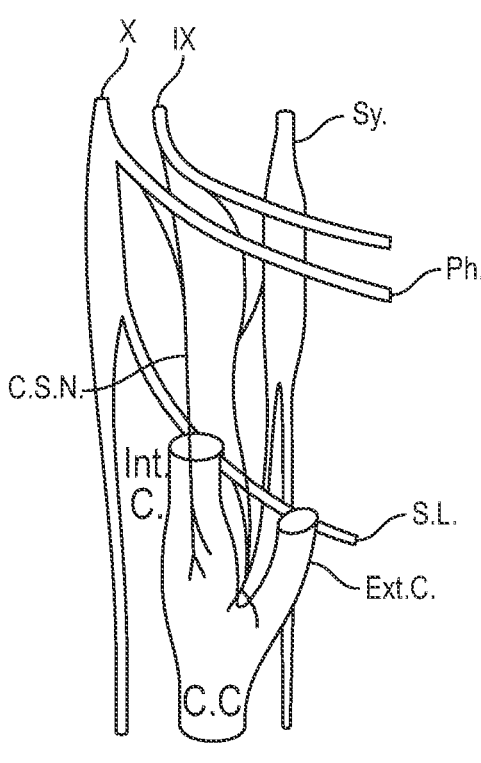
FIGS. 2A-2D are anatomical illustrations showing different patterns of a vagus nerve around the carotid sinus.
Figure 2B:
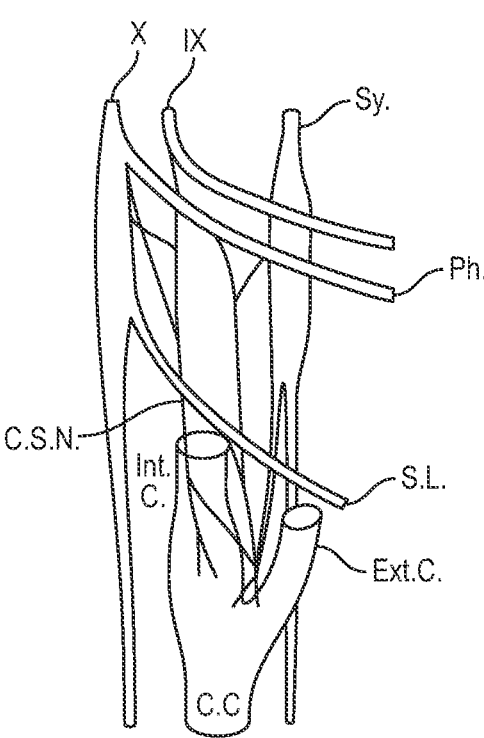
Figure 2C:
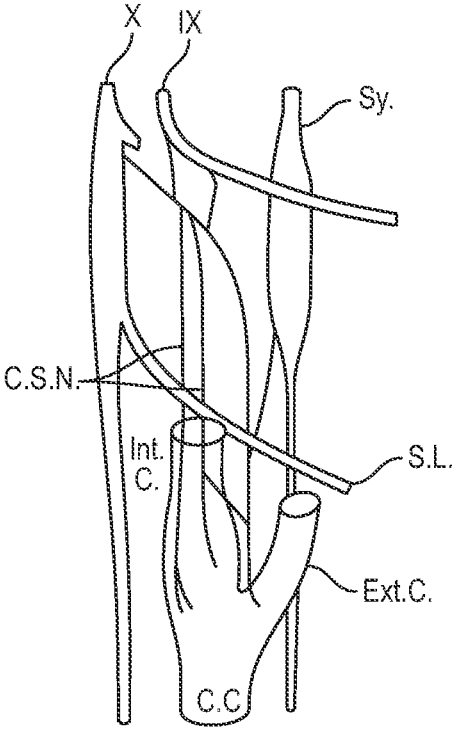
Figure 2D:
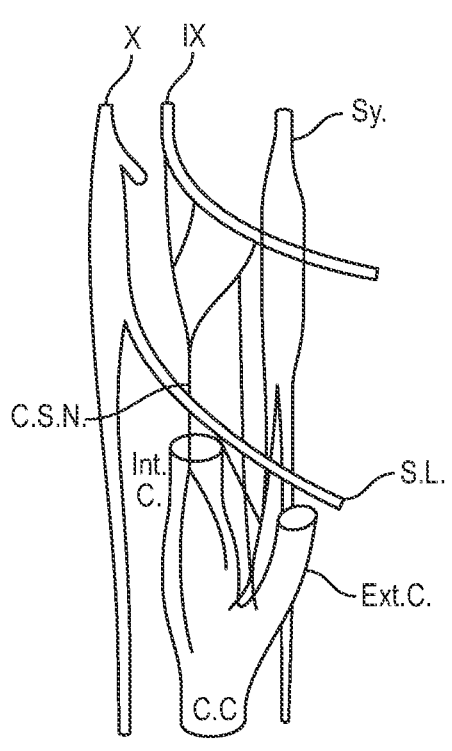

FIGS. 1A and 1B are anatomical illustrations of the carotid sinus and nerves in the surrounding anatomical area. Referring to FIGS. 1A and 1B together, there are two branches of the CSN arising from its origin in the main trunk of the glossopharyngeal nerve IX (i.e., cranial nerve IX). (The vagus nerve, or cranial nerve X, is labeled "X" in FIG. 1B.) One branch of the carotid sinus nerve courses along the anteromedial aspect of the internal carotid artery ("Int. C" in FIG. 1B), terminating in the bifurcation of the carotid sinus and plexus lying posterior and medial to the internal carotid artery in the bifurcation of the common carotid artery ("CC" in FIG. 1B). The other branch terminates in the plexus directly.

FIGS. 2A-2D are anatomical illustrations showing different patterns of the vagus nerve in the area of the carotid sinus. Referring to FIGS. 2A-2D together, in addition to CSN, the inter-carotid plexus contains afferent branches of the vagus nerve X, which are specific to the baroreflex. Four distinct patterns, illustrated in FIGS. 2A-2D, have been identified, and all contain branches of the vagus nerve X in the inter-carotid plexus.

The CSN and the vagus nerve X both include afferent nerve fibers, which carry signals to the central nervous system, and efferent nerve fibers, which carry signals away from the central nervous system. In some embodiments, the systems, devices, and methods described herein involve stimulating carotid sinus afferent nerve fibers and cardiac-specific vagal afferent nerve fibers, in order to treat hypertension and/or other suitable conditions. In some embodiments, one or both of these types of nerve fibers (i.e., carotid sinus afferent nerve fibers and/or cardiac-specific vagal afferent nerve fibers) may be identified before they are stimulated. For the purposes of this disclosure, carotid sinus afferent nerve fibers may be generally referred to as "the carotid sinus nerve," and cardiac-specific vagal afferent nerve fibers may be generally referred to as "the vagus nerve." In some embodiments, for example, electrodes of the system described herein may be placed on, over or around the carotid sinus nerve and the vagus nerve, and such electrodes may be used to stimulate carotid sinus afferent nerve fibers and/or cardiac-specific vagal afferent nerve fibers.

Figure 3:
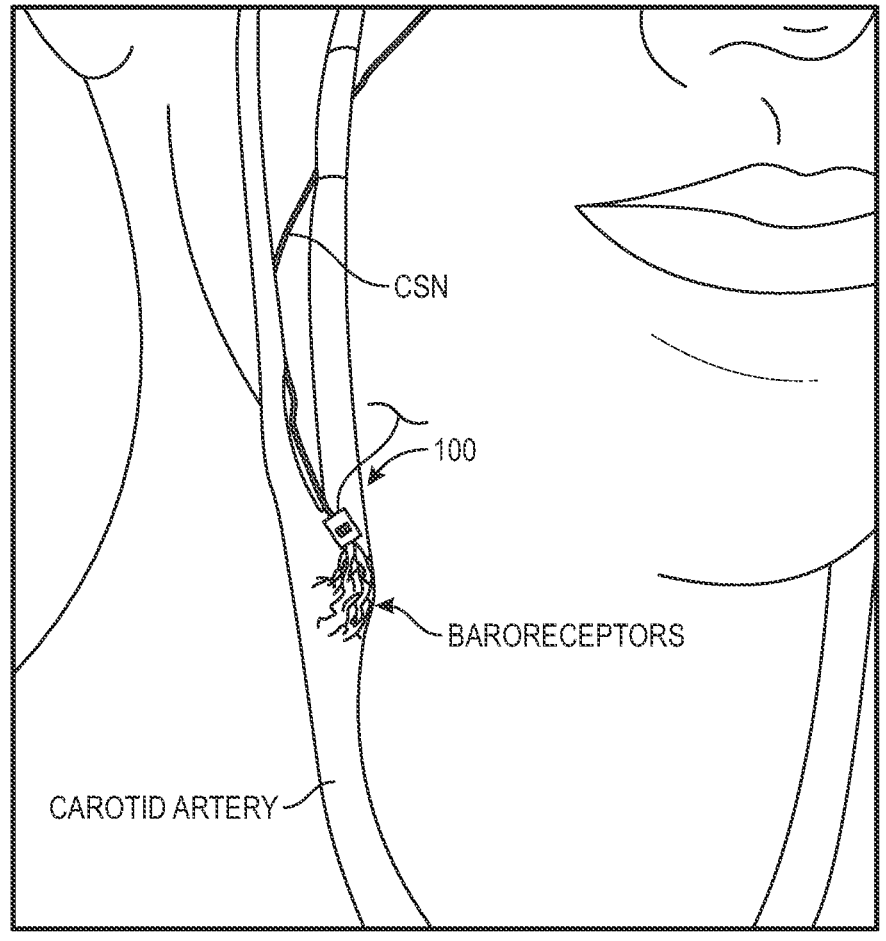
FIG. 3 is a partially schematic illustration of a patient treatment system implanted at a carotid sinus nerve of a patient, in accordance with embodiments of the present technology.

III. Sensing Cardiac Depolarization and/or Stimulating Baroreceptors, and Associated Systems, Devices, and Methods FIG. 3 is a partially schematic illustration of a patient treatment system 100 ("system 100") implanted at a CSN of a patient, in accordance with embodiments of the present technology. The system 100 can be disposed around the CSN to target some or all of the baroreceptor afferent nerve fibers within the CSN. The system 100 may be delivered subcutaneously to the area of interest and placed over the plexus of nerves that includes the CSN and the vagus nerve, as described above in reference to the anatomical drawings in FIGS. 1A-2D. As described herein, the lead body of the signal delivery device of the system 100 can include a first region having first lead electrodes, and a second region having second electrodes that is positionable over the first region. In such embodiments, the lead body can be book shaped, in that the lead body is connected along one edge and open along an opposing edge. The open edge may be turned open to partially envelop or surround one or more nerves, and then closed to hold the nerve(s). As such, the lead electrodes can span across the lead body along a first axis extending in a first direction, and the nerve(s) can extend along a second direction angled and/or normal to the first direction.

As described herein, the system 100 can sense cardiac depolarization (e.g., via electrical or acoustic signals produced therefrom), and modulate therapy based at least in part on the signals. The signals corresponding to the cardiac depolarization can be sensed via vectors formed from various combinations of the base electrodes and/or the lead electrodes of the signal delivery device, as well as other input/output devices (e.g., accelerometers or other acoustic devices) of the system 100. Additionally, sensing of the signals can be used to map the tissue of the patient, and therein aid to position the lead body of the signal delivery device in a desired location (e.g., proximate the CSN afferent fibers of the patient). Additionally, or alternatively, the tissue of the patient can be mapped by imaging the tissue, for example, using micro-Optical Coherence Tomography (OCT) imaging, ultrasound, and/or other suitable imaging techniques. The target neural fibers of the patient can be identified in the image(s) and used to aid in positioning the lead body at the desired location. In these and/or other embodiments, one or more patient tissues can be mapped by applying a stimulus (e.g., an electrical stimulus, via a temporary or chronic stimulator) and observing the patient's response (e.g., motor response) to the applied stimulus. The system 100 can determine one or more physiological parameters of the patient and, once the lead body is in the desired position, modulate therapy to be delivered to the patient based at least in part on the physiological parameters. Therapy delivery to the patient, or more particularly to the CSN afferent fibers, can be provided via one or more of the lead electrodes. In some embodiments, the system 100 includes one or more sensors configured to detect muscle fasciculation and the therapy can be modulated based, at least in part, on one or more muscle fasciculations detected by the one or more sensors.

Figure 4A:
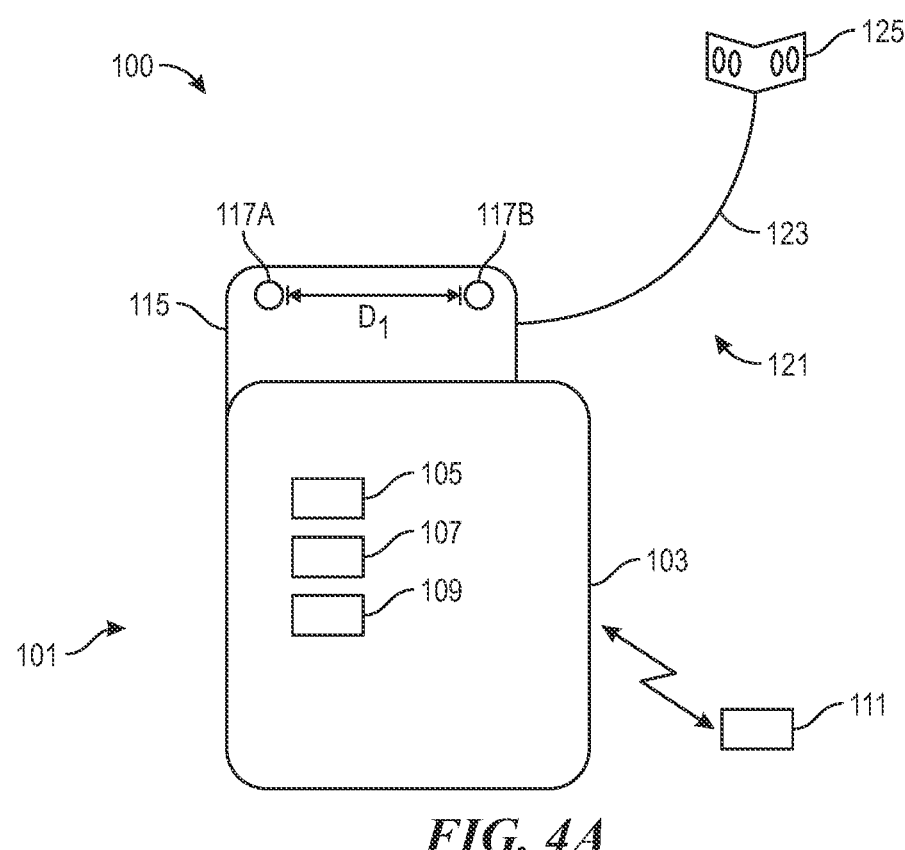
FIGS. 4A and 4B are partially schematic illustrations of various embodiments of a patient treatment system, in accordance with embodiments of the present technology.
Figure 4B:
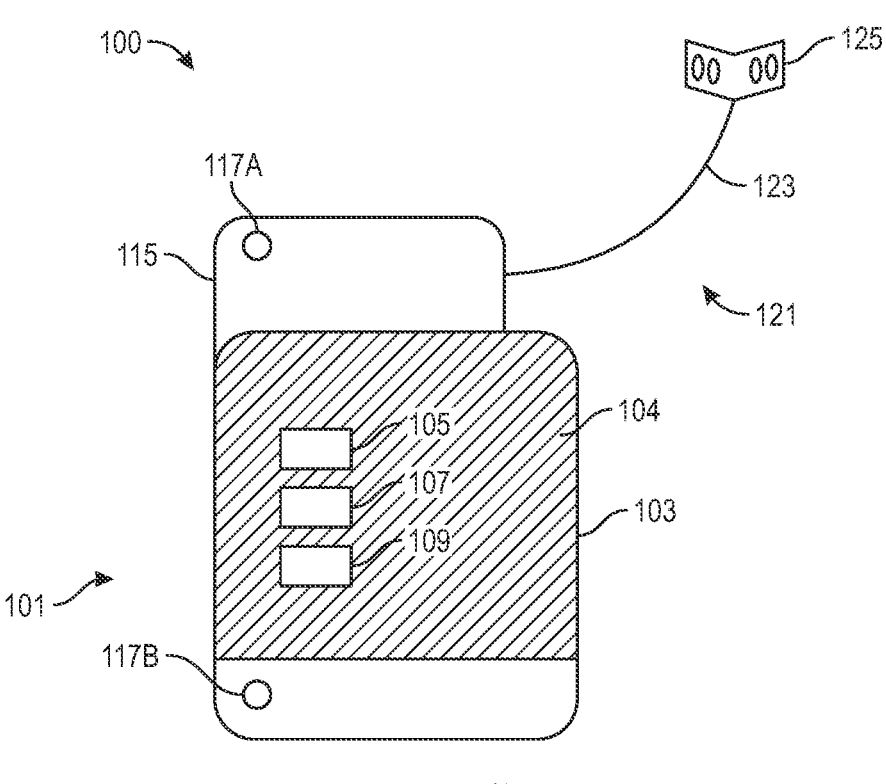

FIGS. 4A and 4B are partially schematic illustrations of various embodiments of the system 100 shown in FIG. 3, in accordance with embodiments of the present technology. Referring to FIGS. 4A and 4B together, the system 100 includes an implantable neuromodulator 101 (e.g., a signal generator or implanted pulse generator ("IPG")) and one or more signal delivery elements or devices 121 ("signal delivery device 121") electrically coupleable to the neuromodulator 101. The signal delivery device 121 can be implanted within a patient and carry features for delivering therapy to the patient after implantation. The neuromodulator 101 can be connected directly to the signal delivery device 121, or it can be connected to the signal delivery device 121 via a signal link or lead extension. As explained herein (e.g., with reference to FIGS. 5A-7B), the signal delivery device 121 can include a lead body 125 having one or more lead electrodes, and one or more conductors 123 extending from and electrically coupling the lead electrodes to the neuromodulator 101. As used herein, the terms signal delivery device, lead, and/or lead body include any of a number of suitable substrates and/or support members that carry electrodes/devices for providing therapy signals to a patient. For example, the lead body 125 can include one or more electrodes or electrical contacts that direct electrical signals into the patient's tissue or fibers (e.g., to treat hypertension). In other embodiments, the signal delivery device 121 can include structures other than a lead body that also direct electrical signals and/or other types of signals to the patient.

The neuromodulator 101 can include a housing 103 made from a conductive material (e.g., titanium or other metal), and one or more base electrodes (e.g., contacts) 117A, 117B carried by the housing 103 and spaced apart from one another (e.g., to create a sufficient vector). The base electrodes 117A, 117B can serve as an anode/cathode pair, and can each be electrically coupled to each of the lead electrodes of the lead body 125 via the conductors 123. In some embodiments, the base electrodes 117A, 117B can be contacts that are an exposed conductive portion of the housing 103. As shown in FIG. 4A, the base electrodes 117A, 117B are included on a header portion 115 of the neuromodulator 101 and spaced apart from one another by a minimum distance ($D_1$), which can be at least 1.0 inch, 1.5 inches, or 2 inches. As shown in FIG. 4B, the neuromodulator 101 can include an insulative or non-conductive material 104. In such embodiments, the base electrodes 117A, 117B can be spaced apart from one another along a height of the neuromodulator 101, for example, with one of the base electrodes 117A on the header portion 115 and the other of the base electrodes 117B on another portion of the neuromodulator not covered by the insulative material 104.

Referring again to FIGS. 4A and 4B together, the neuromodulator 101 can transmit signals (e.g., electrical signals, neuromodulation pulses, etc.) to the signal delivery device 121 that up-regulate (e.g., excite) and/or down-regulate (e.g., block or suppress) target nerves. As used herein, and unless otherwise noted, the terms "modulate," "modulation," "stimulate," and "stimulation" refer generally to signals that have either type of the foregoing effects on the target nerves. The neuromodulator 101 can include a machine-readable (e.g., computer-readable) medium containing instructions for generating and transmitting suitable therapy signals. The neuromodulator 101 and/or other elements of the system 100 can include one or more processor(s) 105, memory unit(s) 107, and/or input/output device(s) 109 ("I/O devices 109"). Accordingly, the process of providing modulation signals, providing guidance information for positioning the signal delivery device 121 (e.g., relative to target fibers of the patient), and/or executing other associated functions can be performed by computer-executable instructions contained by, on, or in computer-readable media located at the neuromodulator 101 and/or other system components. The neuromodulator 101 and/or other system components may include dedicated hardware, firmware, and/or software for executing computer-executable instructions that, when executed, perform any one or more methods, processes, and/or sub-processes described herein (e.g., the methods, processes, and/or sub-processes described herein). Said dedicated hardware, firmware, and/or software also serve as "means for" performing the methods, processes, and/or sub-processes described herein. The neuromodulator 101 can also include multiple portions, elements, and/or subsystems (e.g., for directing signals in accordance with multiple signal delivery parameters), carried in a single housing, as shown in FIGS. 4A and 4B, or in multiple housings. In some embodiments, the system 100 can include an external device (e.g., a controller or physician's programmer) 111 able to control and carry out therapy provided via the system 100.

The neuromodulator 101 can also receive and respond to an input signal received from one or more sources. The input signals can direct or influence the manner in which the therapy and/or process instructions are selected, executed, updated, and/or otherwise performed. The input signals can be received from one or more sensors (e.g., the I/O devices 109) that are carried by the neuromodulator 101 and/or distributed outside the neuromodulator 101 (e.g., at other patient locations) while still communicating with the neuromodulator 101. The sensors and/or other I/O devices 109 can provide inputs that depend on or reflect patient state (e.g., patient position, patient posture, patient heart rate, patient blood pressure, and/or patient activity level), and/or inputs that are patient-independent (e.g., time).

In some embodiments, the I/O devices 109 can include an accelerometer (e.g., a multi-axial accelerometer or tri-axial accelerometer). In such embodiments, the accelerometer can be used to sense or obtain acoustic signals generated from and/or associated with cardiac depolarization. The acoustic signals can be utilized additionally or alternatively to the electrical signals generated from and/or associated with cardiac depolarization that are sensed at least via the base electrodes 117A, 117B of the neuromodulator 101 and/or the lead electrodes of the lead body 125. Additionally, or alternatively to determining the acoustic signals generated from and/or associated with cardiac depolarization, the accelerometer can be configured to detect acoustic signals associated with airflow, for example, to measure the patient's respiratory rate and/or other respiratory related information (e.g., detecting apneas, hypopneas, snoring, etc.). In these and/or other embodiments, the accelerometer can be used to determine patient position and/or orientation relative to a gravitational field, including whether the patient is standing, sitting, laying down (e.g., sleeping), etc. In such embodiments, the accelerometer can serve, for example, as a fall detector or safety mechanism, and the signal from the accelerometer can be used to adjust stimulation or characteristics of the neuromodulation pulses. In some embodiments, the I/O devices 109 can include a tonometer for determining arterial stiffness, or other devices for determining an augmentation pressure waveform or index. As described herein, arterial stiffness and/or the augmentation pressure waveform or index can be used as a physiological parameter that in part affects the characteristics of the neuromodulation pulses provided to the patient via the signal delivery device 121.

In some embodiments, data from the accelerometer can be used to detect whether the patient is asleep and/or the patient's actual or expected sleep state (e.g., REM, non-REM, etc.). For example, changes (or a lack thereof) to the physical orientation and/or movement of the accelerometer can indicate when the patient has been supine or otherwise immobile for extended periods of time which, in turn, can indicate that the patient is asleep. In some embodiments, the data from the accelerometer (e.g., one or more acoustic signals, patient position, patient orientation, etc.) can be compared with data from one or more other sensors (e.g., heart rate sensors) to detect whether the patient is asleep and/or the patient's actual or expected sleep state. These and/or other data associated with whether the patient is asleep and/or the patient's sleep states can be used to adjust the neuromodulation pulses delivered to the patient. For example, an intensity of the neuromodulation pulses can be reduced during non-REM sleep to conserve energy, for example, because the patient's sympathetic nervous system activity is expected to be lower or at a minimum during these times.

In some embodiments, the I/O devices 109 can be configured to detect and/or receive an input from the patient corresponding to an activity or state of the patient. For example, the I/O devices 109 can include a software application configured to allow the user to select one or more profiles associated with the patient's physical, mental, and/or emotional state. These can include, for example, participating in structured exercise (e.g., cardio, such as jogging, elliptical, walking, biking, swimming, etc.; strength training, such as weightlifting; isometric exercise, such as yoga; sit-ups; push-ups; etc.), inactive wakefulness, sleep, anxious or stressed, meal-time and/or post-prandial, bearing down (e.g., bowel movement), intercourse, etc. These and/or other physiological parameters can be used to adjust the neuromodulation pulses delivered to the patient.

In some embodiments, the neuromodulator 101 and/or signal delivery device 121 can obtain power to generate the therapy signals from an external power source (not shown). In some embodiments, the external power source can transmit power to the implanted neuromodulator 101 and/or directly to the signal delivery device 121 using electromagnetic induction (e.g., RF signals). For example, the external power source can include an external coil that communicates with a corresponding internal coil within the implantable neuromodulator 101, signal delivery device 121, and/or a power relay component. The external power source can be portable for ease of use.

FIGS. 5A-11 are partially schematic illustrations of various embodiments of lead bodies 525, 625, 725, 825, 925, 1025, 1125 of respective signal delivery devices 521, 621, 721, 821, 921, 1021, 1121 configured in accordance with embodiments of the present technology. FIGS. 5A, 6A, 7A, 8A, 9, 10, 11A, and 11B illustrate plane views of the lead bodies 525, 625, 725, 825, 925, 1025, 1125 in an open configuration, and FIGS. 5B, 6B, 7B, and 8B illustrate cross-sectional views of the lead bodies 525, 625, 725, 825 in a closed configuration. The signal delivery devices 521, 621, 721, 821, 921, 1021, 1121 shown and described with reference to FIGS. 5A-11E can include any one or more of the features of and be generally similar to the signal delivery device 121 of FIGS. 4A and/or 4B. Additionally, the signal delivery device 121 can include any one or more of the features of the signal delivery devices 521, 621, 721, 821, 921, 1021, 1121 described herein.

Figure 5A:
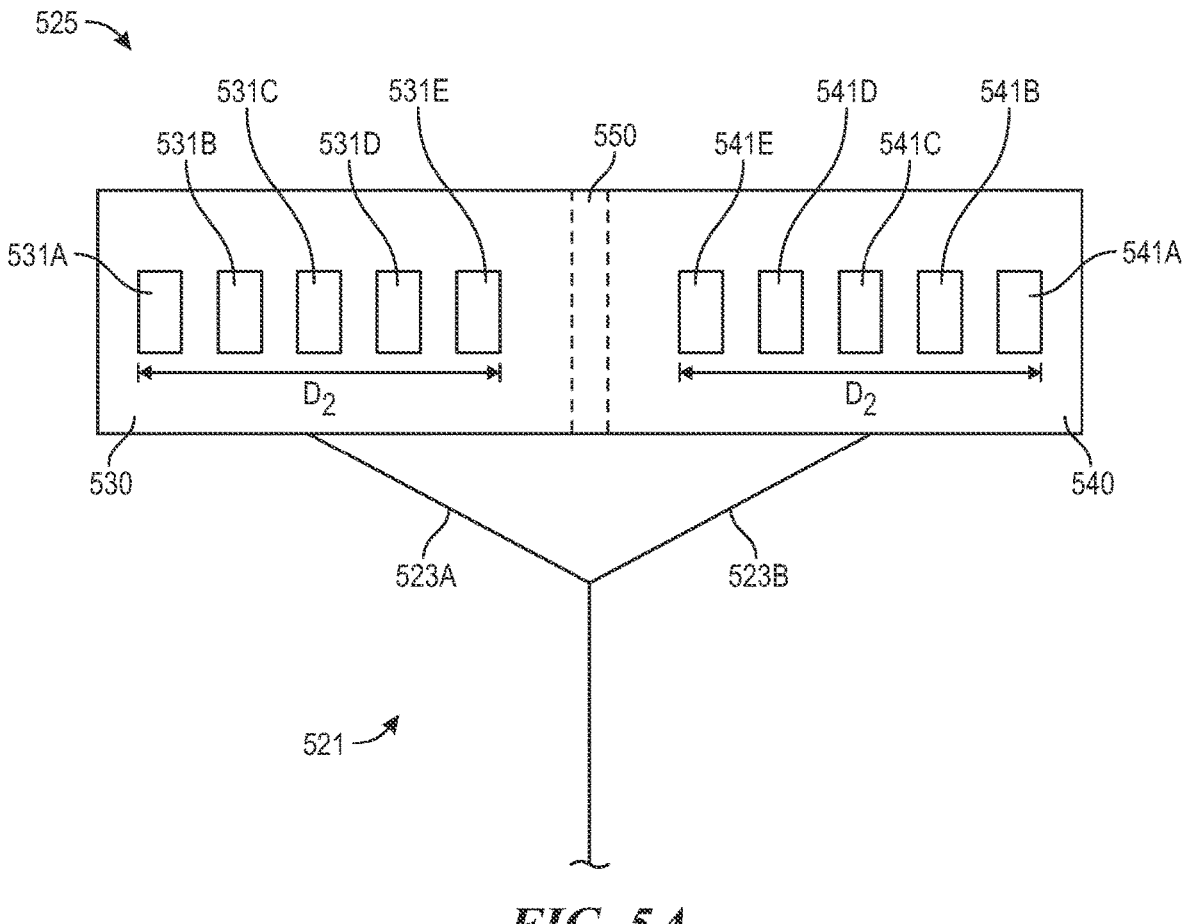
FIG. 5A-11E are partially schematic illustrations of various embodiments of signal delivery devices, configured in accordance with embodiments of the present technology.

As shown in FIG. 5A, the signal delivery device 521 includes a lead body 525 including a first region 530 (e.g., a first plate, first face, first substrate, etc.), a second region 540 (e.g., a second plate, second face, second substrate, etc.), an intermediate region 550 between the first region 530 and the second region 540, and lead electrodes. One or both of the first region 530 and the second region 540 can include one or more grip tabs, rounded edges, and/or other features to facilitate implantation. The lead electrodes can be positioned on one or more sides (e.g., a front side, a back side, etc.) of the lead body 525, and can include a first set of lead electrodes 531A-531E (collectively referred to as "the first lead electrodes 531") on the first region 530, and a second set of lead electrodes 541A-541E (collectively referred to as "the second lead electrodes 541") on the second region 540. The first lead electrodes 531 can be aligned on the first region 530 in a direction at least generally perpendicular to the intermediate region 550 (e.g., as shown in FIG. 5A) or in a direction at least generally parallel to the intermediate region 550 (e.g., as shown in FIG. 5C). Similarly, the second lead electrodes 541 can be aligned on the second region 540 in a direction at least generally perpendicular to the intermediate region 550 (e.g., as shown in FIG. 5A) or in a direction at least generally parallel to the intermediate region 550 (e.g., as shown in FIG. 5C). Returning to FIG. 5A, individual ones of the first lead electrodes 531 and/or the second lead electrodes 541 can have a length and/or a width of up to 5 mm, such as up to 4 mm, up to 3 mm, up to 2 mm, up to 1 mm, up to 0.5 mm, etc. In at least some embodiments, for example, one or more of the first lead electrodes 531 and/or one or more of the second lead electrodes 541 have a length of 2 mm and a width of 0.8 mm. Although the first and second lead electrodes 531, 541 have a rectangular shape in the embodiment illustrated in FIG. 5A, in other embodiments, individual ones of the first and/or second lead electrodes 531, 541 can have a circular, oval, square, pentagonal, hexagonal, ring, "X," zig-zag, and/or other suitable shape. Each of the first lead electrodes 531 and the second lead electrodes 541 can be a positively charged electrode or a negatively charged electrode. In some embodiments, the first lead electrodes 531 and the second lead electrodes 541 can include alternatively charged electrodes. For example, the primary first lead electrode 531A can be positively charged, the secondary first lead electrode 531B can be negatively charged, the tertiary first lead electrode 531C can be positively charged, and so on and so forth. In some embodiments, all the first lead electrodes 531 are positively charged electrodes and all of the second lead electrodes 541 are negatively charged electrodes (or vice versa). The first lead electrodes 531 and the second lead electrodes 541 can each span the same distance (D$_2$) of the respective first region 530 and second region 540. The first region 530 can be positioned over the second region 540, for example, by folding the first region 530 over the second region 540 (or vice versa) about the intermediate region 550. Individual pairs of the first and/or second lead electrodes 531, 541 can be referenced against one or more other pairs of the first and/or second lead electrodes 531, 541 (e.g., to determine a relative impedance, therapy delivery efficacy, to map the patient's tissue, etc.).

The signal delivery device 521 can further include conductors extending from the lead electrodes to the neuromodulator 101 (FIGS. 4A and 4B). The conductors can include first conductors 523A and second conductors 523B (collectively referred to as "the conductors 523"), each of which are shown schematically in FIG. 5A as a single line. Individual ones of the first conductors 523A can be electrically coupled to one of the first lead electrodes 531. For example, a primary first conductor can be electrically coupled to the primary first lead electrode 531A, a secondary first conductor can be electrically coupled to the secondary first lead electrode 531B, and so on and so forth. Similarly, individual ones of the second conductors 523B can be electrically coupled to one of the second lead electrodes 541. For example, a primary second conductor can be electrically coupled to the primary second lead electrode 541A, a secondary second conductor can be electrically coupled to the secondary second lead electrode 541B, and so on and so forth. Each of the conductors 523 is electrically coupled to (i) at least one of the first lead electrodes 531 or the second lead electrodes 541, and (ii) at least one of the base electrodes 117 (FIG. 4A or 4B) of the neuromodulator 101. As such, in some embodiments, each of the lead electrodes can be individually selected and/or addressable via a conductive pathway including either of the base electrodes 117.

Figure 5B:
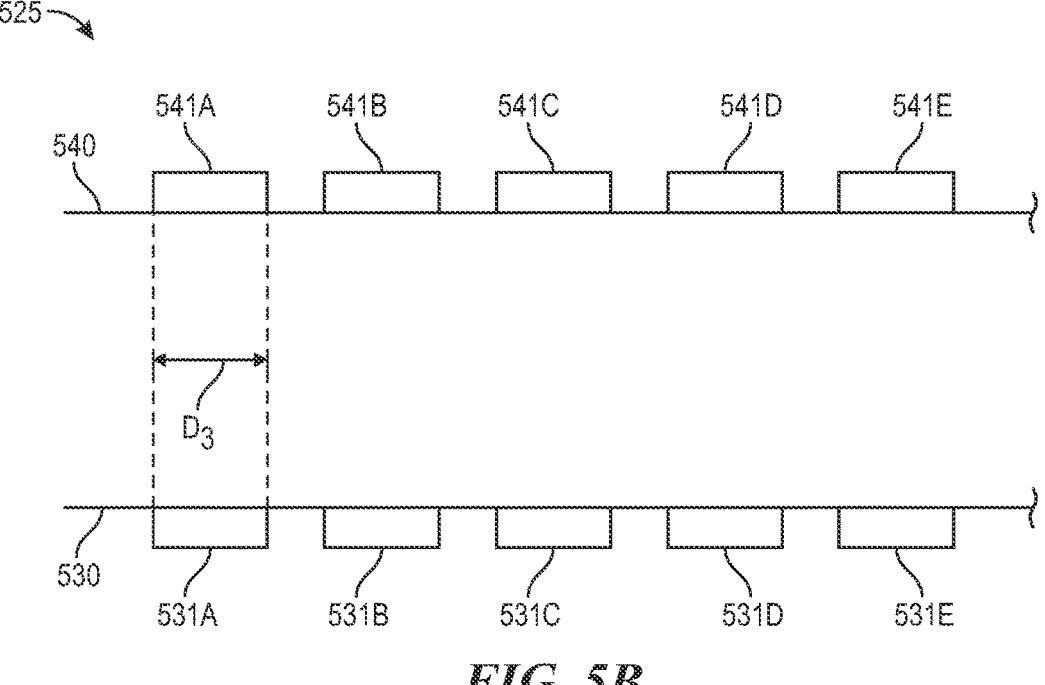
Figure 5C:
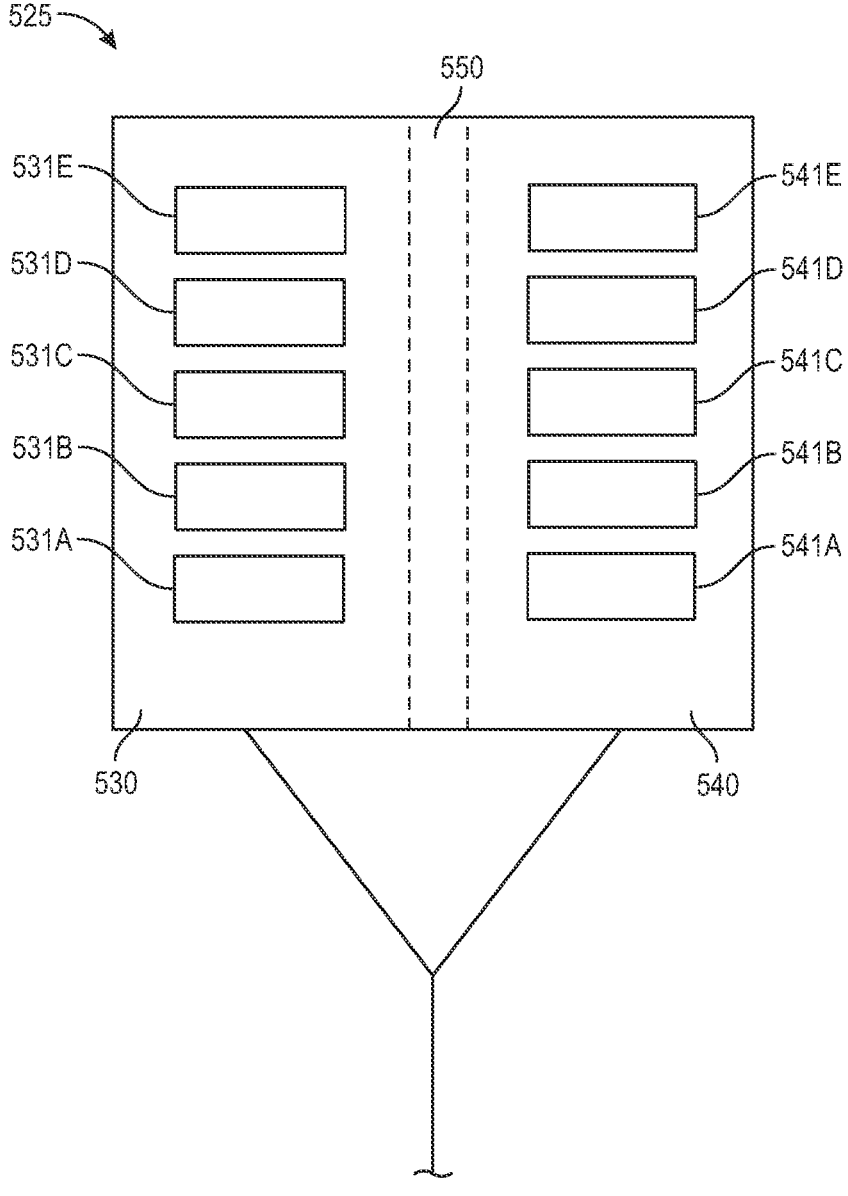

As shown in FIG. 5B, the second region 540 is positioned over the first region 530 and, in such a configuration, individual first lead electrodes 531 are positioned over or at least partially over (e.g., at least partially aligned with and/or overlapping) corresponding individual second lead electrodes 541. For example, when the first region 530 is positioned over the second region 540, the primary first lead electrode 531A is positioned over the primary second lead electrode 541A, the secondary first lead electrode 531B is positioned over the secondary second lead electrode 541B, and so on and so forth. In some embodiments, the individual first lead electrodes 531 and the individual second lead electrodes 541 can span the same distance ($D_3$) of the corresponding first region 530 or second region 540 and/or overlap completely with one another. In other embodiments, one or more of the individual first lead electrodes 531 can span a different distance of the corresponding first region 530 or second region 540 and/or be offset relative to one another.

In operation, the signal delivery device 521 (and, more particularly, the lead body 525) can be positioned around a target area or nerve(s) (e.g., afferent nerve fibers) at the CSN. For example, the first region 530 and/or first lead electrodes 531 can be on a first side of the target nerve(s) and the second region and/or second lead electrodes 541 can be on a second, opposing side of the target nerve(s). The signal delivery device 521 can deliver neuromodulation pulses to the target nerve(s) via one or more of the lead electrodes, for example, as monopolar stimulation or multi-polar stimulation (e.g., bipolar stimulation, tripolar stimulation, etc.). For example, neuromodulation pulses can be delivered as monopolar stimulation via one of the first lead electrodes 531 or one of the second lead electrodes 541, or as bipolar stimulation via a combination of the first and second lead electrodes 531, 541 (e.g., the primary first lead electrode 531A and the primary second lead electrode 541A). Additionally, or alternatively, the first lead electrodes 531 and/or second lead electrodes 541 can be positively biased (+) or negatively biased (−) and have a number of arrangements.

For example, adjacent electrodes can have arrangements including +−−+, +−+, −++−, −+−, +−−−+, −+++−, or +−, amongst other possibilities, and opposing electrodes (e.g., when the second region 540 is positioned over the first region 530) can be complementary biased. Advantageously, the arrangement of the first lead electrodes 531 relative to the second lead electrodes 541 can decrease the energy needed to deliver stimulation to the target nerve. Stated differently, by arranging individual lead electrodes on the first region 530 and the second region 540 that are opposed to one another and on opposing sides of the target nerve, embodiments of the present technology can enable bipolar stimulation to be delivered that targets particular nerves, while also minimizing the amount of energy required to do so.

Figure 5D:
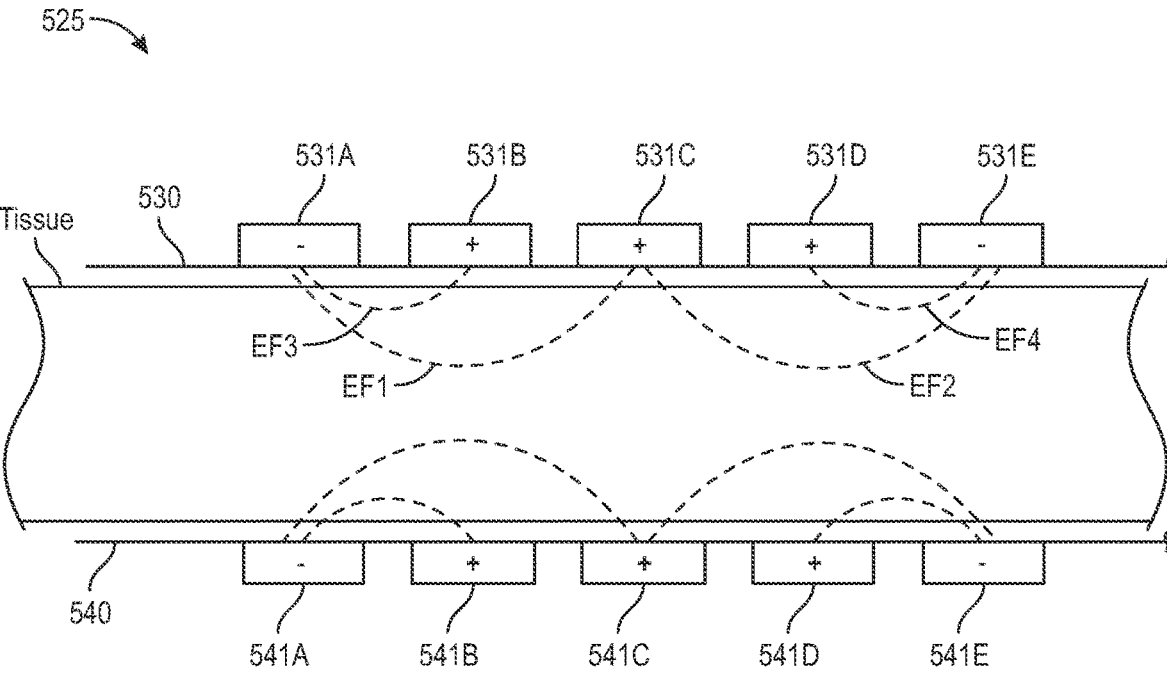

As shown in FIG. 5D, in some embodiments, the intermediate first and second lead electrodes 531, 541 can have one polarity and the peripheral first and second lead electrodes 531, 541 can have an opposite polarity. For example, in FIG. 5D the secondary, tertiary, and quaternary first lead electrodes 531B-D (i.e., the intermediate electrodes) are cathodes and the primary and quinary first lead electrodes 531A, 531E (i.e., the peripheral electrodes) are anodes. In such embodiments, the secondary and quaternary lead electrodes 531B, 531D can be configured to act as guard cathodes, for example, to cause first and second electrical fields EF1, EF2 generated between the tertiary first lead electrode 531C and the primary and quinary first lead electrodes 531A, 531E to extend deeper into tissue of the patient. For example, the secondary first lead electrode 531B and the primary first lead electrode 531A can cooperate to generate a third electrical field EF3. The first electrical field EF1 between the tertiary first lead electrode 531C and the primary first lead electrode 531A can extend deeper into patient tissue to avoid or evade the third electrical field EF3. Similarly, the quaternary lead electrode 531D and the quinary first lead electrode 531E can cooperate to generate a fourth electrical field EF4. The second electrical field EF2 between the tertiary first lead electrode 531C and the quinary first lead electrode 531E can extend deeper into patient tissue to avoid or evade the fourth electrical field EF2. In some embodiments, the depth of the first and second electrical fields EF1, EF2 can be enhanced by varying the size of individual ones of the first lead electrodes 531. For example, the secondary and quaternary first lead electrodes 531B, 531D can be smaller (e.g., have a smaller perimeter and/or less surface area) than the primary, tertiary, and/or quinary first lead electrodes 531A, C, D. Each of the second lead electrodes 541 can be configured to be generally similar or the same as the corresponding one of the first lead electrodes 531.

Figure 6A:
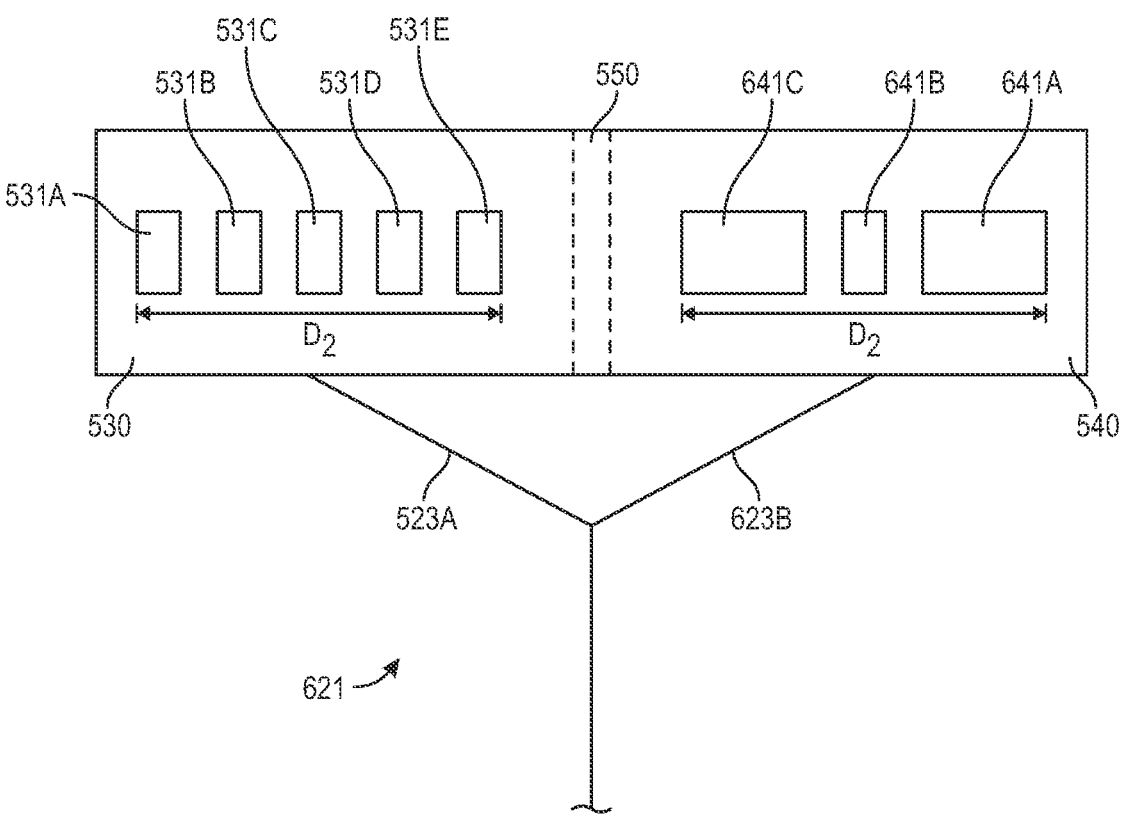
Figure 6B:
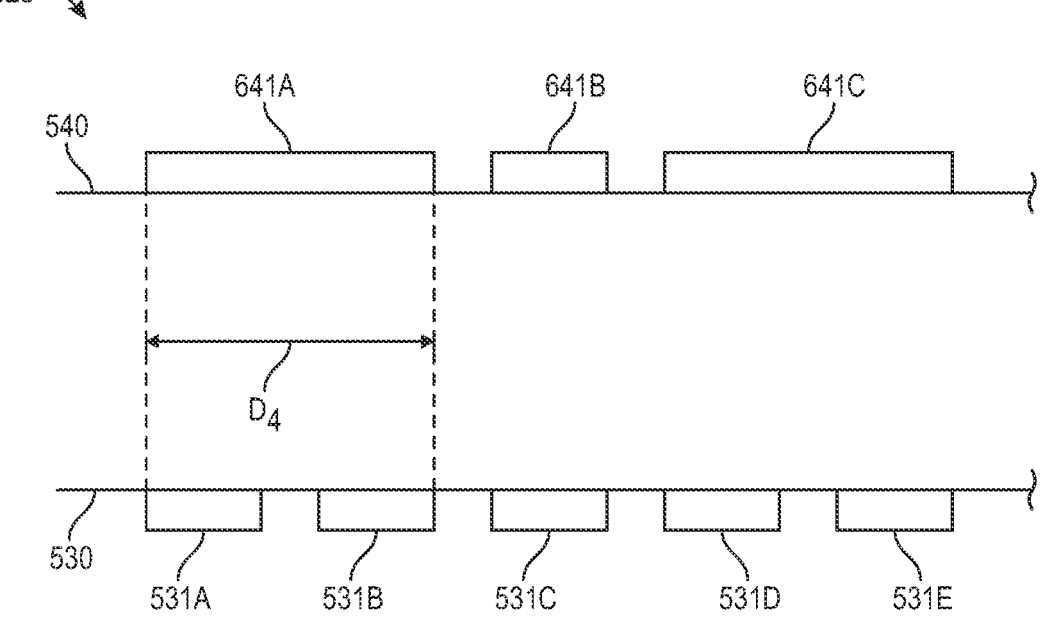

As shown in FIGS. 5A-5D, the signal delivery device 521 includes ten lead electrodes. However, in other embodiments, as shown in FIGS. 6A-10, signal delivery devices can include more or fewer (e.g., two, three, four, five, six, seven, eight, nine, twelve, fourteen, fifteen, sixteen, or twenty) lead electrodes. Additionally, or alternatively, the lead electrodes may be arranged in a different configuration. As shown in FIG. 6A, the signal delivery device 621 includes many of the same features of the signal delivery device 521 (FIG. 5A), including the first region 530, the second region 540, the intermediate region 550, and the first lead electrodes 531. The signal delivery device 621, or more particularly the lead body 625, also includes second lead electrodes including a primary second lead electrode 641A, a secondary second lead electrode 641B, and a tertiary second lead electrode 641C (collectively referred to as "the second lead electrodes 641"). The first lead electrodes 531 and the second lead electrodes 641 can each span the same distance ($D_2$) of the respective first region 530 and second region 540. As shown in FIG. 6B, the primary second lead electrode 641A can span a distance ($D_4$) equal to that of the primary and secondary first lead electrodes 531A, 531B. The first conductors 523A can be electrically coupled to the first lead electrodes 531 and one or more second conductors 623B can be electrically coupled to the second lead electrodes 641.

The arrangement of the lead electrodes on the lead body 625 can provide multiple advantages for delivering stimulation to a patient. For example, having the first region 530 with the first lead electrodes 531 and the second region 540 with fewer second lead electrodes 641 relative to the second lead electrodes 541 (FIG. 5A) can decrease the energy required to deliver bipolar stimulation to a target nerve between the first and second regions 530, 540. Additionally, including a single electrode (e.g., the primary second lead electrode 641A) with a larger width or surface area at least equal to that of multiple electrodes (e.g., the primary and secondary first lead electrodes 541A, 541B) can enable the signal delivery device 621 to use less energy to deliver bipolar stimulation, while also covering at least the same amount of surface area of the lead body 625. In doing so, the lead electrodes on the first region 530 and the second region 540 can still precisely target particular nerves or areas that result in improved therapy for the patient. Additionally, including a single electrode (e.g., the primary second lead electrode 641A) with a larger width or surface area at least equal to that of multiple electrodes (e.g., the primary and secondary first lead electrodes 541A, 541B) can enable more of a particular tissue, which may be necessary to obtain a desired effect. Stated differently, a smaller electrode may not excite enough tissue to obtain the desired effect.

Figure 7A:
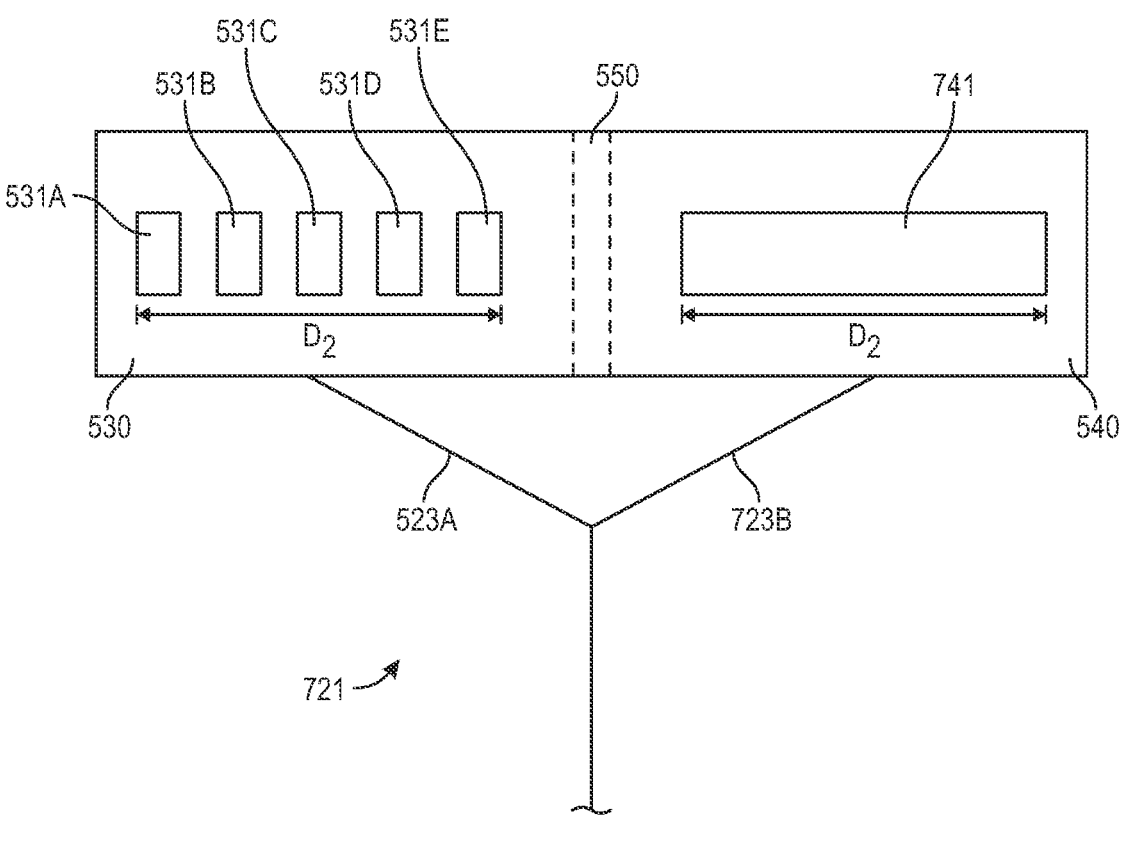
Figure 7B:
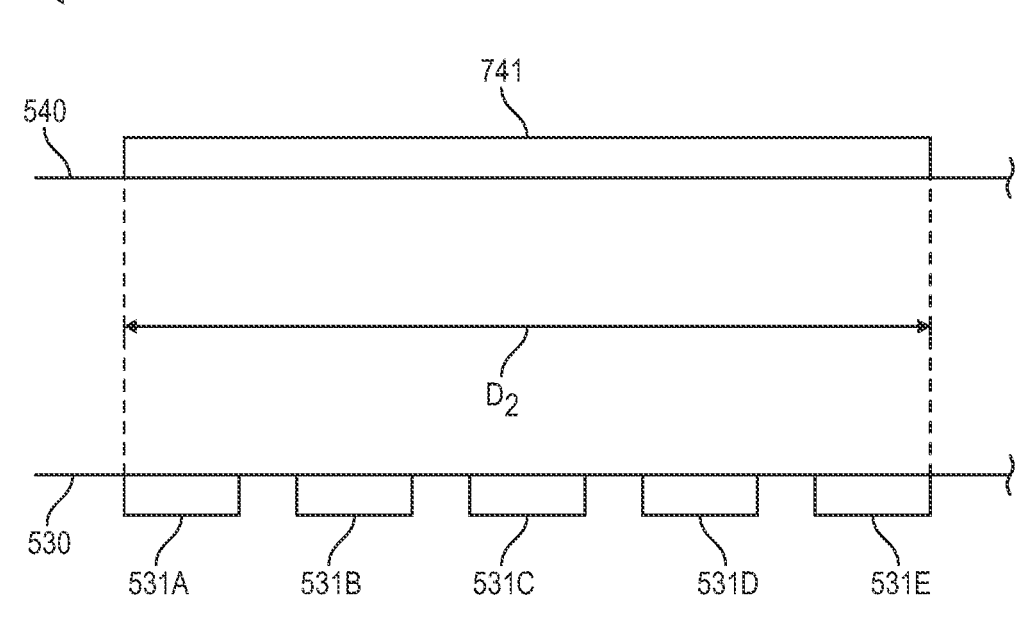

Referring next to FIG. 7A, the signal delivery device 721 includes many of the same features of the signal delivery devices 521, 621 (FIGS. 5A and 6A), including the first region 530, the second region 540, the intermediate region 550, and the first lead electrodes 531. The signal delivery device 721, or more particularly the lead body 725, also includes a second lead electrode 741 on the second region 540. As shown in FIGS. 7A and 7B, the first lead electrodes 531 and the second lead electrode 741 can each span the same distance ($D_2$) of the respective first region 530 and second region 540. The first conductors 523A can be electrically coupled to the first lead electrodes 531 and one or more second conductors 723B can be electrically coupled to the second lead electrodes 641.

The arrangement of the lead electrodes on the lead body 725 can provide multiple advantages for delivering stimulation to a patient. For example, having the first region 530 with the first lead electrodes 531 and the second region 540 with a single second lead electrodes 741 (e.g., relative to the second lead electrodes 541 of FIG. 5A) can decrease the energy required to deliver bipolar stimulation to a target nerve between the first and second regions 530, 540. Additionally, including a single electrode on the second region 540 with a width or surface area at least equal to that of multiple electrodes (e.g., the primary and secondary first lead electrodes 541A, 541B) enables the signal delivery device to use less energy to deliver bipolar stimulation, while also covering at least the same amount of surface area of the lead body 725. In doing so, the lead electrodes on the first region 530 and the second region 540 can still precisely target particular nerves or areas that treat hypertension or provide other therapy for the patient.

Figure 8A:
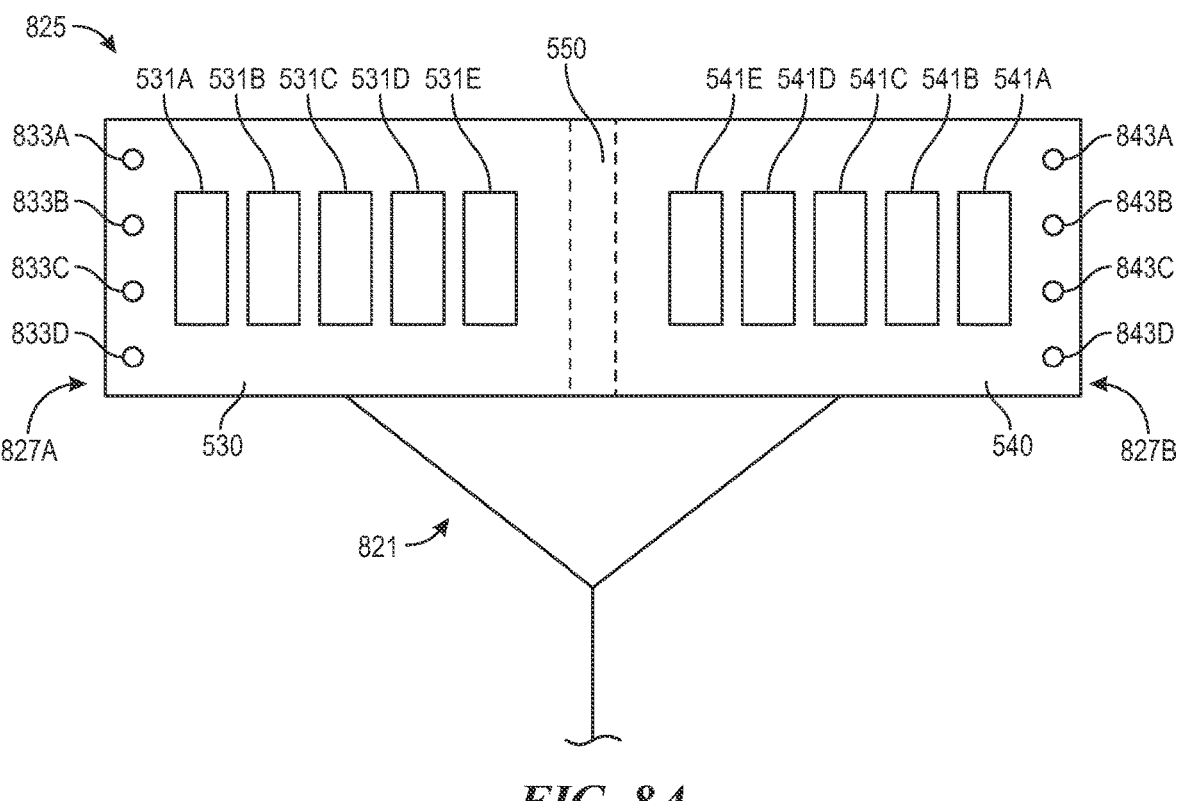

Referring next to FIG. 8A, the signal delivery device 821 includes many of the same features of the signal delivery device 521 (FIG. 5A), including the first region 530, the second region 540, the intermediate region 550, the first lead electrodes 531, and the second lead electrodes 541. The signal delivery device 821, and more particularly the lead body 825, include a first set of suture holes 833A-833D (collectively referred to as "the first sutures holes 833") on the first region 530, and a corresponding set of second suture holes 843A-843D (collectively referred to as "the second suture holes 843") on the second region 540. In the illustrated embodiment, the first suture holes 833 are positioned laterally between the first lead electrodes 531 and a first or left end portion 827A of the lead body 825, or laterally outward of the first lead electrodes 531. The second suture holes 843 are positioned laterally between the second lead electrodes 541 and a second or right end portion 827B of the lead body 825, or laterally outward of the second lead electrodes 541. In other embodiments, one or more of the first suture holes 833 and/or second suture holes 843 can be positioned elsewhere on the signal delivery device, such as the top and/or bottom of the first region 530 and/or the second region 540.

With continued reference to the illustrated embodiment, the first suture holes 833 are aligned with one another in a first direction, and the first lead electrodes 531 are aligned with one another in a second direction that is perpendicular, or at least generally perpendicular, to the first direction. Additionally, the second suture holes 843 are aligned with one another in the first direction, and the second lead electrodes 541 are aligned with one another in the second direction. In other embodiments, the first suture holes 833 can be positioned between the first lead electrodes 531 and the intermediate region 550, toward another side of the first lead electrodes 531, between individual ones of the first lead electrodes 531, and/or at other suitable positions and/or orientations relative to the first lead electrodes 531. In these and other embodiments, the second suture holes 843 can be positioned between the second lead electrodes 541 and the intermediate region 550, toward another side of the second lead electrodes 541, between individual ones of the second lead electrodes 541, and/or at other suitable positions and/or orientations relative to the second lead electrodes 541.

Figure 8B:
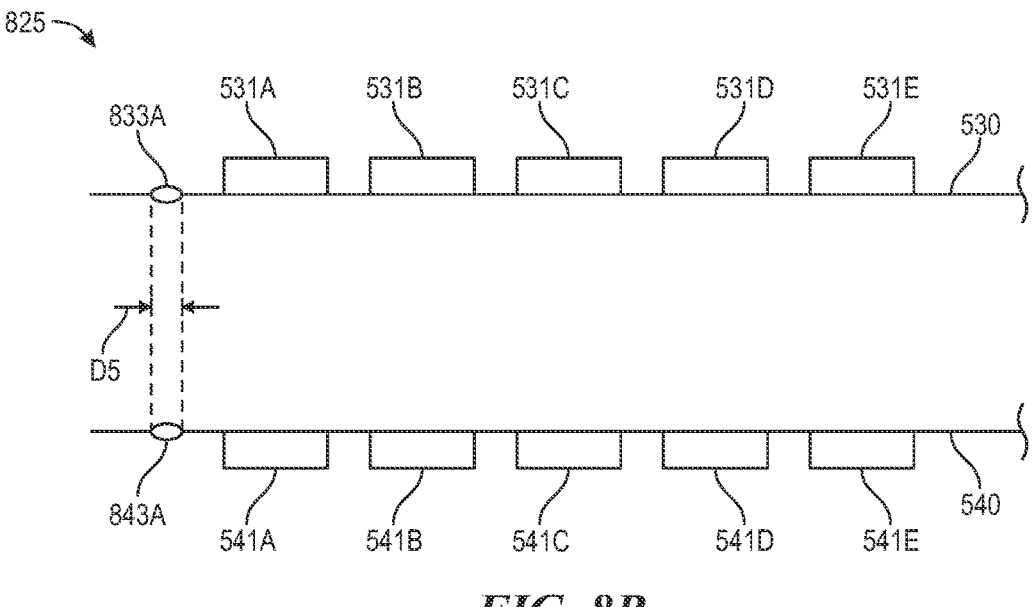

Referring additionally to FIG. 8B, the first region 530 can be positioned over the second region 540 by, for example, folding the first region 530 over the second region 540 (or vice versa) about the intermediate region 550. In this configuration, individual first suture holes 833 are positioned over or at least partially over (e.g., at least partially aligned with and/or overlapping) corresponding individual second suture holes 843. For example, when the first region 530 is positioned over the second region 540, a primary first suture 833A is positioned over a primary second suture hole 843A, and so on and so forth. Each of the second suture holes 843 can be configured to receive a corresponding one of the first suture holes 833, for example, to at least partially secure the first region 530 and the second region 540 relative to one another and/or prevent, or at least partially prevent, the signal delivery device 821 from transitioning away from the folded state. In some embodiments, the individual first suture holes 833 and the individual second suture holes 843 can span the same distance ($D_5$) of the corresponding first region 530 or second region 540 and/or overlap completely with one another. In other embodiments, one or more of the individual first suture holes 833 can span a different distance of the corresponding first region 530 or second region 540 and/or be offset relative to one another.

Figure 9:
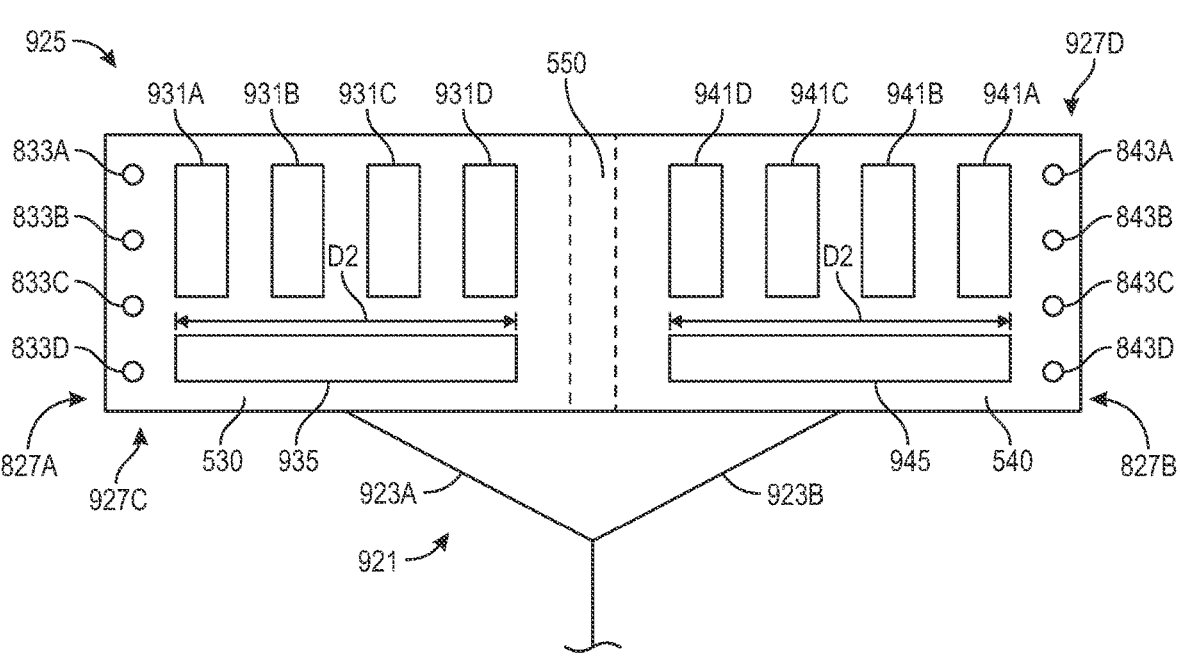

Referring next to FIG. 9, the signal delivery device 921 includes many of the same features of the signal delivery device 821 (FIG. 8A), including the first region 530, the second region 540, the intermediate region 550, the first suture holes 833, and the second suture holes 843. Additionally, the signal delivery device 921, or more particularly the lead body 925, includes a first set of lead electrodes 931A-931D (collectively referred to as "the first lead electrodes 931") on the first region 530 that can be at least generally similar or identical in structure and/or function to the first lead electrodes 531 (FIGS. 5A, 6A, 7A, 8A), and a second set of lead electrodes 941A-941D (collectively referred to as "second lead electrodes 941") on the second region 540 that can be at least generally similar or identical in structure and/or function to the second lead electrodes 541 (FIGS. 5A and 8A). Furthermore, the signal delivery device 921, or more particularly, the lead body 925, includes a third lead electrode 935 on the first region 530 and a fourth lead electrode 945 on the second region 540. The third lead electrode 935 and the first lead electrode 931 can span a same distance (D2) on the first region 530, and/or the fourth lead electrode 945 and the second lead electrodes 941 can span a same distance (D2) on the second region 540. In the illustrated embodiment, the third lead electrode 935 and the fourth lead electrode 945 are positioned proximate to a third or lower end portion 927C of the lead body 925 to which, for example, a pair of conductors 923A-B are coupled. Accordingly, in the illustrated embodiment, the first lead electrodes 931 are positioned between the third lead electrode 935 and a fourth or upper end portion 927D of the lead body 925, and the second lead electrodes 941 are positioned between the fourth lead electrode 945 and the upper end portion 927D. One or more first conductors 923A can be electrically coupled to the first lead electrodes 931 and/or the third lead electrode 935, and/or one or more second conductors 923B can be electrically coupled to the second lead electrodes 941 and/or the fourth lead electrode 945.

The first region 530 can be positioned over the second region 540, for example, by folding the first region 530 over the second region 540 (or vice versa) about the intermediate region 550. In this configuration, individual first lead electrodes 931 are positioned over or at least partially over (e.g., at least partially aligned with and/or overlapping) corresponding individual second lead electrodes 941. For example, when the first region 530 is positioned over the second region 540, a primary first lead electrode 931A is positioned over a primary second lead electrode 941A, and so on and so forth. Additionally, in some embodiments the third electrode 935 is positioned over the fourth electrode 945.

Figure 10:
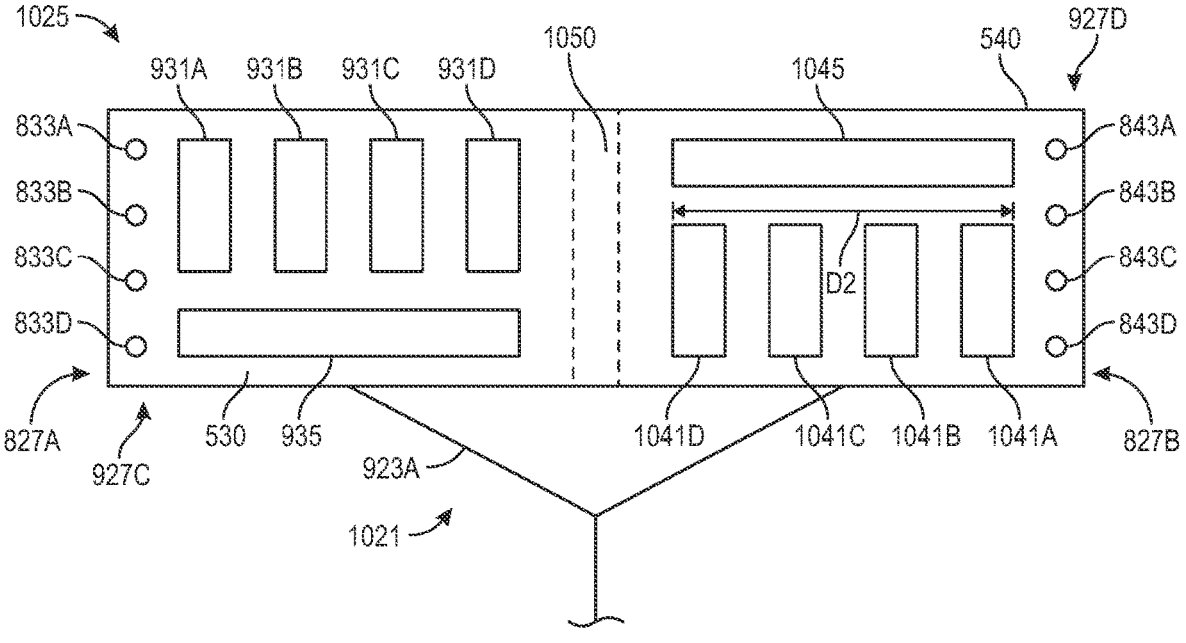

Referring next to FIG. 10, the signal delivery device 1021 includes many of the same features of the signal delivery device 921 (FIG. 9), including the first region 530, the second region 540, the intermediate region 550, the first lead electrode 931, the third lead electrode 935, the suture holes 833, and the suture holes 843. Additionally, the signal delivery device 921, or more particularly the lead body 925, includes a second set of lead electrodes 1041A-1041D (collectively referred to as "second lead electrodes 1041") on the second region 540 that can be at least generally similar or identical in structure and/or function to the second lead electrodes 941 (FIG. 9). Furthermore, the signal delivery device 921, or more particularly the lead body 925, includes a fourth lead electrode 1045 on the second region 540 that can be at least generally similar or identical in structure and/or function to the fourth lead electrode 945 (FIG. 9). The fourth lead electrode 1045 and the second lead electrodes 1041 can span a same distance ($D_2$) on the second region 540. In the illustrated embodiment, the fourth lead electrode 1045 is positioned proximate the upper end portion 927D of the lead body 925, such that the second lead electrodes 1041 are positioned between the fourth lead electrode 1045 and the upper end portion 927D, for example, opposite the arrangement of the first lead electrode 931 and the third lead electrode 935.

The first region 530 can be positioned over the second region 540, for example, by folding the first region 530 over the second region 540 (or vice versa) about the intermediate region 550. In this configuration, individual first lead electrodes 931 are positioned over or at least partially over (e.g., at least partially aligned with and/or overlapping) corresponding individual second lead electrodes 941. In some embodiments, the third lead electrode 935 can be positioned over or at least partially over one or more of the second lead electrodes 1041 and/or the fourth lead electrode 1045 can be positioned over or at least partially over one or more of the first lead electrodes 931.

The lead electrodes of lead bodies 525, 625, 725, 825, 925, 1025 shown in FIGS. 5A, 6A, 7A, and 8A-10, respectively, are included on both the first region 530 and the second region 540 thereof. However, in some embodiments the lead electrodes may only be included on one of the first region 530 or the second region 540. That is, in some embodiments no lead electrodes may be included on one of the first region 530 or the second region 540. In such embodiments, monopolar stimulation can be delivered via one of the lead electrodes, or bipolar stimulation can be delivered via two or more of the lead electrodes (e.g., adjacent lead electrodes). Advantageously, in such embodiments, the lead electrodes can require lower impedance, lower energy requirements, and/or less unintentional stimulation of non-target nerves and tissues.

Figure 11A:
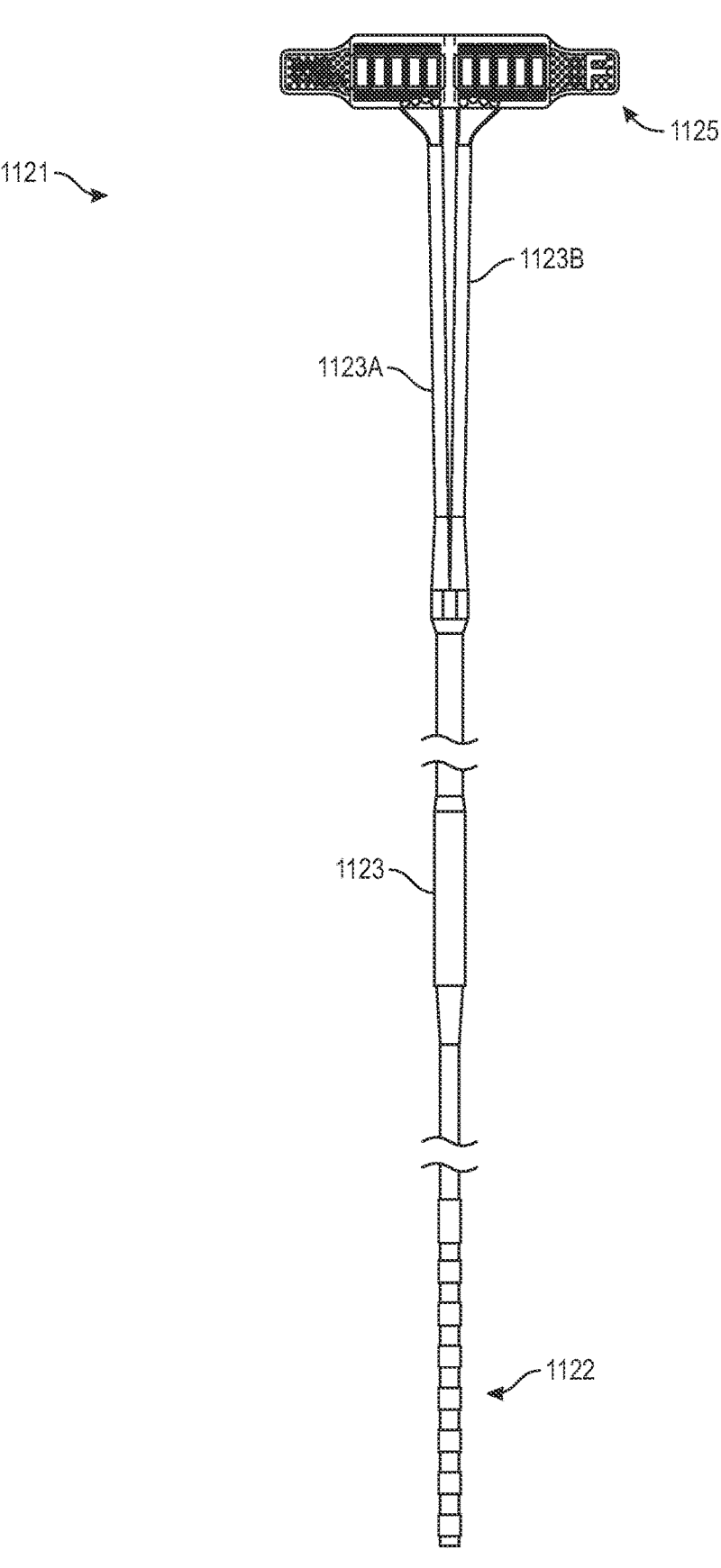

Referring next to FIG. 11A, the signal delivery device 1121 includes a lead body 1125, one or more conductors 1123, and a connector portion 1122. The lead body 1125 is described in greater detail below with reference to FIG. 11B, and the connector portion 1122 is described in greater detail below with reference to FIG. 11C. The conductors 1123 can extend between and couple (e.g., communicatively, electrically, mechanically, etc.) the lead body 1125 and the connector portion 1122. In the illustrated embodiment, the conductors 1123 include a first conductor branch 1123A and a second conductor branch 1123B, each of which can be coupled to a respective portion or region of the lead body 1125. For example, the first conductor branch 1123A can be coupled to a first body region of the lead body 1125 (and/or one or more features thereof) and the second conductor branch 1123B can be coupled to a second body region of the lead body 1125 (and/or one or more features thereof).

Figure 11B:
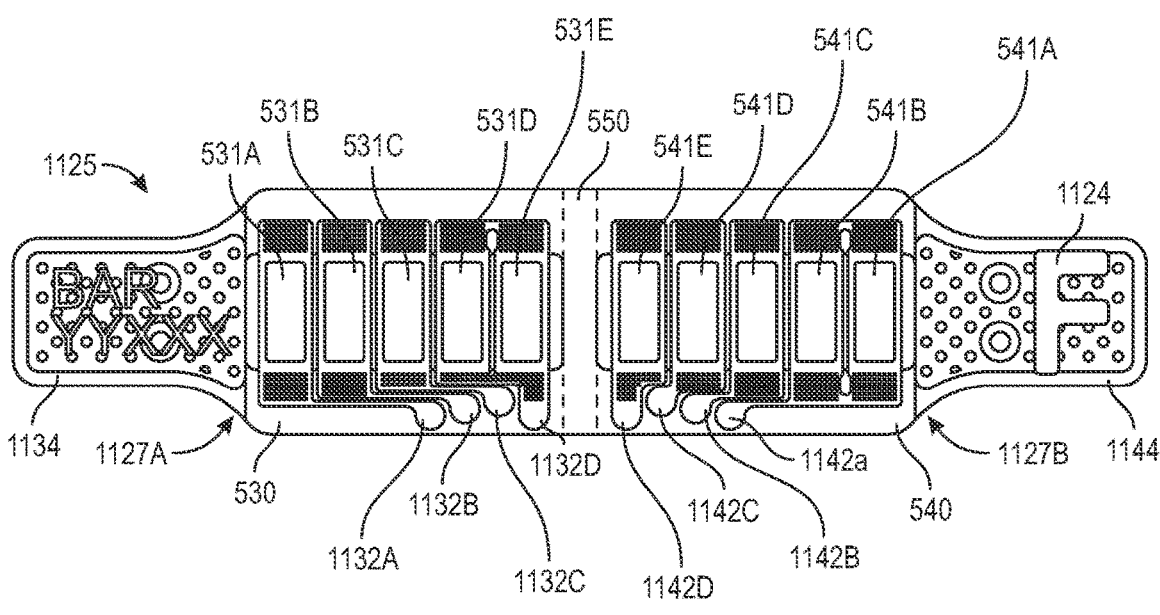

Referring next to FIG. 11B, the lead body 1125 includes many of the same features of the lead body 525 (FIG. 5A), including the first region 530, the second region 540, the intermediate region 550, the first lead electrodes 531, and the second lead electrodes 541. The lead body 1125 includes first electrical contacts 1132A/B/C/D (collectively referred to as "first electrical contacts 1132") which are coupled to respective ones of the first lead electrodes 531, and second electrical contacts 1142A/B/C/D (collectively referred to as "second electrical contacts 1142") which are coupled to respective ones of the second lead electrodes 541. For example, the primary first lead electrode 531A is coupled to a primary first electrical contact 1132A, the secondary first lead electrode 531B is coupled to a secondary first electrical contact 1132B, the tertiary first lead electrode 531C is coupled to a tertiary first electrical contact 1132C, and the quaternary and quinary first lead electrodes 531D, 531E share a quaternary first electrical contact 1132D. Similarly, the primary and secondary second lead electrodes 541A, 541B share a primary second electrical contact 1142A, the tertiary second lead electrode 541C is coupled to a secondary second electrical contact 1142B, the quaternary second lead electrode 541D is coupled to a tertiary second electrical contact 1142C, and the quinary second lead electrode 541E is coupled to a quaternary second electrical contact 1142D. In other embodiments, all of the first and/or second lead electrodes 531, 541 can have their own electrical contact, or can share electrical contacts. For example, as shown in FIG. 11D, in some embodiments, each of the first lead electrodes 531A-E (collectively referred to as "first lead electrodes 531") has a corresponding first electrical contact 1132A-E (collectively referred to as "first electrical contacts 1132") and each of the second lead electrodes 541A-E (collectively referred to as "second lead electrodes 541") has a corresponding second electrical contact 1142A-E (collectively referred to as "second electrical contacts 1142"). In these and/or other embodiments, individual ones of the first electrical contacts 1132 and/or the second electrical contacts 1142 can be positioned on a side of a corresponding one of the first lead electrodes 531 and/or the second lead electrodes 541, for example, proximate to one or more side portions of the lead body 1125. For example, as shown in FIG. 11D, first electrical contacts 1132A-C and second electrical contacts 1142A-C are positioned proximate to a fourth or top side portion 1127D of the lead body 1125 and first electrical contacts 1132D, 1132E and second electrical contacts 1142D, 1142E are positioned proximate to a third or bottom side portion 1127C of the lead body 1125. As another example, in the embodiment shown in FIG. 11B, each of the electrical contacts 1132, 1142 are positioned proximate to a same side of the lead body 1125, for example, on a same side of the first and second lead electrodes 531, 541. Additionally, in the embodiment shown in FIG. 11B, each of the electrical contacts 1132, 1142 are positioned closer to the intermediate region 550 than the corresponding first and second lead electrodes 531, 541.

Referring again to FIG. 11B, the lead body 1125 can include a first tab or elongate portion 1134 extending from a first side portion 1127A of the first region 530, and a second tab or elongate portion 1144 extending from a second side portion 1127B of the second region 540. The tabs 1134, 1144 can be tapered and can aid a practitioner in positioning and/or otherwise manipulating the lead body 1125. For example, the practitioner can grip one or both of the tabs 1134, 1144 when transitioning the lead body 1125 between the open configuration and the closed configuration, when implanting the lead body 1125, etc. The first side portion 1127A can be opposite the intermediate region 550 from the first region 530, such that the first region 530 is positioned between the first tab 1134 and the intermediate region 550. Similarly, the second side portion 1127B can be opposite the intermediate region 550 from the second region, such that the second region 540 is positioned between the second tab 1144 and the intermediate region 550. In these and/or other embodiments, one or more tabs can be positioned on other sides of the lead body 1125, e.g., adjacent the intermediate region 550. Moreover, in these and/or other embodiments, the lead body 1125 can include one or more alignment and/or orientation features 1124, for example, to aid the practitioner in identifying which face/surface of the lead body 1125 includes the lead electrodes 531, 541. In the illustrated embodiment, the second tab 1144 includes the alignment and/or orientation feature 1124. In other embodiments, the first tab 1134 and/or another portion of the lead body 1125 can include one or more of the alignment and/or orientation features 1124. In these and/or other embodiments, individual ones of the one or more alignment and/or orientation features 1124 can be printed, etched, deposited, or otherwise formed on the lead body 1125. In the illustrated embodiment, the alignment feature 1124 includes the letter "F." The lead body 1125 can be at least partially transparent, and accordingly, a practitioner can use the letter "F" to identify which face of the lead body 1125 includes the lead electrodes 531, 541, for example, because the appearance of the letter "F" is orientation-specific and has a different appearance when viewed from the front and the back. In these and/or other embodiments, one or more of the alignment and/or orientation features 1124 can have another orientation-specific configuration.

Figure 11C:
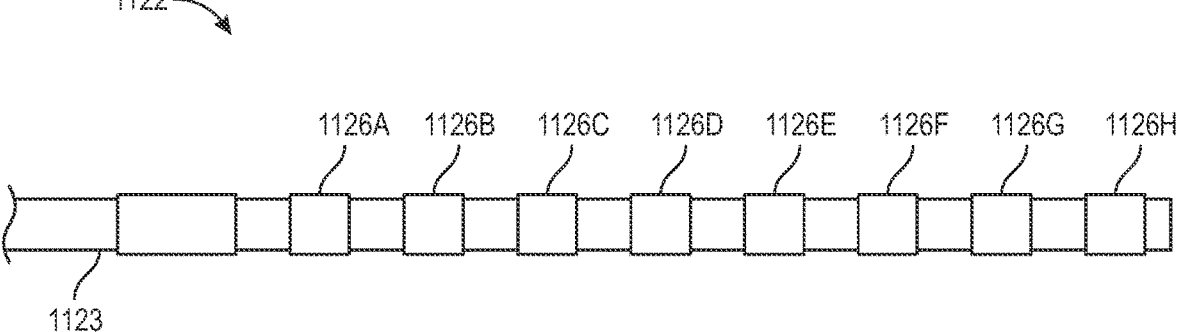
Figure 11D:
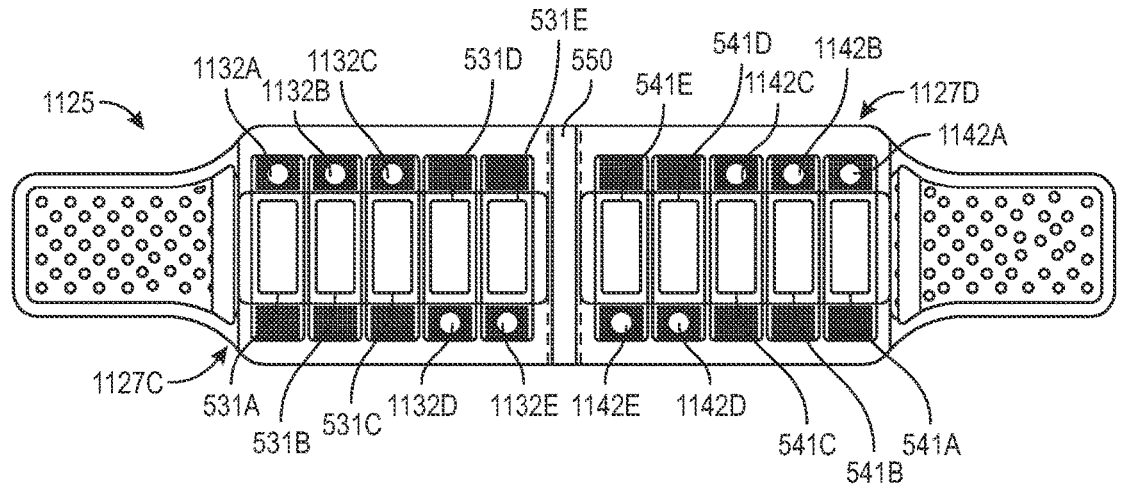

Referring next to FIG. 11C, the connector portion 1122 can include one or more lead terminals 1126 positioned at least partially around the conductors 1123. In the illustrated embodiment, the connector portion 1122 includes eight lead terminals 1126A-H, each of which is electrical coupled to one of the electrical contacts 1132, 1142 (FIG. 11B). For example, the primary first electrical contact 1132A can be coupled to the first lead terminal 1126A, the secondary first electrical contact 1132B can be coupled to the second lead terminal 1126B, the tertiary first electrical contact 1132C can be coupled to the third lead terminal 1126C, the quaternary first electrical contact 1132D can be coupled to the fourth lead terminal 1126D, the primary second electrical contact 1142A can be coupled to the fifth lead terminal 1126E, the secondary second electrical contact 1142B can be coupled to the sixth lead terminal 1126F, the tertiary second electrical contact 1142C can be coupled to the seventh lead terminal 1126G, and the quaternary second electrical contact 1142D can be coupled to the eighth lead terminal 1126H. In other embodiments, one or more of the electrical contacts 1132, 1142 can be connected to one or more other and/or additional lead terminals 1126. In these and/or other embodiments, individual ones of the lead terminals 1126 can be received by and/or electrically coupled to the implantable neuromodulator 101 (FIG. 4A) or another signal generator, for example, to allow the implantable neuromodulator 101 to delivery electrical stimulation to the patient via individual ones of the lead electrodes 531, 541 (FIG. 11B).

Figure 11E:
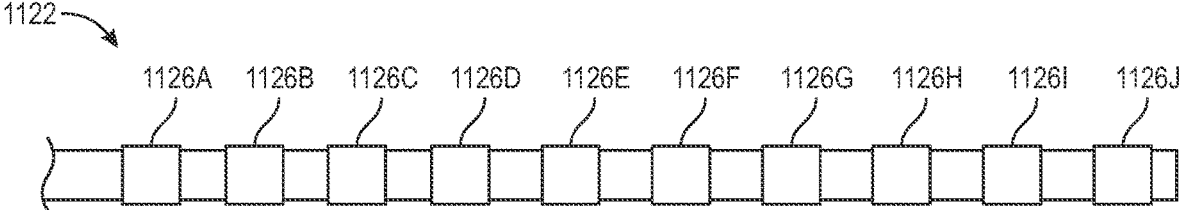

Referring to FIG. 11E, each of the electrical contacts 1132A-E and 1142A-E of the lead body 1125 of FIG. 11D can be connected to a corresponding lead terminal 1126A-J, as described previously with reference to FIG. 11C.

Figure 12:
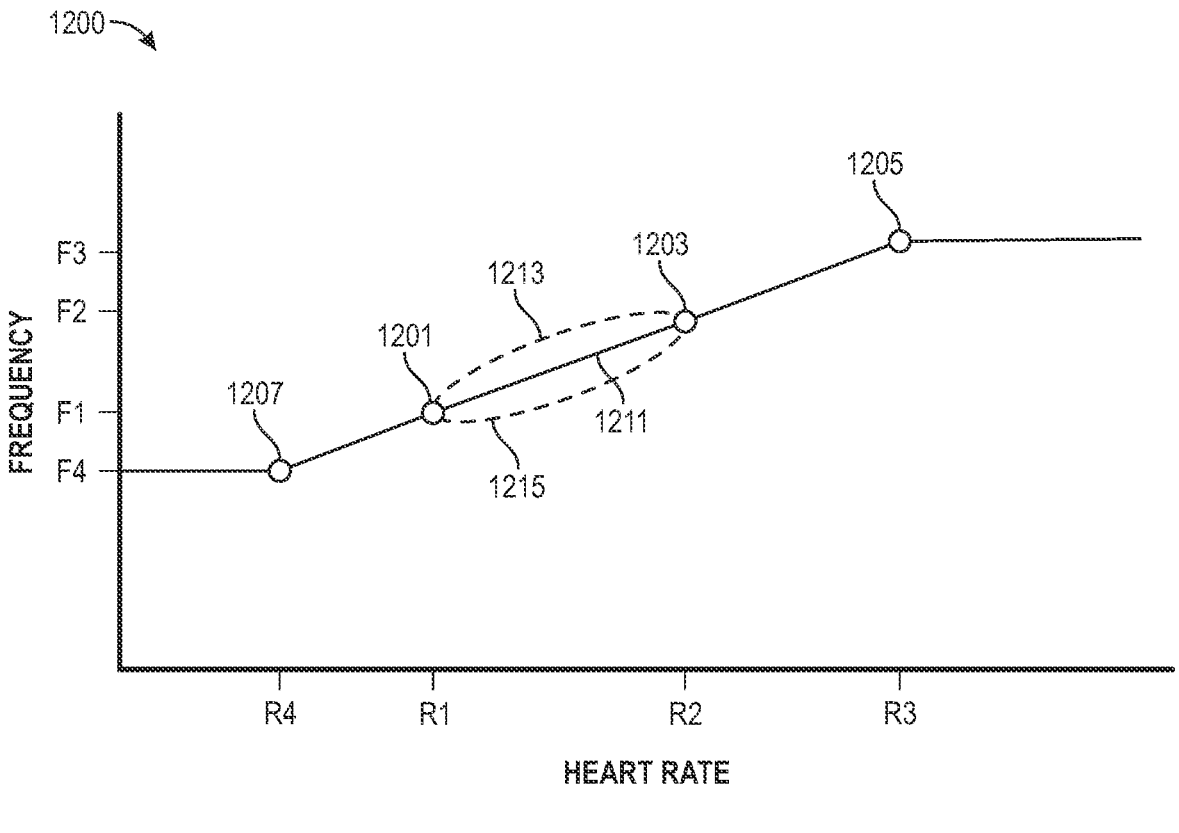
FIG. 12 is a chart illustrating the relationship of frequency of neuromodulation pulses applied via a patient treatment system and heart rate of a patient, in accordance with embodiments of the present technology.

FIG. 12 is a chart 1200 illustrating the relationship of frequency of neuromodulation pulses applied via a patient treatment system (e.g., the system 100 (FIGS. 3, 4A, 4B)) and the heart rate of a patient, in accordance with embodiments of the present technology. In these and/or other embodiments, one or more other neuromodulation pulse parameters (e.g., amplitude, pulse width, duty cycle, etc.) and/or the overall intensity of the neuromodulation pulses (e.g., including values for one or more of the neuromodulation pulse parameters) can be modulated depending on the heart rate. The "heart rate" used throughout the disclosure can be an average heart rate over time (e.g., over the previous 10 seconds, 30 seconds, one minute, two minutes, etc.), a filtered heart rate (e.g., determined at least in part on the patient's R-R intervals), or a combination thereof. As described herein, embodiments of the present technology attempt to deliver therapy to a patient, or more particularly stimulation to a CSN of the patient that is modulated based at least in part on activity (e.g., heart rate, R-R interval, augmentation index, and/or blood pressure) of the patient. In doing so, therapy can be delivered to the patient in a non-dilutive manner, for example, so that the frequency of neuromodulation pulses delivered to the CSN increases as the activity or heart rate of the patient increases. Stated differently, therapy can be delivered based at least in part on heart rate of the patient such that the number of pulses delivered to the patient per cardiac cycle or the time interval between two consecutive R waves in an electrocardiogram (ECG) (i.e., R-R interval) are consistent. In at least some embodiments, for example, a sudden change in the patient's heart rate (e.g., an increase or decrease greater than a predetermined threshold of at least 10 beats per minute (BPM), 20 BPM, 30 BPM, 40 BPM, 50 BPM, 60 BPM, 70 BPM, etc.) can produce a corresponding change in the rate (e.g., time coefficient) of the neuromodulations pulses.

As shown in FIG. 12, the frequency of neuromodulation pulses generated and/or delivered to the patient can modulate depending on the obtained heart rate or other parameter(s) of the patient. For example, a first heart rate (R1) (e.g., 60 BPM) can correspond to a first frequency (F1) (e.g., 20 Hertz (Hz)) for the pulses at point 1201, and a second heart rate (R2) (e.g., 120 BPM) higher than the first heart rate (R1) can correspond to a second frequency (F2) (e.g., 40 Hz) at point 1203 for the pulses higher than the first frequency (F1). As also shown in FIG. 12, a third heart rate (R3) higher than the second heart rate (R2) can correspond to a third frequency (F3) at point 1105 for the pulses higher than the second frequency (F2) of pulses, and a fourth heart rate (R4) lower than the first heart rate (R1) can correspond to a fourth frequency at point 1207 for the pulses lower than the first frequency (F1). In some embodiments, the third heart rate (R3) and the fourth heart rate (R4) serve as respective upper and lower endpoints for heart rate. In such embodiments, a heart rate above the third heart rate (R3) will not result in an increased frequency of pulses relative to the frequency of pulses provided at the third heart rate (R3), and a heart rate below the fourth heart rate (R4) will not result in a decreased frequency of pulses relative to the frequency of pulses provided at the fourth heart rate (R4).

In some embodiments, one or more of the frequencies F1-F4 can be average frequencies, and the frequency of the signal delivered to the patient can vary from a base frequency. For example, in some embodiments the second frequency has an average or base of 40 Hz with an average cycle length of 25 ms, but individual cycle lengths have a randomly generated variance from the average cycle length, for example, 22 ms-26 ms-24 ms-25 ms-28 ms (as opposed to 25 ms-25 ms-25 ms-25 ms-25 ms). Without being bound by theory, varying signal frequencies and/or cycle lengths can reduce or prevent patient habituation to the neuromodulation pulses, thus making the underlying more effective over time.

In some embodiments, the heart rates obtained from patients and the corresponding frequencies of pulses delivered via the patient treatment system can serve as known points, and a device or component of the patient treatment system can interpolate between the known points to deliver the appropriate number of pulses by modulating frequency. In such embodiments, the interpolation can be linear (as shown via line 1211) or non-linear. The interpolation can be based at least in part on (i) how high or low the heart rate is for that particular patient or patient demographic (e.g., age, weight, etc.), (ii) whether the heart rate is outside a "normal range," and/or (iii) other inputs available to the system (e.g., resting heart rate of the patient). For example, the implantable neuromodulator 101 can store a history of heart rates over several different time scales (e.g., one or more days, weeks, months, etc.). The stored history of heart rates can include a histogram of heart rates and/or associated statistics that can be used to modulate one or more of the neuromodulation pulse parameters. Additionally, or alternatively, the interpolation can vary depending on whether the patient's heart rate is increasing or decreasing. For example, the frequency of pulses delivered can correspond to the line 1213 for a heart rate between the second heart rate (R2) and the first heart rate (R1) that is decreasing, and can correspond to the line 1215 for a heart rate between the first heart rate (R1) and the second heart rate (R2) that is increasing. In these and/or other embodiments, the relationship between frequency (and/or other neuromodulation pulse parameters) and heart rate (and/or other physiological parameters of the patient) can be linear, continuous, stepped, or another suitable relationship.

As noted above, the frequency of pulses generated is based on heart rate. However, in some embodiments the frequency of pulses can be based on other physiological parameters, including blood pressure (e.g., systolic blood pressure, diastolic blood pressure), physical activity detected by one or more I/O devices (e.g., the I/O devices 109 (FIG. 4A), an accelerometer or other sensor, as disclosed herein), or the R-R interval for a QRS complex, which is a combination of three of the graphical deflections seen via a electrocardiogram (ECG or EKG). For example, the heart rate can be compared with motion data from an accelerometer, for example, to determine whether the heart rate is expected or abnormal for the patient's level of movement (e.g., corresponding to physical activity level) during a given time. Additionally, or alternatively, the physiological parameters can include vessel wall distension (e.g., volume conductance and/or wall stretch) and/or pulse pressure waveforms indicating vascular stiffness. As described herein, signals associated with the R-R interval or R-wave can be sensed via vectors of the patient treatment system. Blood pressure can be obtained via an implanted or external blood pressure measurement device directly coupled or wirelessly coupled (e.g., via Bluetooth, ANT, telemetry, etc.) to the patient treatment system, or more specifically to the neuromodulator 101 (FIG. 4A or 4B). The obtained blood pressure measurement can be an average blood pressure measured over time (e.g., over the previous 10 seconds, 30 seconds, one minute, two minutes, etc.), a filtered blood pressure, or a combination thereof.

Figure 13A:
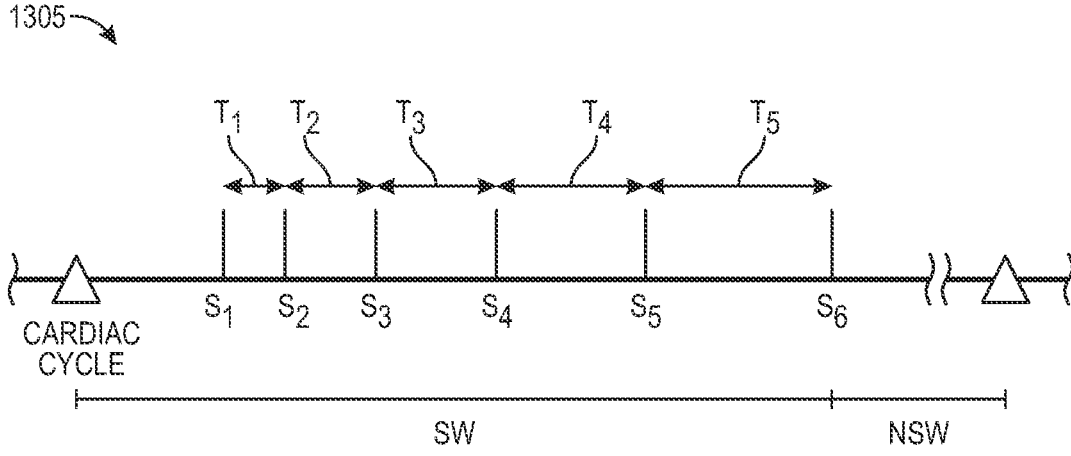
FIGS. 13A-13C are illustrations of neuromodulation pulses generated over time via a patient treatment system, in accordance with embodiments of the present technology.
Figure 13B:
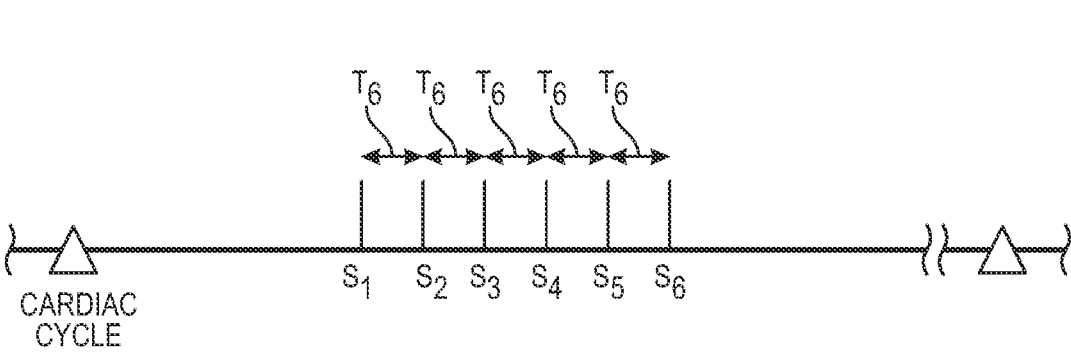
Figure 13C:
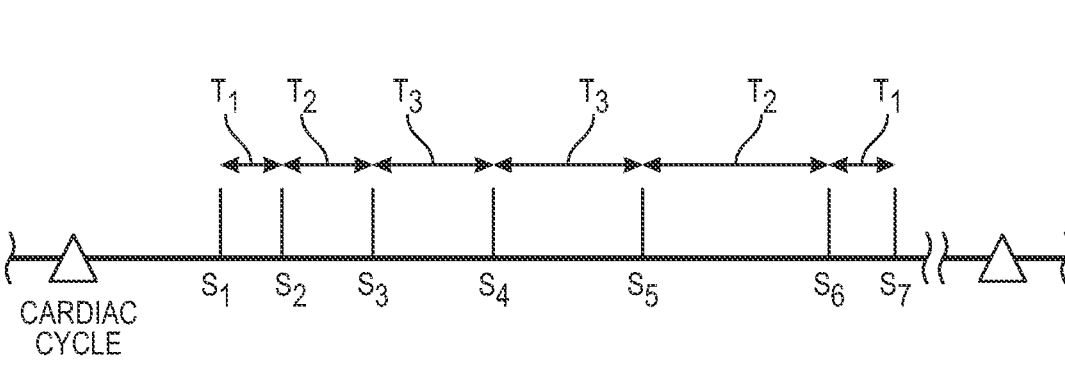

FIGS. 13A-13C are illustrations of neuromodulation pulses generated during a cardiac cycle via a patient treatment system (e.g., the system 100 (FIGS. 3, 4A, 4B)), in accordance with embodiments of the present technology. As described herein, the neuromodulation pulses generated via the neuromodulator of embodiments of the present technology can include a burst of pulses having individual pulses that vary in delay relative to the immediately previous pulse. For example, individual pulses relative to the immediately previous pulse can have an increased delay, a decreased delay, or an identical delay. In embodiments wherein the delay increases over time, the delay may be determined using a non-linear function, such as Equations 1 or 2 below.

$$\text{Delay} = t * \exp^{\alpha * n} \qquad \text{(Equation 1)}$$

$$\text{Delay} = T + (t * \exp^{\alpha * n}) \qquad \text{(Equation 2)}$$

Wherein:
  T=the delay of the previous pulse
  t=time(s)

α=a programmable variable n=pulse number

FIG. 13A illustrates neuromodulation pulses 1305 generated after a cardiac cycle that has an increased delay over time. That is, the neuromodulation pulses 1305 include a first stimulation (S$_1$) after the beginning of a cardiac cycle, a second stimulation (S$_2$) after a first time delay (T$_1$), a third stimulation (S$_3$) after a second time delay (T$_2$) greater than the first time delay (T$_1$), a fourth stimulation (S$_4$) after a third time delay (T$_3$) greater than the second time delay (T$_2$), a fifth stimulation (S$_5$) after a fourth time delay (T$_4$) greater than the third time delay (T$_3$), and a sixth stimulation (S$_6$) after a fifth time delay (T$_5$) greater than the fourth time delay (T$_4$). In some embodiments, the first stimulation (S$_1$) may be delayed from the beginning of the cardiac cycle by a time delay less than the first time delay (T$_1$) and/or by a predetermined time. The neuromodulation pulses 1305 include six pulses or stimulations, however, in other embodiments, the neuromodulation pulses 1305 can include more or fewer (e.g., 20, 16, 12, 10, 8, or 4) pulses.

Without being bound by theory, the natural baroresponse can consist of a burst of pulses immediately following the detection of a cardiac depolarization event (e.g., a carotid artery stretch) and that increase in delay over time. Embodiments of the present technology can attempt to mimic the natural baroresponse by generating neuromodulation pulses that increase in delay over time for a single cardiac cycle and are delivered a predetermined time after a cardiac depolarization event is detected. The frequency of the individual pulses and/or the delay between adjacent pulses can be automatically adjusted by the patient treatment system, for example, based on changes in the R-R intervals detected. For example, as the heart rate increases and/or the R-R interval time decreases the frequency of the individual pulses increases (e.g., the delay between individual pulses decreases), and as the heart rate decreases and/or the R-R intervals time increases, the frequency of the individual pulses decreases (e.g., the delay between individual pulses creases).

FIGS. 13B and 13C illustrate neuromodulation pulses 1310, 1315 generated after a cardiac cycle that have different delays for individual pulses relative to the neuromodulation pulses 1305 of FIG. 13A. As shown in FIG. 13B, the neuromodulation pulses 1310 have a consistent time delay (T$_6$) for the individual stimulation pulses. As shown in FIG. 13C, the neuromodulation pulses 1315 have a time delay that initially increases, is constant, and then decreases. Specifically, the neuromodulation pulses include a first stimulation (S$_1$) after the beginning of a cardiac cycle, a second stimulation (S$_2$) after a first time delay (T$_1$), a third stimulation (S$_3$) after a second time delay (T$_2$) greater than the first time delay (T$_1$), a fourth stimulation (S$_4$) after a third time delay (T$_3$) greater than the second time delay (T$_2$), a fifth stimulation (S$_5$) after the third time delay (T$_3$), a sixth stimulation (S$_6$) after the second time delay (T$_2$), and a seventh stimulation (S$_7$) after the first time delay (T$_1$). In some embodiments, the first stimulation (S$_1$) may be delayed from the beginning of the cardiac cycle by a time delay less than the first time delay (T$_1$) and/or by a predetermined time.

Referring again to FIG. 13A, the time from the beginning of the cardiac cycle to the last stimulation or pulse can constitute a stimulation window (SW), and the time between the last stimulation or pulse and the beginning of the next cardiac cycle can constitute a non-stimulation window (NSW). The NSW can constitute a dead-zone during which no stimulation occurs regardless of patient heart rate or other conditions. In some embodiments, the SW can be limited to be less than a predetermined first period of time and/or the NSW can be at least equal to a predetermined second period of time. Limiting the SW to the first period of time and/or ensuring the NSW is at least equal to the second period of time can advantageously improve the ability to detect a subsequent R-wave (e.g., via electrical or acoustic signals). That is, by only generating and/or delivering neuromodulation pulses during the SW between cardiac cycles, the ability to detect a subsequent R-wave may be enhanced.

FIGS. 14A-14D are illustrations of waveforms 1405, 1410, 1415, 1420 (collectively referred to as "waveforms 1400") of the neuromodulation pulses generated via a patient treatment system (e.g., the system 100 (FIGS. 3, 4A, 4B)), in accordance with embodiments of the present technology. Each of the waveforms 1400 includes a stimulation portion 1430 and one or more subsequent recharge portions. Waveforms for each pulse must maintain charge balance through passive and/or active means. Charge balance maintained via passive means can rely on a blocking cap to store the outgoing energy of a pulse and then passively return it to the system in an opposite polarity. Charge balance maintained via active means can utilize biphasic waveforms.

Figures 14A, 14B, 14C, 14D:
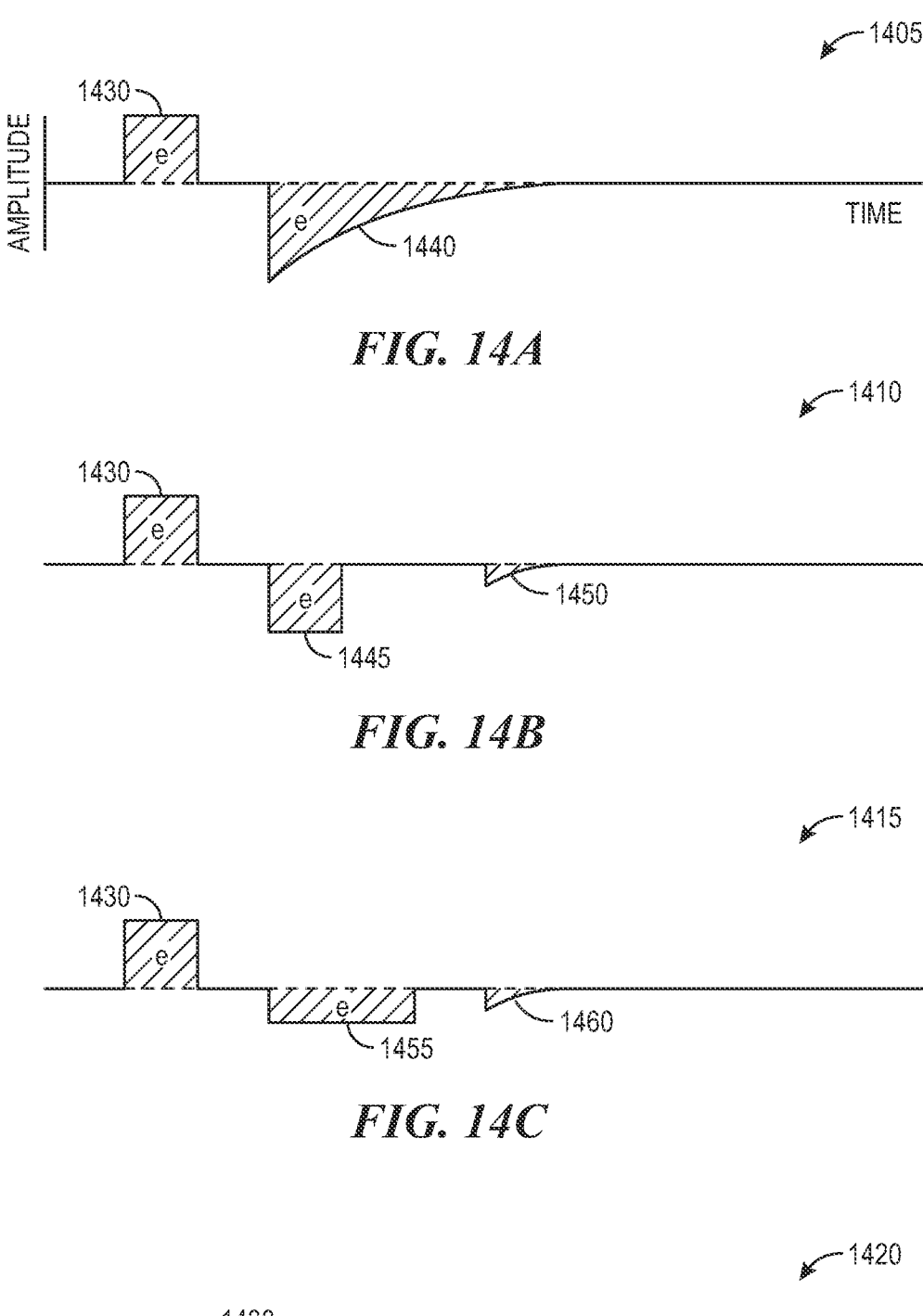
FIGS. 14A-14D are illustrations of waveforms generated via a patient treatment system, in accordance with embodiments of the present technology.

The waveforms 1400 illustrated in FIGS. 14A-14D include various charge balancing techniques. As shown in FIG. 14A, the waveform 1405 includes the stimulation portion 1430 and a passive only recharge portion 1440. As shown in FIG. 14B, the waveform 1410 is biphasic and includes the stimulation portion 1430, followed by an active recharge portion 1445 that balances at least part of the charge of the stimulation portion 1430. The area of active recharge portion 1445, equal to the amplitude multiplied by the elapsed time, is approximately equal to that of the stimulation portion 1430, and the value of the amplitude of the active recharge portion 1445 is approximately equal to that of the stimulation portion 1430. The waveform 1410 also includes, after the active recharge portion 1445, a passive recharge portion 1450, which can account for circuit tolerances. As shown in FIG. 14C, the waveform 1415 is biphasic and includes the stimulation portion 1430, followed by an active recharge portion 1455 that balances part but not all of the charge of the stimulation portion 1430. The area of active recharge portion 1455 is approximately equal to that of the stimulation portion 1430, and the value of the amplitude of the active recharge portion 1445 is less than that of the stimulation portion 1430. The waveform 1415 also includes, after the active recharge portion 1455, a passive recharge portion 1460. As shown in FIG. 14D, the waveform 1420 is triphasic and includes the stimulation portion 1430, a pre-recharge portion 1465 prior to the stimulation portion 1430, and a post-recharge portion 1470 after the stimulation portion 1430, in which the combined area of the pre- and post-recharge portions 1465, 1470 approximately equal that of the stimulation portion 1430. The value of the amplitudes of each of the pre- and post-recharge portions 1465, 1470 is less than and approximately half of that of the stimulation portion 1430. Without being bound by theory, a pre-recharge portion before a stimulation pulse can "prepare" the cells to receive the stimulation pulse for depolarization and thereby advantageously reduce the stimulation energy required to depolarize the cells. The waveform 1420 also includes, after the active recharge portion 1470, a passive recharge portion 1475.

FIG. 15 is a flow diagram of a method 1500 for stimulating a CSN of a patient, in accordance with embodiments of the present technology. The method 1500 can include providing a treatment system including a neuromodulator and a signal delivery device coupled to the neuromodulator (process portion 1502). The treatment system, neuromodulator, and signal delivery device can be or include features of the respective treatment systems (e.g., the treatment system 100 (FIGS. 3, 4A, 4B)), neuromodulators (e.g., the neuromodulator 101 (FIGS. 4A, 4B)), and signal delivery devices (e.g., the signal delivery devices 121, 521, 621, 721, 821, 921, 1021, 1121 (FIGS. 4A, 4B, 5A, 6A, 7A, and 8A-11E)) disclosed herein. As such, the signal delivery device can include a lead body (e.g., the lead bodies 125, 525, 625, 725, 825, 925, 1025, 1125 (FIGS. 4A, 4B, 5A, 6A, 7A, 8A-11E)) having a first region (e.g., the first region 530 (FIGS. 5A, 6A, 7A, 8A-11B)), a second region (e.g., the second region 540 (FIGS. 5A, 6A, 7A, 8A-11B)), and lead electrodes (e.g., the first lead electrodes 531, 931 (FIGS. 5A-10, 11B), the second lead electrodes 541, 641, 741, 941, 1041 (FIGS. 5A-10, 11B), the suture holes 833 (FIGS. 8A-10), the suture holes 843 (FIGS. 8A-10), the third lead electrode 935 (FIGS. 9 and 10), and/or the fourth lead electrode 945, 1045 (FIGS. 9 and 10)).

The method 1500 can further include implanting lead electrodes of the signal delivery device proximate to CSN afferent fibers of a patient (process portion 1504). The lead electrodes can be implanted subcutaneously in a neck region of the patient, and then moved to be proximate the CSN based on mapping data obtained via one or more of the lead electrodes, base electrodes, or other components of the patient treatment system. For example, depending on signals (e.g., electrical signals and/or acoustic signals) received via the individual lead electrodes and/or other input devices (e.g., an accelerometer and/or the other I/O devices 109 (FIG. 4A)), the position of the lead body of the signal delivery device can be adjusted until the lead electrodes are appropriately positioned proximate the CSN afferent fibers. Advantageously, utilizing features of the patient treatment system to map the patient's tissue and enable the lead electrodes to be appropriately positioned allows the signal deliver device to be implanted without dissecting nerves in the CSN area. Additionally, or alternatively, relative to implanting procedures that cannot utilize features of the patient treatment system to map to the patient's tissue, embodiments of the present technology can decrease time spent in the operating room to implant and position the signal delivery device.

The method 1500 can further include determining a physiological parameter of the patient (process portion 1506). The physiological parameter can include heart rate, augmentation index, arrhythmia, blood pressure, bioimpedance, sleep state, one or more patient-provided inputs, other measures indicative of patient activity (e.g., pulse transit time, accelerometer data, etc.), and/or cardiac depolarization (e.g., the beginning of a cardiac muscle depolarization event or cycle), and/or any other physiological parameters and/or other patient data described herein. Cardiac depolarization can be determined or sensed via corresponding signals that are carried across body tissues, which can include and/or be indicative of the associated QRS complex, R-wave, or R-R interval. The vectors formed via the base and/or lead electrodes of the patient treatment system can be used to electrically sense the cardiac muscle depolarization and/or QRS complex. For example, one of the base electrodes (e.g., the base electrodes 117A, 117B (FIGS. 4A, 4B)) and one of the lead electrodes (e.g., the lead electrodes 531, 541, 641, 741 (FIGS. 5A-7B)) can form a vector that enables cardiac depolarization to be determined. As another example, two of the base electrodes can form a vector that enables cardiac depolarization to be determined. Additionally, or alternatively to determining the physiological parameter via electrical measurement, the signals associated with cardiac depolarization can be determined via heart sounds. In such embodiments, the patient treatment system or neuromodulator can include an accelerometer or other acoustic sensor able to detect the sound signals associated with cardiac depolarization.

The physiological parameter can include bioimpedance, which can be determined or sensed via one or more sensors (e.g., electrodes) electrically coupled to one or more regions of the patient's body. In some embodiments, the sensors are positioned on and/or at least partially around the patient's chest to determine or sense a thoracic bioimpedance. The patient's thoracic bioimpedance is expected to decrease in response to increasing blood volume and increasing blood pressure. Increases to the patient's blood pressure can be driven by increases to the patient arterial blood volume, which are based at least partially on blood transfer from the patient's abdominal venous circulation to the patient's arteries, for example, during periods of exercise and/or other patient activity. Accordingly, in at least some embodiments, determining or sensing bioimpedance (e.g., thoracic bioimpedance) can be used to estimate or indicate the patient's blood pressure, which can be utilized to determine or sense the efficacy of neuromodulation pulses (process portions 1508 and 1510, described in detail below) applied to the patient to change the patient's blood pressure.

In such embodiments wherein the physiological parameter includes heart rate, blood pressure, bioimpedance, or other measures indicative of patient activity, the physiological parameter can be determined via the neuromodulator and/or signal delivery device, e.g., based on the signals that are carried across body tissues, or can be obtained from sensors (e.g., bioimpedance sensors) coupled to but separate from the neuromodulator and/or signal delivery device. In some embodiments, the physiological parameter can include other variables that are indicative of a response of the patient's arterial system. For example, the physiological parameter can include arterial stiffness, augmentation pressure, or augmentation index.

The method 1500 can further include, based on the physiological parameter, generating neuromodulation pulses (process portion 1508). As such, instead of having tonic stimulation characteristics (e.g., frequency, pulse width, amplitude, etc.) that remain unchanged through the patient therapy, embodiments of the present technology can automatically adjust the stimulation characteristics of the neuromodulation pulses based on patient activity, for example, with frequency of the neuromodulation pulses increasing as heart rate or blood pressure increases, and frequency of the neuromodulation pulses decreasing as heart rate or blood pressure decreases. Relatedly, frequency of the neuromodulation pulses can increase as the R-R interval time decreases and frequency of the neuromodulation pulses decreasing as the R-R interval time increases. Advantageously, the therapy provided to the patient, for example, in terms of the number of stimulation pulses per BPM or number of pulses per physiological parameter value, is approximately consistent and/or is not "diluted" as patient physiological parameter, heart rate, blood pressure, etc., increases.

In some embodiments, the neuromodulation pulses can include a waveform having characteristics that vary based on the physiological parameter. For example, the neuromodulation pulses can have a frequency of 0-1000 Hertz (Hz), 20-800 Hz, 200-800 Hz, 400-800 Hz, or any other incremental range therebetween (e.g., 500-650 Hz). In some embodiments, the frequency of the neuromodulation pulses can be at least 20 Hz, 100 Hz, 200 Hz, 300 Hz, 400 Hz, 500 Hz, 600 Hz, 700 Hz, 800 Hz, or 900 Hz. As described herein, the frequency or stimulation of the neuromodulation pulses can increase with heart rate or blood pressure, and/or may be greater than 1 kHz, for example, when delivered to down-regulate (e.g., block) nerve traffic.

The neuromodulation pulses can have a pulse width of 10-1000 microseconds (µs), 100-500 µs, 100-400 µs, 200-400 µs or any other incremental range therebetween (e.g., 300-350 µs). In some embodiments, the pulse width of the neuromodulation pulses can be no more than 400 µs, 350 µs, 300 µs, 250 µs, or 200 µs. As described herein (e.g., with reference FIG. 13A), the length of a cardiac cycle can be equal to the sum of an SW and an NSW, which occurs after the SW. The NSW can correspond to an end portion of each cardiac cycle and/or dead-zone during which no stimulation takes place. The lack of noise or sound generated from the patient treatment system at the end portion of a cardiac cycle can enable the patient treatment system to listen for or detect (e.g., via electrical or acoustic signals) when a subsequent cardiac depolarization event begins, which can determine when the first pulse of the neuromodulation pulses is to be delivered. In some embodiments, the pulse width or stimulation window is limited to a predetermined maximum time based on the minimum time for the non-stimulation window and the cardiac cycle.

The neuromodulation pulses can have a duty cycle of 10-75%, 25-75%, 40-60%, or any other incremental range therebetween (e.g., 50-60%). In some embodiments, the duty cycle of the neuromodulation pulses can be at least 20%, 25%, 40%, or 50%. The actual duty cycle can be based on the physiological parameter and/or other factors described herein. In some embodiments, the duty cycle can correspond to time-based on and off periods (e.g., one minute on and then one minute off), and/or a desired fraction of the SW to provide stimulation. For example, an SW of 300 milliseconds (ms) has a duty cycle of 30% at 60 BPM, 60% at 120 BPM, and 90% at 180 BPM.

As described herein (e.g., with reference to FIGS. 13A-13C), the neuromodulation pulses can include the burst of pulses that occur over a particular stimulation window and/or non-stimulation window of a cardiac cycle, and in which individual neuromodulation pulses have a predetermined delay relative to the previous neuromodulation pulse. For example, the delay of the neuromodulation pulses can increase in delay over time, such that for a single cardiac cycle each subsequent pulse is spaced apart from the previous pulse more than any prior pulse. The frequency of the individual pulses and/or the delay between adjacent pulses can be automatically adjusted by the patient treatment system, for example, based on changes to physiological parameter detected and utilized by the patient treatment system. For example, as the heart rate increases and/or the R-R interval time decreases, the frequency of the individual pulses increases (e.g., the delay between individual pulses decreases), and as the heart rate decreases and/or the R-R intervals decrease, the frequency of the individual pulses decreases (e.g., the delay between individual pulses increases). Additionally, or alternatively, the neuromodulation pulses can have characteristics that generally mimic a natural baroresponse of patients without abnormal responses. In some embodiments, neuromodulation pulses can have some individual pulses that exhibit an increased delay relative to previous pulses, and other pulses that have the same or decreased delay relative to previous pulses.

The values of physiological parameter utilized by the patient treatment system can be an average value (e.g., a rolling value averaged over the previous 30 seconds, 1 minute, etc.) and/or filtered, which can help account for extreme (e.g., very high or very low) measurements, for example, due to atrial fibrillation or other errant cardiac signals. In this regard, it is worth noting that in some embodiments, the need to constantly track the physiological parameter for instantaneous changes may not be essential, and, in addition, not instantaneously tracking the physiological parameter can help decrease energy usage of the patient treatment system.

As described herein (e.g., with reference to FIGS. 14A-14D), the waveforms of the neuromodulation pulses must maintain a charge balance. As such, the neuromodulation pulses can exhibit any of the waveforms shown and described with reference to FIGS. 14A-14D, or other waveforms that maintain the charge balance. For example, the neuromodulation pulses will alternate between a positive pulse and a negative pulse via active and/or passive means to ensure the charge balance is maintained.

As previously described, in some embodiments, the physiological parameter can include arterial stiffness, augmentation pressure or augmentation index, one or more strength-duration curves, and/or an aggregate or averaged strength-duration curve. Arterial stiffness can be an indicator of cardiovascular risk, as well as resistance of the arterial system. Augmentation pressure or augmentation index (i.e., a feature of the augmentation pressure waveform) is also a measure of arterial stiffness and is derived from the ascending aortic pressure waveform. In general, arterial stiffness will increase in response to cardiac depolarization, however, to keep blood pressure low, arterial stiffness should be kept below a predetermined threshold. As such, measuring arterial stiffness can be a helpful input for adjusting characteristics of the neuromodulation pulses. Moreover, measuring arterial stiffness can provide differing data (e.g., relative to just heart rate or blood pressure) as to the cardiovascular health of the patient, and therein the type of stimulation necessary. In such embodiments, the patient treatment system may include other I/O devices, for example, a tonometer for determining arterial stiffness, or other devices for determining an augmentation pressure waveform or index.

Relatedly, one or more strength-duration curves can also be obtained and utilized as an input to the physiological parameter used by the system to determine neuromodulation. For a given stimulation target, each strength-duration curve can measure stimulus strength (e.g., amplitude) and the duration of stimulus (e.g., pulse width). Individual ones of the strength-duration curves, and/or an aggregate or average of all or a subset of the strength-duration curves, can provide helpful data for subsequent stimulation, including (i) the rheobase which generally serves as the minimal voltage needed to bring the nerve being treated to threshold, and (ii) the chronaxie which can indicate the excitability of a nerve. Additionally, or alternatively, the strength-duration curve can be used during implantation to optimize or improve operation of the system (e.g., to determine parameters that maximize battery life, identify when increased stimulation intensity can generate increased therapeutic effects, etc.). It will be appreciated that, in at least some embodiments, there is not a fixed threshold that activates the nerve, and instead, stimulation produces a graded effect of stimulation (e.g., a dose-response relationship). Additionally, or alternatively, individual and/or aggregate strength-duration relationships can be established for one or more off-target effects, for example, to aid in avoiding producing these off-target effects.

In some embodiments, generating the neuromodulation pulses per process portion 1508 can be based on other inputs that may make the therapy more effective for the patient. For example, in some embodiments, the patient therapy system can include an accelerometer, which as previously described can be used to detect cardiac depolarization (e.g., via acoustics). Additionally, or alternatively, the accelerometer can be used to indicate patient position, patient orientation, and/or patient activity (e.g., similar to a rate-adaptive pacemaker). In such embodiments, the accelerometer can serve as a fall detector or safety mechanism, and the signal from the accelerometer can be used to adjust stimulation or characteristics of the neuromodulation pulses. For example, if the patient treatment system determines, via the signal from the accelerometer, that a patient fall may have occurred, the upper and lower frequency limits for stimulation, as explained with respect to FIG. 12, may be adjusted. Additionally, or alternatively, generating the neuromodulation pulses per process portion 1508 can be based on subjective and/or objective feedback from the patient regarding discomfort and/or other sensations experienced during therapy. For example, if the patient finds neuromodulation pulses at a first intensity to be uncomfortable, the neuromodulation pulses can be generated at a second intensity less than the first intensity to reduce or eliminate patient discomfort. In these and/or other embodiments, generating the neuromodulation pulses per process portion 1508 can be based on one or more operational limitations of the pulse generator, one or more of the electrodes, and/or patient physiology. For example, the neuromodulation pulses can be generated in accordance with one or more signal delivery parameters below the threshold at which hydrolysis occurs.

In some embodiments, generating the neuromodulation pulses per process portion 1508 can be based, at least in part, on one or more patient states. For example, in some embodiments, the neuromodulation pulses are based, at least in part, on a time of day. Some patients, such as patients with nocturnal blood pressures that are lower than their diurnal blood pressures (e.g., "dippers") may require/receive less intense therapy at various times during the night (e.g., during one or more nocturnal time periods) than during the day (e.g., during one or more diurnal time periods). Similarly, patients with nocturnal blood pressures equal to and/or greater than their day-time blood pressures (e.g., "non-dippers") may require/receive more intense therapy at various times during the night (than during the day). These dipper and non-dipper patients can be identified and differentiated based, at least in part, on data from ambulatory blood pressure monitors ("ABPM") and/or Holter monitor histories of patient nocturnal and/or diurnal blood pressure and/or heart rate, heart rate and/or other data from one or more other devices, the patient's medical history (e.g., if the patient was known to have had an early-morning myocardial infarction, a "morning surge" in blood pressure, prior stroke, arrythmias, etc.), combinations thereof, and/or other data sources described herein. The neuromodulation pulses can be generated in response to any of these and/or other data, and/or generated based on one or more predicted times of the day and/or night during which the patient is expected to have a varied state. For example, some patients may have "morning surges" and receive greater relative therapy during the morning in response.

In some embodiments, generating the neuromodulation pulses per process portion 1508 is based, at least in part, on arrhythmia and/or one or more arrhythmic events in the patient, for example, as determined based at least in part on one or more interventricular (VV) intervals and/or other detected variations in the depolarizations and/or depolarization rates of one or more chambers of the heart. In some embodiments, process portion 1508 can include reducing or discontinuing therapy, for example, for patients with bradycardia and/or syncopal patterns, and/or during periods of ventricular fibrillation ("VF"). In other embodiments, process portion 1508 can include increasing therapy, for example, during periods of atrial fibrillation ("AF"). Additionally, or alternatively, process portion 1508 can include delivering a surge of stimulation (e.g., a sustained or temporary increase in the neurostimulation intensity, frequency, amplitude, etc.) in response to detection of ventricular tachycardia (e.g., non-sustained ventricular tachycardia, couplets or triplets of premature ventricular contractions ("PVS"), etc.). In these and/or other embodiments, therapy can be escalated in response to one or more triggers, including ECG indicators of ischemia (e.g., ST segment depression or elevation, T-wave alternans ("TWA"), etc.).

The method 1500 can further include delivering the neuromodulation pulses to the CSN fibers via one or more of the lead electrodes (process portion 1510). For example, the neuromodulation pulses can be delivered to the patient via one of the lead electrodes (e.g., one of the first lead electrodes 531 (FIG. 5A)) on the first region of the lead body and one of the lead electrodes (e.g., one of the second lead electrodes 541, 641, 741 (FIGS. 5A-7B)) on the second region of the lead body. In such embodiments, the two electrodes used to deliver the stimulation pulses may be aligned with and directly across from one another when the lead body is in a closed position and/or enveloped around a target fiber of the CSN. Delivering the neuromodulation as bipolar stimulation can decrease the energy requirement for stimulation, relative to monopolar stimulation. Additionally, as described with reference to FIGS. 6A-7B, for those embodiments including a first region with five lead electrodes and a second region with less than five electrodes (e.g., three electrodes or one electrode), but that cover a similar or identical footprint, can further decrease the energy requirement for stimulation without limiting selectivity or the ability to target particular target fibers between the first and second regions of the lead body.

In some embodiments, delivering the neuromodulation pulses to the CSN fibers via one or more of the lead electrodes (process portion 1510) further includes delivering one or more first neuromodulation pulses to the CSN fibers and one or more second neuromodulation pulses to additional tissues of the patient. Individual ones of the first neuromodulation pulses can have first signal delivery parameters (e.g., frequency, amplitude, pulse width, etc.), and individual ones of the second neuromodulation pulses can have second signal delivery parameters (e.g., frequency, amplitude, pulse width, etc.) that are the same as or different than corresponding ones of the first signal delivery parameters. The additional tissues of the patient can include one or more nerves and/or muscles, including the muscles innervated by the nerves described herein, and can be selected to provide a same or different physiologic and/or therapeutic effect as provided by delivering the neuromodulation pulses to the CSN fibers. In at least some embodiments, for example, the first neuromodulation pulses are delivered to the CSN fibers (e.g., to reduce the patient's blood pressure, as described previously herein), and the second neuromodulation pulses are delivered to the hypoglossal nerve and/or the ansa cervicalis nerve to, for example, address or treat the patient's obstructive sleep apnea (OSA). Additionally, or alternatively, the second neuromodulation pulses can be delivered to one or both of the atria and/or one or both of the ventricles of the patient's heart (e.g., to prevent, or at least partially prevent, arrythmia). For example, the second neuromodulation pulses can be cardiac resynchronization pulses delivered to at least partially or fully resynchronize depolarization of various portions of the patient's heart. In some embodiments, the second neuromodulation pulses can be delivered along with complementary and/or synergistic CSN stimulation (e.g., to reduce ventricular load while resynchronizing the patient's heart). In these and other embodiments, the second neuromodulation pulses can be delivered by the same device and/or another neuromodulation device to address or treat other indications, including heart failure, OSA, central sleep apnea, etc. For example, delivering the second neuromodulation pulses can include delivering the second neuromodulation pulses to address or treat heart failure (e.g., heart failure with preserved ejection fraction and/or heart failure with reduced ejection fraction), to provide cardiac resynchronization therapy, to provide cardiac contractility modulation therapy, to stimulate the patient's diaphragm to address or treat central sleep apnea, etc.

Process portions of the method 1500 can be iteratively performed and utilize feedback from the system in a closed-loop manner. For example, process portions 1506, 1508, 1510 can be performed multiple times for a given therapy session. That is, after delivering the neuromodulation pulses to the CSN afferent fibers (process portion 1510), the method 1500 can determine an updated physiological parameter of the patient (process portion 1506), and generate additional neuromodulation pulses based on the update physiological parameter (process portion 1508). It is worth noting that the physiological parameters determined after delivering the initial neuromodulation pulses are in part reactions to the initial neuromodulation pulses and are thus an indicator of the effect of the initial neuromodulation pulses. As such, the iteration of the process portions 1506, 1508, 1510 helps provide more effective patient therapy that can improve with each iteration, while still providing therapy responsive to patient activity (e.g., based on the physiological parameter) and that is thus non-dilutive.

FIG. 16 is a flow diagram of a method 1600 for stimulating nerve fibers (e.g., a CSN) of a patient, in accordance with embodiments of the present technology. The method 1600 can include providing a treatment system including a neuromodulator and a signal delivery device coupled to the neuromodulator (process portion 1602). The treatment system, neuromodulator, and signal delivery device can be or include features of the respective treatment systems (e.g., the treatment system 100 (FIGS. 4A, 4B)), neuromodulators (e.g., the neuromodulator 101 (FIGS. 4A, 4B)), and signal delivery devices (e.g., the signal delivery devices 121, 521, 621, 721, 821, 921, 1021, 1121 (FIGS. 4A, 4B, 5A, 6A, 7A, 8A-10, 11A-11E)) described herein. As such, the signal delivery device can include a lead body (e.g., the lead bodies 125, 525, 625, 725, 825, 925, 1025, 1125 (FIGS. 4A, 4B, 5A, 6A, 7A, 8A-111B)) having a first region (e.g., the first region 530 (FIGS. 5A, 6A, 7A, 8A-10, 11B)), a second region (e.g., the second region 540 (FIGS. 5A, 6A, 7A, 8A-10, 11B)), and lead electrodes (e.g., the first lead electrodes 531, 931 (FIGS. 5A-10, 11B), the second lead electrodes 541, 641, 741, 941, 1041 (FIGS. 5A-10, 11B), the suture holes 833 (FIGS. 8A-10), the suture holes 843 (FIGS. 8A-10), the third lead electrode 935 (FIGS. 9 and 10), and/or the fourth lead electrode 945, 1045 (FIGS. 9 and 10)).

The method 1600 can further include implanting lead electrodes of the signal delivery device within a patient (process portion 1604). For example, the lead electrodes can be implanted subcutaneously in a neck region of the patient.

In some embodiments, implanting the lead electrodes includes dissecting the patient's tissue at or near the neck region, for example, at least proximate to and/or aligned with a location at which the lead electrodes are to be implanted. In these and/or other embodiments, implanting the lead electrodes can include pre-mapping one or more tissues in the neck region to identify target tissue, for example, by providing electrical stimulation and observing and/or detecting the patient's response to the electrical stimulation. Additionally, or alternatively, image techniques (e.g., ultrasound, OCT, infrared, etc.) can be used to identify the target tissue. These and/or other techniques can also be used to identify non-target tissue (e.g., patient tissue that should not receive electrical stimulation). For example, the lead electrodes or another signal delivery device can be used to stimulate one or more nerves and/or other tissue in the vicinity of the target tissue to find a pathway for coughing and/or other off-target effects, and the lead electrodes can be positioned or repositioned to avoid stimulating that area and/or otherwise reducing or preventing producing off-target effects during stimulation. Additionally, or alternatively, ice or other cryogenic sink (e.g., a closed container of circulating, chilled alcohol) can be positioned at or near a tissue to reduce or eliminate extraneous stimulation intraoperatively, and then the lead electrodes can be positioned or repositioned to avoid or dissect the tissue if it is identified as a redundant or accessory pathway, superior to the tissue of off-target effect fibers known to diverge superiorly, etc.

The method 1600 can further include delivering first neuromodulation pulses to nerve fibers (e.g., afferent nerve fibers, CSN afferent fibers, efferent nerve fibers, etc.) of the patient via one or more of the lead electrodes according to first stimulation parameters. The first stimulation parameters can include a first frequency, first amplitude, first pulse width, first duty cycle, and/or first lead electrode configuration (e.g., a first group (e.g., two or more) of electrodes). The first frequency, first amplitude, first pulse width, and first duty cycle can include any of the respective frequencies, amplitudes, pulse widths, and duty cycles described herein, and the first lead electrode configuration can include any combination of the lead electrodes described herein.

The method 1600 can further include sensing, via a vector of the treatment system, a parameter, such as a parameter associated with a cardiac depolarization event (process portion 1608). The parameter of process portion 1608 can include any of the physiological parameters described herein, e.g., with reference to the method 1500 or process portion 1506. As described herein, the base electrodes and/or lead electrodes can form various vectors, which can serve as a sensing channel for detecting signals (e.g., electrical signals and/or acoustic signals). Each of the lead electrodes is individually addressable and electrically coupled to one or both of the base electrodes. As such, the vectors can include any one of the base electrodes and any one of the lead electrodes. Additionally, the vectors can include the two base electrodes, which are spaced apart from one another by a minimum distance (as described with reference to FIGS. 4A and 4B) and none of the lead electrodes. For embodiments in which the parameter is associated with the cardiac depolarization event, the parameter can include the beginning of a cardiac depolarization event, which can define timing for delivering the initial pulse of the neuromodulation pulses, and/or the R-R interval. In some embodiments, the patient treatment system can include other input devices (e.g., an accelerometer and/or the I/O devices 109 (FIG.

4A)) to provide additional ability to sense the parameter, in addition to the sensing provided via the base electrodes and lead electrodes.

The method 1600 can further comprise, based on the sensed parameter, adjusting one or more of the first stimulation parameters to define second stimulation parameters (process portion 1610). Adjusting one or more of the stimulation parameters can include (i) adjusting (e.g., increasing or decreasing) an intensity of the stimulation, for example, by adjusting one or more of the frequency, amplitude, pulse width, and/or duty cycle (or another parameter) of the neuromodulation pulses used to stimulate the patient, and/or (ii) adjusting an electrode configuration (e.g., electronic repositioning) for delivering neuromodulation pulses to the nerve fibers of the patient. For example, based on the sensed parameter, adjusting the electrode configuration can include altering the group of lead electrodes used to deliver the neuromodulation pulses such that a different group of electrodes is used to deliver the stimulation to the nerve fibers. For example, if a first group of lead electrodes was used to stimulate the nerve fibers (per process portion 1606), based on the sensed parameter (per process portion 1608), a second group of lead electrodes can be used to subsequently stimulate the nerve fibers. The second group of lead electrodes can include at least one lead electrode that is different than the first group of lead electrodes. In some embodiments, adjusting one or more of the first stimulation parameters includes adjusting (i) the electrode configuration for delivering neuromodulation pulses to the nerve fibers of the patient, and (ii) one or more of the frequency, amplitude, pulse width, and duty cycle of the neuromodulation pulses.

The method 1600 can further comprise delivering second neuromodulation pulses to the nerve fibers of the patient via one or more of the lead electrodes according to the second stimulation parameters. The second neuromodulation pulses can include a different frequency, amplitude, pulse width, duty cycle, and/or electrode configuration relative to the respective frequency, amplitude, pulse width, duty cycle, and electrode configuration of the first neuromodulation pulses.

The method 1600, or specifically, process portions 1608 and 1610, can be iteratively repeated and adjusted in a closed-loop manner to determine a preferred group (e.g., a pair or two or more) of the lead electrodes proximate to the CSN afferent fibers. For example, each sensed parameter associated with the cardiac depolarization event may cause the stimulation parameters to be adjusted to provide improved stimulation via the signal delivery device to the nerve fibers. For example, two or more rounds of sensing the parameter may be needed before the ideal stimulation parameter(s) are determined. As such, each cardiac depolarization can provide additional data, obtained via the vectors of the patient therapy system, that can be utilized to improve the therapy or stimulation provided via the lead electrodes to the nerve fibers (e.g., the CSN).

In some embodiments, the sensed parameter can also be used to effectively map (e.g., intraoperatively map) the tissue of the patient, relative to the CSN afferent fibers, while the lead electrodes are implanted (per process portion 1604). Advantageously, utilizing features of the patient treatment system to map the patient's tissue can enable the lead electrodes to be appropriately positioned, thereby allowing the signal delivery device to be implanted without dissecting nerves in the CSN area. Additionally, or alternatively, relative to implant procedures that cannot utilize features of the patient treatment system to map to the patient's tissue, embodiments of the present technology can decrease time spent in the operating room to implant and position the signal delivery device.

IV. Conclusion

It will be apparent to those having skill in the art that changes may be made to the details of the above-described embodiments without departing from the underlying principles of the present disclosure. In some cases, well known structures and functions have not been shown or described in detail to avoid unnecessarily obscuring the description of the embodiments of the present technology. Although steps of methods may be presented herein in a particular order, alternative embodiments may perform the steps in a different order. Similarly, certain aspects of the present technology disclosed in the context of particular embodiments can be combined or eliminated in other embodiments. Furthermore, while advantages associated with certain embodiments of the present technology may have been disclosed in the context of those embodiments, other embodiments can also exhibit such advantages, and not all embodiments need necessarily exhibit such advantages or other advantages disclosed herein to fall within the scope of the technology. Accordingly, the disclosure and associated technology can encompass other embodiments not expressly shown or described herein, and the invention is not limited except as by the appended claims.

Throughout this disclosure, the singular terms "a," "an," and "the" include plural referents unless the context clearly indicates otherwise. Additionally, the term "comprising," "including," and "having" should be interpreted to mean including at least the recited feature(s) such that any greater number of the same feature and/or additional types of other features are not precluded.

Reference herein to "one embodiment," "an embodiment," "some embodiments," or similar formulations means that a particular feature, structure, operation, or characteristic described in connection with the embodiment can be included in at least one embodiment of the present technology. Thus, the appearances of such phrases or formulations herein are not necessarily all referring to the same embodiment. Furthermore, various particular features, structures, operations, or characteristics may be combined in any suitable manner in one or more embodiments.

Unless otherwise indicated, all numbers expressing pressures, frequencies, amplitudes, duty cycles, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present technology. At the very least, and not as an attempt to limit the application of the doctrine of equivalents to the scope of the claims, each numerical parameter should at least be construed in light of the number of reported significant digits and by applying ordinary rounding techniques. Additionally, all ranges disclosed herein are to be understood to encompass any and all subranges subsumed therein. For example, a range of "1 to 10" includes any and all subranges between (and including) the minimum value of 1 and the maximum value of 10 (i.e., any and all subranges having a minimum value of equal to or greater than 1 and a maximum value of equal to or less than 10 (e.g., 5.5 to 10)).

The disclosure set forth above is not to be interpreted as reflecting an intention that any claim requires more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

The present technology is illustrated, for example, according to various aspects described below as numbered clauses (1, 2, 3, etc.) for convenience. These are provided as examples and do not limit the present technology. It is noted that any of the dependent clauses may be combined in any combination, and placed into a respective independent clause.

1. A patient treatment system, comprising:
   a neuromodulator comprising a housing, and at least one base electrode carried by the housing;
   an implantable signal delivery device electrically coupleable to the neuromodulator, the signal delivery device comprising a lead body including a first region, a second region positionable over the first region, and lead electrodes electrically coupleable to the base electrode of the neuromodulator, wherein the lead electrodes are configured to be implanted proximate to and/or at least partially around one or more nerves associated with a baroreflex of a patient;
   one or more processors; and
   tangible, non-transitory, computer-readable media having instructions that, when executed by the one or more processors, cause the patient treatment system to perform operations comprising:
      obtaining a physiological parameter of the patient;
      based on the obtained physiological parameter, generating neuromodulation pulses; and
      delivering the neuromodulation pulses to the carotid sinus nerve (CSN) afferent fibers via one or more of the lead electrodes.

2. The patient treatment system of any one of the clauses herein, wherein the one or more nerves include CSN afferent fibers of the patient.

3. The patient treatment system of any one of the clauses herein, wherein the lead electrodes include a first set of lead electrodes at the first region and a second set of lead electrodes at the second region.

4. The patient treatment system of any one of the clauses herein, wherein the lead electrodes are all on the first region.

5. The patient treatment system of any one of the clauses herein, wherein the lead electrodes include at least three, four, five, six, seven, eight, nine, or ten lead electrodes.

6. The patient treatment system of any one of the clauses herein, wherein the lead electrodes include a first set of lead electrodes at the first region and a second set of lead electrodes at the second region, and wherein the number of lead electrodes of the first set of lead electrodes is different than the number of lead electrodes of the second set of lead electrodes.

7. The patient treatment system of any one of the clauses herein, wherein the lead electrodes include a first set of lead electrodes at the first region and a second set of lead electrodes at the second region, and wherein the number of lead electrodes of the first set of lead electrodes is more than the number of lead electrodes of the second set of lead electrodes.

8. The patient treatment system of any one of the clauses herein, wherein the lead electrodes include a first set of lead electrodes at the first region and a second set of lead electrodes at the second region, and wherein the first set of lead electrodes includes at least two lead electrodes and the second set of lead electrodes includes only a single lead electrode.

9. The patient treatment system of any one of the clauses herein, wherein the lead electrodes include a first set of lead electrodes at the first region and a second set of lead electrodes at the second region, wherein the first set of lead electrodes includes at least three lead electrodes and the second set of lead electrodes includes at least three lead electrodes, and wherein, when the first region is positioned over the second region, each of the first set of lead electrodes aligns with a corresponding one of the second set of lead electrodes.

10. The patient treatment system of any one of the clauses herein, wherein the lead electrodes include a first set of lead electrodes at the first region and a second set of lead electrodes at the second region, wherein the first set of lead electrodes includes at least three lead electrodes spanning across a first width and the second set of lead electrodes includes at least one lead electrode spanning across a second width equal to the first width, and wherein, when the first region is positioned over the second region, the three lead electrodes of the first set of lead electrodes aligns with the one lead electrode of the second set of lead electrodes.

11. The patient treatment system of any one of the clauses herein, wherein the lead electrodes include a first set of lead electrodes at the first region and a second set of lead electrodes at the second region, and wherein the first set of electrodes are configured to be positioned over a first side of the CSN afferent fibers and the second set of electrodes are configured to be positioned over a second side of the CSN afferent fibers opposite the first side.

12. The patient treatment system of any one of the clauses herein, wherein individual lead electrodes have a different width than other individual electrodes.

13. The patient treatment system of any one of the clauses herein, wherein the lead electrodes include a first set of lead electrodes at the first region and a second set of lead electrodes at the second region, and wherein the first set of lead electrodes and the second set of electrodes each spans across an identical width.

14. The patient treatment system of any one of the clauses herein, wherein the lead electrodes include a first set of lead electrodes at the first region and each spaced apart from one another in a first direction, a second set of lead electrodes at the second region and each spaced apart from one another in the first direction, a third electrode at the first region and spaced apart from the first set of lead electrodes along a second direction normal to the first direction, and a fourth electrode at the second region and spaced apart from the second set of lead electrodes along the second direction, wherein, when the first region is positioned over the second region, the third electrode at least partially aligns with the fourth electrode.

15. The patient treatment system of any one of the clauses herein, wherein the lead electrodes include a first set of lead electrodes at the first region and each spaced apart from one another in a first direction, a second set of lead electrodes at the second region and each spaced apart from one another in the first direction, a third electrode at the first region and spaced apart from the first set of lead electrodes along a second direction normal to the first direction, and a fourth electrode at the second region and spaced apart from the second set of lead electrodes along the second direction, wherein, when the first region is positioned over the second region, the third electrode at least partially aligns with the second set of lead electrodes and the fourth electrode at least partially aligns with the first set of lead electrodes.

16. The patient treatment system of any one of the clauses herein, wherein the lead electrodes include a first set of lead electrodes at the first region and each spaced apart from one another in a first direction, a second set of lead electrodes at the second region and each spaced apart from one another in the first direction, a third electrode at the first region and spaced apart from the first set of lead electrodes along a second direction normal to the first direction, and a fourth electrode at the second region and spaced apart from the second set of lead electrodes along the second direction, wherein the first set of lead electrodes and the third electrode span the same width.

17. The patient treatment system of any one of the clauses herein, wherein the lead electrodes include a first set of lead electrodes at the first region and a second set of lead electrodes at the second region, and wherein the first set of electrodes are configured to be positioned over a first side of the CSN afferent fibers and the second set of electrodes are configured to be positioned over a second side of the CSN afferent fibers opposite the first side.

18. The patient treatment system of any one of the clauses herein, wherein the lead electrodes include a first set of lead electrodes at the first region and a second set of lead electrodes at the second region, and wherein each of the first set of lead electrodes has a first width and at least one of the second set of lead electrodes has a second width greater than the first width.

19. The patient treatment system of any one of the clauses herein, wherein each of the lead electrodes are individually addressable via the neuromodulator.

20. The patient treatment system of any one of the clauses herein, wherein:

the signal delivery device includes conductors extending from the housing to the lead body, the at least one base electrode is a first base electrode and the neuromodulator includes a second base electrode spaced apart from the first base electrode, and each of the conductors are electrically coupled to (i) one of the first base electrode or the second base electrode, and (ii) one of the lead electrodes.

21. The patient treatment system of any one of the clauses herein, wherein the obtained physiological parameter is indicative of cardiac muscle depolarization.

22. The patient treatment system of any one of the clauses herein, wherein the obtained physiological parameter comprises heart rate, and wherein delivering the neuromodulation pulses comprises delivering the neuromodulation pulses at a stimulation rate that is correlated with the determined physiological parameter, such that a higher value of the determined physiological parameter corresponds to a higher value of the stimulation rate.

23. The patient treatment system of any one of the clauses herein, wherein delivering the neuromodulation pulses comprises delivering the neuromodulation pulses at a frequency, amplitude, and pulse width that is directly correlated with the determined physiological parameter, such that a higher value of the determined physiological parameter corresponds to a higher value of the frequency, amplitude, and/or pulse width.

24. The patient treatment system of any one of the clauses herein, wherein delivering the neuromodulation pulses comprises delivering the neuromodulation pulses at a frequency, amplitude, and/or pulse width that is indirectly related to the determined physiological parameter, such that a higher value of the determined physiological parameter corresponds to a lower value of the frequency, amplitude, and/or pulse width.

25. The patient treatment system of any one of the clauses herein, wherein the neuromodulation pulses are delivered via a set of the lead electrodes, and wherein delivering the neuromodulation pulses comprises changing at least one of the lead electrodes forming the set after delivering a predetermined number of pulses.

26. The patient treatment system of any one of the clauses herein, wherein the neuromodulation pulses are delivered via a set of the lead electrodes, and wherein delivering the neuromodulation pulses comprises changing at least one of the lead electrodes forming the set after delivering a first pulse.

27. The patient treatment system of any one of the clauses herein, wherein the neuromodulation pulses are delivered via a set of the lead electrodes, and wherein delivering the neuromodulation pulses comprises changing at least one of the lead electrodes forming the set after delivering 2,400 pulses.

28. The patient treatment system of any one of the clauses herein, wherein the obtained physiological parameter comprises a first heart rate and delivering the neuromodulation pulses comprises delivering first neuromodulation pulses at a first frequency, the operations further comprising:

determining a second heart rate; and based on the second heart rate, delivering second neuromodulation pulses at a second frequency higher than the first frequency.

29. The patient treatment system of any one of the clauses herein, wherein the neuromodulation pulses have a frequency that varies linearly with the obtained physiological parameter.

30. The patient treatment system of any one of the clauses herein, wherein the neuromodulation pulses have a frequency that varies non-linearly with the obtained physiological parameter.

31. The patient treatment system of any one of the clauses herein, wherein the neuromodulation pulses have a frequency that varies exponentially with the obtained physiological parameter.

32. The patient treatment system of any one of the clauses herein, wherein the neuromodulation pulses have a frequency between a predetermined lower frequency and a predetermined upper frequency.

33. The patient treatment system of any one of the clauses herein, wherein delivering the neuromodulation pulses includes delivering the neuromodulation pulses via one or more of the lead electrodes at the first region and one or more of the lead electrodes at the second region.

34. The patient treatment system of any one of the clauses herein, wherein the lead electrodes include a first set of lead electrodes at the first region and a second set of lead electrodes at the second region, the operations further comprising obtaining impedance data via two or more of the lead electrodes, wherein delivering the neuromodulation pulses comprises, based on the obtained impedance data, delivering the neuromodulation pulses via a first lead electrode of the first set of lead electrodes and a second lead electrode of the second set of lead electrodes.

35. The patient treatment system of any one of the clauses herein, the operations further comprising, prior to generating the neuromodulation pulses, identifying the CSN afferent fibers via the lead electrodes of the signal delivery device.

36. The patient treatment system of clause 35, wherein identifying the CSN afferent fibers comprises obtaining data from the lead electrodes, the data comprising an amount of energy and wherein delivering the neuromodulation pulses comprises, based on the obtained data, delivering the neuromodulation pulses via one of the lead electrodes and a second lead electrode of the second set of lead electrodes.

37. The patient treatment system of clause 35, wherein the lead electrodes include a first set of lead electrodes at the first region and a second set of lead electrodes at the second region, and wherein identifying the CSN afferent fibers comprises obtaining impedance data from at least one of the first set of lead electrodes and at least one of the second set of lead electrodes, and wherein delivering the neuromodulation pulses comprises, based on the obtained impedance data, delivering the neuromodulation pulses via a first lead electrode of the first set of lead electrodes and a second lead electrode of the second set of lead electrodes.

38. The patient treatment system of any one of the clauses herein, wherein the lead electrodes include a first set of lead electrodes at the first region and a second set of lead electrodes at the second region, and wherein delivering the neuromodulation pulses comprises delivering the neuromodulation pulses via a first lead electrode of the first set of lead electrodes and a second lead electrode of the second set of lead electrodes, the operations further comprising:

obtaining a signal based on impedance data from at least one of the first lead electrode or the second lead electrode; and based on the signal being above a predetermined threshold, delivering the first set of pulses via (i) one of the lead electrodes at the first region other than the first lead electrode, and (ii) one of the lead electrodes at the second region other than the second lead electrode.

39. The patient treatment system of any one of the clauses herein, wherein the neuromodulation pulses have a pulse width of 10-1000 microseconds.

40. The patient treatment system of any one of the clauses herein, wherein the neuromodulation pulses have a duty cycle of no more than 50%.

41. The patient treatment system of any one of the clauses herein, wherein the neuromodulation pulses have an amplitude of 0-10 mA.

42. The patient treatment system of any one of the clauses herein, wherein the neuromodulation pulses have a frequency of 0-1000 Hz.

43. The patient treatment system of any one of the clauses herein, wherein individual pulses of the neuromodulation pulses have a delay relative to the preceding pulse that increases over time.

44. The patient treatment system of any one of the clauses herein, wherein the neuromodulation pulses include a first pulse having a first delay from an immediately preceding pulse, and a second pulse having a second delay from an immediately preceding pulse, wherein the second delay is longer than the first delay.

45. The patient treatment system of any one of the clauses herein, wherein the neuromodulation pulses include a first pulse having a first delay from an immediately preceding pulse, a second pulse having a second delay from an immediately preceding pulse, and a third pulse having a third delay from an immediately preceding pulse, wherein the third delay is longer than the second delay and the second delay is longer than the first delay.

46. The patient treatment system of any one of the clauses herein, wherein the neuromodulation pulses include a first number of pulses that have a first delay, a second number of pulses that have a second delay greater than the first delay, and a third number of pulses that have a third delay greater than the second delay.

47. The patient treatment system of any one of the clauses herein, wherein the neuromodulation pulses include a first number of pulses that have a first delay, a second number of pulses that have a second delay greater than the first delay, and a third number of pulses that have a third delay less than the second delay and the first delay.

48. The patient treatment system of any one of the clauses herein, wherein individual pulses of the neuromodulation pulses include a delay that generally corresponds to a natural baroresponse of the patient.

49. The patient treatment system of any one of the clauses herein, wherein the obtained physiological parameter includes instantaneous heart rate or an average heart rate.

50. The patient treatment system of any one of the clauses herein, wherein the obtained physiological parameter includes a blood pressure or an average blood pressure.

51. The patient treatment system of any one of the clauses herein, wherein the obtained physiological parameter includes bioimpedance.

52. The patient treatment system of any one of the clauses herein, wherein the obtained physiological parameter includes thoracic bioimpedance.

53. The patient treatment system of any one of the clauses herein, wherein the obtained physiological parameter includes an activity level of the patient.

54. The patient treatment system of any one of the clauses herein, further comprising a blood pressure sensor coupled to a neuromodulator and configured to generate blood pressure data, wherein generating the neuromodulation pulses is based at least in part on the blood pressure data.

55. The patient treatment system of any one of the clauses herein, further comprising a blood pressure sensor coupled to the neuromodulator and configured to generate data comprising at least one of blood pressure, diastolic blood pressure, or systolic blood pressure.

56. The patient treatment system of any one of the clauses herein, further comprising one or more sensors coupled to the neuromodulator and configured to generate data comprising at least one of stroke volume, cardiac output, ventricular end diastolic volume, or ventricular end systolic volume.

57. The patient treatment system of any one of the clauses herein, further comprising an oxygenation sensor coupled to the neuromodulator and configured to generate data comprising blood oxygenation.

58. The patient treatment system of any one of the clauses herein, further comprising a tonometer coupled to the neuromodulator and configured to generate data comprising arterial stiffness.

59. The patient treatment system of any one of the clauses herein, further comprising one or more sensors communicatively coupled to the neuromodulator via a wireless or wired connection.

60. The patient treatment system of any one of the clauses herein, further comprising one or more sensors implanted within the patient and communicatively coupled to the neuromodulator.

61. The patient treatment system of any one of the clauses herein, further comprising one or more sensors positioned external to the patient and communicatively coupled to the neuromodulator.

62. The patient treatment system of any one of the clauses herein, wherein the base electrode is a first base electrode and the neuromodulator comprises a second base electrode spaced apart from the first base electrode, wherein the neuromodulator includes a header comprising the first base electrode and the second base electrode.

63. The patient treatment system of any one of the clauses herein, wherein the neuromodulator comprises the tangible, non-transitory, computer-readable media.

64. The patient treatment system of any one of the clauses herein, further comprising a controller comprising the tangible, non-transitory, computer-readable media, wherein the controller is in wired or wireless communication with the neuromodulator.

65. The patient treatment system of any one of the clauses herein, further comprising an acoustic sensor configured to detect cardiac depolarization, wherein generating the neuromodulation pulses is based in part on a signal from the acoustic sensor.

66. The patient treatment system of any one of the clauses herein, further comprising an accelerometer configured to detect cardiac depolarization, wherein generating the neuromodulation pulses is based in part on a signal from the accelerometer.

67. The patient treatment system of any one of the clauses herein, further comprising an accelerometer configured to output a signal comprising orientation of the patient, wherein generating the neuromodulation pulses is based in part on the signal from the accelerometer.

68. The patient treatment system of any one of the clauses herein, wherein the neuromodulation pulses are first neuromodulation pulses, the operations further comprising delivering second neuromodulation pulses to another target tissue of a patient different than the CSN afferent fibers.

69. The patient treatment system of any one of the clauses herein, wherein the neuromodulation pulses are first neuromodulation pulses, the operations further comprising delivering second neuromodulation pulses to a hypoglossal nerve of the patient.

70. The patient treatment system of any one of the clauses herein, wherein the neuromodulation pulses are first neuromodulation pulses, the operations further comprising delivering second neuromodulation pulses to an ansa cervicalis nerve of the patient.

71. The patient treatment system of any one of the clauses herein, wherein the neuromodulation pulses are first neuromodulation pulses, the operations further comprising delivering second neuromodulation pulses to a vagus nerve of the patient.

72. The patient treatment system of any one of the clauses herein, wherein the neuromodulation pulses are first pulses, the operations further comprising delivering second pulses to a left or right atria of the patient.

73. The patient treatment system of any one of the clauses herein, wherein the neuromodulation pulses are first pulses, the operations further comprising delivering second pulses to a left or right ventricle of the patient.

74. The patient treatment system of any one of the clauses herein, wherein the neuromodulation pulses are first pulses, the operations further comprising delivering second pulses to a diaphragm of the patient.

75. A method for configuring a treatment system to stimulate CSN afferent fibers, the method comprising:
providing a treatment system including a neuromodulator and a signal delivery device electrically coupled to the neuromodulator;
implanting lead electrodes of the signal delivery device proximate to CSN afferent fibers of a patient;
determining a physiological parameter of the patient;
based on the determined physiological parameter, generating, via the neuromodulator, neuromodulation pulses; and
delivering the neuromodulation pulses to the CSN afferent fibers via two or more of the lead electrodes.

76. The method of any one of the clauses herein, wherein the treatment system comprises the treatment system of any one of the previous clauses.

77. The method of any one of the clauses herein, further comprising a neuromodulator including the pulse generator and the signal delivery device, wherein:
the neuromodulator comprises a housing, and at least one base electrode carried by the housing,
the signal delivery device comprises a lead body including a first region and a second region positionable over the first region,
the lead electrodes of the signal delivery device are electrically coupled to the base electrode of the neuromodulator,
the lead electrodes include a first set of lead electrodes at the first region and a second set of lead electrodes at the second region, and
delivery of the neuromodulation pulses comprises delivering the neuromodulation pulses via one of the first set of electrodes and one of the second set of electrodes.

78. The method of any one of the clauses herein, wherein the determined physiological parameter comprises heart rate, and wherein delivering the neuromodulation pulses comprises delivering the neuromodulation pulses at a frequency that is directly or indirectly correlated with the determined physiological parameter, such that a higher value of the determined physiological parameter corresponds to a higher value of the frequency.

79. The method of any one of the clauses herein, wherein the determined physiological parameter comprises a first heart rate and delivering the neuromodulation pulses comprises delivering first neuromodulation pulses at a first frequency, the operations further comprising:
determining a second heart rate; and
based on the second heart rate, delivering second neuromodulation pulses at a second frequency different than the first frequency.

80. The method of any one of the clauses herein, wherein delivering the neuromodulation pulses comprises delivering the neuromodulation pulses such that individual pulses have a frequency that varies linearly with the determined physiological parameter.

81. The method of any one of the clauses herein, wherein delivering the neuromodulation pulses comprises delivering the neuromodulation pulses such that individual pulses have a frequency that varies non-linearly with the determined physiological parameter.

82. The method of any one of the clauses herein, wherein delivering the neuromodulation pulses comprises delivering the neuromodulation pulses such that individual pulses have a frequency that varies exponentially with the determined physiological parameter.

83. The method of any one of the clauses herein, further comprising obtaining impedance data via two or more of the lead electrodes, wherein delivering the neuromodulation pulses comprises, based on the obtained impedance data, delivering the neuromodulation pulses via a first lead electrode of the first set of lead electrodes and a second lead electrode of the second set of lead electrodes.

84. The method of any one of the clauses herein, further comprising, prior to generating the neuromodulation pulses, identifying the CSN afferent fibers via the lead electrodes of the signal delivery device.

85. The method of any one of the clauses herein, further comprising, prior to generating the neuromodulation pulses, identifying the CSN afferent fibers via the lead electrodes of the signal delivery device wherein identifying the CSN afferent fibers comprises obtaining impedance data from at least one of the first set of lead electrodes and at least one of the second set of lead electrodes, and wherein delivering the neuromodulation pulses comprises, based on the obtained impedance data, delivering the neuromodulation pulses via a first lead electrode of the first set of lead electrodes and a second lead electrode of the second set of lead electrodes.

86. The method of any one of the clauses herein, wherein delivering the neuromodulation pulses comprises delivering the neuromodulation pulses via a first lead electrode of the first set of lead electrodes and a second lead electrode of the second set of lead electrodes, the method further comprising:

obtaining a signal based on impedance data from at least one of the first lead electrode or the second lead electrode; and based on the signal being above a predetermined threshold, delivering the first set of pulses via (i) another lead electrode on the first region other than the first lead electrode, and (ii) another lead electrode on the second region other than the second lead electrode.

87. The method of any one of the clauses herein, wherein individual pulses of the neuromodulation pulses have a delay relative to the preceding pulse that increases over time.

88. The method of any one of the clauses herein, wherein individual pulses of the neuromodulation pulses have a delay relative to the preceding pulse that decreases over time.

89. The method of any one of the clauses herein, wherein the neuromodulation pulses includes a first pulse having a first delay from an immediately preceding pulse, and a second pulse having a second delay from an immediately preceding pulse, wherein the second delay is longer than the first delay.

90. The method of any one of the clauses herein, wherein the neuromodulation pulses includes a first pulse having a first delay from an immediately preceding pulse, a second pulse having a second delay from an immediately preceding pulse, and a third pulse having a third delay from an immediately preceding pulse, wherein the third delay is longer than the second delay and the second delay is longer than the first delay.

91. The method of any one of the clauses herein, wherein the neuromodulation pulses includes a first number of pulses that have a first delay, a second number of pulses that have a second delay greater than the first delay, and a third number of pulses that have a third delay greater than the second delay.

92. The method of any one of the clauses herein, wherein individual pulses of the neuromodulation pulses include a delay that generally corresponds to a natural baroresponse of the patient.

93. The method of any one of the clauses herein, wherein the determined physiological parameter includes an instantaneous heart rate, a filtered heart rate, or an average heart rate.

94. The method of any one of the clauses herein, wherein the determined physiological parameter includes instantaneous blood pressure or an average blood pressure.

95. The method of any one of the clauses herein, wherein the determined physiological parameter includes bioimpedance.

96. The method of any one of the clauses herein, wherein the determined physiological parameter includes thoracic bioimpedance.

97. The method of any one of the clauses herein, wherein determining the physiological parameter includes determining the physiological parameter via at least one of the lead electrodes.

98. The method of any one of the clauses herein, further comprising, prior to generating the neuromodulation pulses, detecting, via at least one of the lead electrodes, a signal associated with a cardiac depolarization event.

99. The method of any one of the clauses herein, further comprising, prior to generating the neuromodulation pulses, receiving a signal associated with a cardiac depolarization event, wherein delivering the neuromodulation pulses is based in part on a predetermined delay after the signal associated with the cardiac depolarization event is received.

100. A method for configuring a treatment system to sense cardiac depolarization of a patient, the method comprising:

providing a treatment system including a neuromodulator and a signal delivery device electrically coupled to the neuromodulator, the neuromodulator including a base electrode and the signal delivery device including lead electrodes;

implanting the lead electrodes of the signal delivery device within a patient;

sensing, via a vector of the treatment system, a parameter associated with a cardiac depolarization event; and based on the sensed parameter, moving the signal delivery device such that the lead electrodes are proximate CSN afferent fibers of the patient.

101. The method of any one of the clauses herein, wherein the vector includes one of the lead electrodes and the base electrode.

102. The method of any one of the clauses herein, wherein the base electrode is a first base electrode and the neuromodulator further comprises a second base electrode, and a housing including the first base electrode and the second base electrode, wherein the vector includes the first base electrode and the second base electrode.

103. The method of any one of the clauses herein, wherein the neuromodulator comprises a housing including a conductive material, wherein a portion of the housing is the base electrode, and wherein the vector includes the base electrode and one of the lead electrodes.

104. The method of any one of the clauses herein, the method further comprising:

after moving the signal delivery device, generating, via the neuromodulator, neuromodulation pulses; and delivering the neuromodulation pulses to the CSN afferent fibers via one or more of the lead electrodes.

105. The method of any one of the clauses herein, the method further comprising:

after moving the signal delivery device, generating, via the neuromodulator, first neuromodulation pulses having first characteristics;

delivering the first neuromodulation pulses to the CSN afferent fibers via one or more of the lead electrodes;

obtaining a stimulation parameter of the first neuromodulation pulses, the stimulation parameter comprising at least one of amplitude, pulse width, or energy associated with the first neuromodulation pulses; and based on the obtained stimulation parameter, generating, via the neuromodulator, second neuromodulation pulses having second characteristics different than the first characteristics.

106. The method of any one of the clauses herein, wherein implanting the lead electrodes comprises implanting the lead electrodes at or near the patient's neck.

107. The method of any one of the clauses herein, wherein the treatment system comprises the treatment system of any one of the previous clauses.

108. The method of any one of the clauses herein, wherein the neuromodulation pulses are first neuromodulation pulses, the method further comprising delivering second neuromodulation pulses to another target tissue of a patient different than the CSN afferent fibers.

109. The method of any one of the clauses herein, wherein the neuromodulation pulses are first neuromodulation pulses, the method further comprising delivering second neuromodulation pulses to a hypoglossal nerve of the patient.

110. The method of any one of the clauses herein, wherein the neuromodulation pulses are first neuromodulation pulses, the method further comprising delivering second neuromodulation pulses to an ansa cervicalis nerve of the patient.

111. The method of any one of the clauses herein, wherein the neuromodulation pulses are first neuromodulation pulses, the method further comprising delivering second neuromodulation pulses to a left or right atria of the patient.

112. The method of any one of the clauses herein, wherein the neuromodulation pulses are first neuromodulation pulses, the method further comprising delivering second neuromodulation pulses to a left or right ventricle of the patient.

113. The method of any one of the clauses herein, wherein the neuromodulation pulses are first pulses, the method further comprising delivering second pulses to a diaphragm of the patient.

114. The method of any one of the clauses herein, further comprising:

detecting one or more cardiac depolarizations from an atria of the patient, and delivering electrical pulses to a ventricle of the patient based, at least in part, on the detected cardiac depolarizations.

115. A patient treatment system, comprising:

a neuromodulator comprising a housing, and at least one base electrode carried by the housing;

an implantable signal delivery device electrically coupleable to the neuromodulator, the signal delivery device comprising a lead body including a first region, a second region positionable over the first region, and lead electrodes electrically coupleable to the base electrode of the neuromodulator, wherein the lead electrodes are configured to be implanted proximate to and/or at least partially around one or more nerves associated with a baroreflex of a patient;

one or more processors; and tangible, non-transitory computer-readable media having instructions that, when executed by the one or more processors, cause the patient treatment system to perform operations comprising:

obtaining a physiological parameter of the patient, wherein the physiological parameter comprises at least one of blood pressure, heart rate, bioimpedance, or patient activity level;

based on the obtained physiological parameter, generating neuromodulation pulses; and delivering the neuromodulation pulses to the one or more nerves via one or more of the lead electrodes.

116. The patient treatment system of clause 115 or any other clause herein, wherein: the one or more nerves include carotid sinus nerve (CSN) afferent fibers of the patient, the lead electrodes include a first set of lead electrodes at the first region and a second set of lead electrodes at the second region, and the first set of electrodes are configured to be positioned over a first side of the CSN afferent fibers and the second set of electrodes are configured to be positioned over a second side of the CSN afferent fibers opposite the first side.

117. The patient treatment system of clause 115 or any other clause herein, wherein the lead electrodes include a first set of lead electrodes at the first region and a second set of lead electrodes at the second region, and wherein, when the first region is positioned over the second region, each one of the first set of lead electrodes is aligned with a corresponding one of the second set of lead electrodes.

118. The patient treatment system of clause 115 or any other clause herein, wherein:

the lead electrodes include a first set of lead electrodes at the first region and a second set of lead electrodes at the second region, the number of lead electrodes of the first set of lead electrodes is different than the number of lead electrodes of the second set of lead electrodes, and the first set of lead electrodes and the second set of lead electrodes span an identical distance of the lead body.

119. The patient treatment system of clause 115 or any other clause herein, wherein the lead electrodes include a first set of lead electrodes at the first region and a second set of lead electrodes at the second region, and wherein individual ones of the first set of lead electrodes has a first width and at least one of the second set of lead electrodes has a second width greater than the first width.

120. The patient treatment system of clause 115 or any other clause herein, wherein the one or more nerves include CSN afferent fibers of the patient, and wherein the lead electrodes include a first set of lead electrodes at the first region and a second set of lead electrodes at the second region, the operations further comprising identifying the CSN afferent fibers by obtaining impedance data from at least one of the first set of lead electrodes or at least one of the second set of lead electrodes, and wherein delivering the neuromodulation pulses comprises, based on the obtained impedance data, delivering the neuromodulation pulses via a first lead electrode of the first set of lead electrodes and a second lead electrode of the second set of lead electrodes.

121. The patient treatment system of clause 115 or any other clause herein, wherein each of the lead electrodes are individually addressable via the neuromodulator.

122. The patient treatment system of clause 115 or any other clause herein, wherein:

the signal delivery device includes conductors extending from the housing to the lead body, the at least one base electrode is a first base electrode, the neuromodulator includes a second base electrode spaced apart from the first base electrode, and each of the conductors are electrically coupled to (i) one of the first base electrode or the second base electrode, and (ii) one of the lead electrodes.

123. The patient treatment system of clause 115 or any other clause herein, wherein the obtained physiological parameter is indicative of cardiac muscle depolarization.

124. The patient treatment system of clause 115 or any other clause herein, wherein the obtained physiological parameter comprises heart rate, and wherein delivering the neuromodulation pulses comprises delivering the neuromodulation pulses at a stimulation rate that is correlated with the obtained physiological parameter, such that a higher value of the obtained physiological parameter corresponds to the higher value of the stimulation rate.

125. The patient treatment system of clause 115 or any other clause herein, wherein the obtained physiological parameter comprises a first heart rate and delivering the neuromodulation pulses comprises delivering first neuromodulation pulses at a first frequency, the operations further comprising:

determining a second heart rate; and based on the second heart rate, delivering second neuromodulation pulses at a second frequency higher than the first frequency.

126. The patient treatment system of clause 115 or any other clause herein, further comprising a blood pressure sensor operably coupled to the neuromodulator and configured to generate data comprising at least one of total blood pressure, diastolic blood pressure, or systolic blood pressure, wherein delivering the neuromodulation pulses is based at least in part on the generated data obtained from the blood pressure sensor.

127. The patient treatment system of clause 115 or any other clause herein, further comprising an acoustic sensor configured to detect cardiac depolarization, wherein generating the neuromodulation pulses is based at least in part on a signal from the acoustic sensor.

128. The patient treatment system of clause 115 or any other clause herein, further comprising an accelerometer configured to detect cardiac depolarization, wherein generating the neuromodulation pulses is based in part on a signal from the accelerometer.

129. The patient treatment system of clause 115 or any other clause herein, further comprising an accelerometer configured to output a signal indicative of an orientation of the patient, wherein generating the neuromodulation pulses is based in part on the signal from the accelerometer.

130. The patient treatment system of clause 115 or any other clause herein, wherein the neuromodulation pulses include a first pulse having a first delay from an immediately preceding pulse, a second pulse having a second delay from an immediately preceding pulse, and a third pulse having a third delay from an immediately preceding pulse, wherein the third delay is longer than the second delay and the second delay is longer than the first delay.

131. The patient treatment system of clause 115 or any other clause herein, wherein the neuromodulation pulses have two or more of:

a pulse width of 10-1000 microseconds, a duty cycle of no more than 50%, an amplitude of 0-10 mA, and a frequency of 0-1000 Hz.

132. The patient treatment system of clause 115 or any other clause herein, wherein the physiological parameter is a first physiological parameter and the neuromodulation pulses are first neuromodulation pulses, and wherein delivering the neuromodulation pulses comprises delivering first neuromodulation pulses to the one or more nerves according to the first stimulation parameters, the operations further comprising:

after delivering the first neuromodulation pulses, obtaining a second physiological parameter of the patient; and based on the second physiological parameter of the patient, generating second neuromodulation pulses having second stimulation parameters; and delivering the second neuromodulation pulses to the one or more nerves according to the second stimulation parameters, wherein the first stimulation parameters include a first frequency, a first amplitude, a first pulse width, and a first duty cycle, and the second stimulation parameters include a second frequency, a second amplitude, a second pulse width, and a second duty cycle, and wherein at least one of the first frequency, the first amplitude, the first pulse width, or the first duty cycle differ from a respective one of the second frequency, the second amplitude, the second pulse width, or the second duty cycle.

133. The patient treatment system of clause 115 or any other clause herein, wherein the physiological parameter is a first physiological parameter and the neuromodulation pulses are first neuromodulation pulses, and wherein delivering the neuromodulation pulses comprises delivering first neuromodulation pulses to the one or more nerves via a first group of the lead electrodes, the operations further comprising:

after delivering the first neuromodulation pulses, obtaining a second physiological parameter of the patient; and based on the second physiological parameter of the patient, generating second neuromodulation pulses; and delivering the second neuromodulation pulses to the one or more nerves via a second group of the lead electrodes different from the first group of the lead electrodes.

134. A method for configuring a treatment system to sense cardiac depolarization of a patient, the method comprising:

providing the treatment system including a neuromodulator and a signal delivery device electrically coupled to the neuromodulator, the neuromodulator including a base electrode and the signal delivery device including lead electrodes;

implanting the lead electrodes of the signal delivery device within the patient;

delivering first neuromodulation pulses to CSN afferent fibers of the patient via one or more of the lead electrodes, according to first stimulation parameters;

sensing, via a vector of the treatment system, a parameter associated with a cardiac depolarization event;

based on the sensed parameter, adjusting one or more of the first stimulation parameters to define second stimulation parameters; and delivering second neuromodulation pulses to the CSN afferent fibers of the patient via one or more of the lead electrodes according to the second stimulation parameters.

135. The method of clause 134 or any other clause herein, wherein the first stimulation parameters include a first frequency, a first amplitude, a first pulse width, and a first duty cycle, and the second stimulation parameters include a second frequency, a second amplitude, a second pulse width, and a second duty cycle, and wherein at least one of the first frequency, the first amplitude, the first pulse width, or the first duty cycle differ from a respective one of the second frequency, the second amplitude, the second pulse width, or the second duty cycle.

136. The method of clause 135 or any other clause herein, wherein delivering the first neuromodulation pulses comprises delivering the first neuromodulation pulses via a first group of the lead electrodes and delivering the second neuromodulation pulses comprises delivering the second neuromodulation pulses via a second group of the lead electrodes different from the first group of the lead electrodes.

137. The method of clause 134 or any other clause herein, wherein adjusting one or more of the first stimulation parameters comprises adjusting an electrode configuration for delivering neuromodulation pulses to the nerve fibers of the patient.

138. The method of clause 134 or any other clause herein, wherein the vector includes one of the lead electrodes and the base electrode.

139. The method of clause 134 or any other clause herein, wherein the base electrode is a first base electrode and the neuromodulator further comprises (i) a second base electrode, and (ii) a housing including the first base electrode and the second base electrode, wherein the vector includes the first base electrode and the second base electrode.

140. A patient treatment system, comprising:

a neuromodulator comprising a housing, and at least one base electrode carried by the housing;

an implantable signal delivery device electrically coupleable to the neuromodulator, the signal delivery device comprising:

a lead body including a first region, a second region, and an intermediate region between the first region and the second region, wherein the second region is positionable over the first region by folding the lead body along the intermediate region, and lead electrodes electrically coupleable to the base electrode of the neuromodulator, the lead electrodes including a first set of lead electrodes at the first region and a second set of lead electrodes at the second region, wherein:

the first set of lead electrodes and the second set of lead electrodes span an identical distance, the first set of lead electrodes and the second set of lead electrodes each includes at least three electrodes, and the lead electrodes are configured to be implanted proximate to and/or at least partially around CSN afferent fibers of a patient.

141. The patient treatment system of clause 140 or any other clause herein, wherein, when the first region is positioned over the second region, individual ones of the first set of lead electrodes at least partially overlap or are aligned with corresponding ones of the second set of lead electrodes along both a first dimension of the lead body and a second dimension of the lead body, the first dimension being normal to the second dimension.

142. The patient treatment system of clause 140 or any other clause herein, wherein, when the first region is positioned over the second region, individual ones of the first set of lead electrodes are (i) aligned with corresponding ones of the second set of lead electrodes along a first dimension of the lead body, and (ii) offset with the corresponding ones of the second set of lead electrodes along a second dimension of the lead body, the first dimension being normal to the second dimension.

143. The patient treatment system of clause 140 or any other clause herein, further comprising (i) first suture holes at the first region and laterally outward of the first set of the lead electrodes, and (ii) second suture holes at the second region and laterally outward of the second set of the lead electrodes.

144. The patient treatment system of clause 140 or any other clause herein, further comprising a first tapered tab extending laterally outward from a side portion of the first region away from the intermediate region and a second tapered tab extending laterally outward from the side portion of the second region.

We claim:

1. A patient treatment system, comprising:

a neuromodulator comprising a housing, and at least one base electrode carried by the housing;

an implantable signal delivery device electrically coupleable to the neuromodulator, the signal delivery device comprising a lead body including:

a first region including a first surface, a second region including a second surface, an intermediate region between the first region and the second region, wherein the signal delivery device includes (i) an open configuration in which the first surface is coplanar with the second surface and (ii) a closed configuration in which the second region is positioned over the first region and the first surface is parallel to the second surface, and wherein, in the closed configuration, the first surface is spaced apart from the second surface by a cross-sectional dimension of the intermediate region, and lead electrodes electrically coupleable to the base electrode of the neuromodulator, wherein the lead electrodes include a first set of lead electrodes on the first surface of the first region and a second set of lead electrodes on the second surface of the second region, wherein the first set of lead electrodes are spaced apart from one another along a central longitudinal axis and the second set of lead electrodes are spaced apart from one another along the central longitudinal axis, wherein the lead electrodes are configured to be implanted proximate to and/or at least partially around carotid sinus nerve (CSN) afferent fibers of a patient such that (i) the first set of lead electrodes are configured to be positioned over a first side of the CSN afferent fibers of the patient, and (ii) the second set of lead electrodes are configured to be positioned over a second side of the CSN afferent fibers opposite the first side, and wherein the central longitudinal axis extends through the first region, the intermediate region, and the second region;

one or more processors; and tangible, non-transitory computer-readable media having instructions that, when executed by the one or more processors, cause the patient treatment system to perform operations comprising:

obtaining a physiological parameter of the patient, wherein the physiological parameter comprises at least one of heart rate or patient activity level, wherein an increase in the heart rate or the patient activity level corresponds to an increased frequency of neuromodulation pulses;

based on the obtained physiological parameter, generating the neuromodulation pulses; and delivering the neuromodulation pulses to the CSN afferent fibers via one or more of the lead electrodes.

2. The patient treatment system of claim 1, wherein, when the first region is positioned over the second region, each one of the first set of lead electrodes is aligned with a corresponding one of the second set of lead electrodes.

3. The patient treatment system of claim 1, wherein a first number of lead electrodes of the first set of lead electrodes is different than a second number of lead electrodes of the second set of lead electrodes, and the first set of lead electrodes and the second set of lead electrodes span an identical distance of the lead body.

4. The patient treatment system of claim 1, wherein one of the first set of lead electrodes has a first width and at least one of the second set of lead electrodes has a second width greater than the first width.

5. The patient treatment system of claim 1, the operations further comprising identifying the CSN afferent fibers by obtaining impedance data from at least one of the first set of lead electrodes or at least one of the second set of lead electrodes, and wherein delivering the neuromodulation pulses comprises, based on the obtained impedance data, delivering the neuromodulation pulses via a first lead electrode of the first set of lead electrodes and a second lead electrode of the second set of lead electrodes.

6. The patient treatment system of claim 1, wherein each of the lead electrodes are individually addressable via the neuromodulator.

7. The patient treatment system of claim 1, wherein the signal delivery device includes conductors extending from the housing to the lead body, the at least one base electrode is a first base electrode, the neuromodulator includes a second base electrode spaced apart from the first base electrode, and each of the conductors are electrically coupled to (i) one of the first base electrode or the second base electrode, and (ii) one of the lead electrodes.

8. The patient treatment system of claim 1, wherein the obtained physiological parameter is indicative of cardiac muscle depolarization.

9. The patient treatment system of claim 1, wherein the obtained physiological parameter comprises the heart rate, and wherein delivering the neuromodulation pulses comprises delivering the neuromodulation pulses at a stimulation rate that is correlated with the obtained physiological parameter, such that a higher value of the obtained physiological parameter corresponds to the higher value of the stimulation rate.

10. The patient treatment system of claim 1, wherein the obtained physiological parameter comprises a first heart rate and delivering the neuromodulation pulses comprises delivering first neuromodulation pulses at a first frequency, the operations further comprising:

determining a second heart rate; and based on the second heart rate, delivering second neuromodulation pulses at a second frequency higher than the first frequency.

11. The patient treatment system of claim 1, further comprising a blood pressure sensor operably coupled to the neuromodulator and configured to generate data comprising at least one of total blood pressure, diastolic blood pressure, or systolic blood pressure, wherein delivering the neuromodulation pulses is based at least in part on the generated data obtained from the blood pressure sensor.

12. The patient treatment system of claim 1, further comprising an acoustic sensor configured to detect cardiac depolarization, wherein generating the neuromodulation pulses is based at least in part on a signal from the acoustic sensor.

13. The patient treatment system of claim 1, further comprising an accelerometer configured to detect cardiac depolarization, wherein generating the neuromodulation pulses is based in part on a signal from the accelerometer.

14. The patient treatment system of claim 1, further comprising an accelerometer configured to output a signal indicative of an orientation of the patient, wherein generating the neuromodulation pulses is based in part on the signal from the accelerometer.

15. The patient treatment system of claim 1, wherein the neuromodulation pulses include a first pulse having a first delay from an immediately preceding pulse, a second pulse having a second delay from the immediately preceding pulse, and a third pulse having a third delay from the immediately preceding pulse, wherein the third delay is longer than the second delay and the second delay is longer than the first delay.

16. The patient treatment system of claim 1, wherein the neuromodulation pulses have two or more of a pulse width of 10-1000 microseconds, a duty cycle of no more than 50%, an amplitude of 0-10 mA, and a frequency of 0-1000 Hz.

17. The patient treatment system of claim 1, wherein the physiological parameter is a first physiological parameter and the neuromodulation pulses are first neuromodulation pulses, and wherein the delivering the neuromodulation pulses comprises delivering the first neuromodulation pulses to the CSN afferent fibers according to first stimulation parameters, the operations further comprising:

after delivering the first neuromodulation pulses, obtaining a second physiological parameter of the patient;

based on the second physiological parameter of the patient, generating second neuromodulation pulses having second stimulation parameters; and delivering the second neuromodulation pulses to the CSN afferent fibers according to the second stimulation parameters, wherein the first stimulation parameters include a first frequency, a first amplitude, a first pulse width, and a first duty cycle, and the second stimulation parameters include a second frequency, a second amplitude, a second pulse width, and a second duty cycle, and wherein at least one of the first frequency, the first amplitude, the first pulse width, or the first duty cycle differ from a respective one of the second frequency, the second amplitude, the second pulse width, or the second duty cycle.

18. The patient treatment system of claim 1, wherein the physiological parameter is a first physiological parameter and the neuromodulation pulses are first neuromodulation pulses, and wherein delivering the neuromodulation pulses comprises delivering the first neuromodulation pulses to the CSN afferent fibers via a first group of the lead electrodes, the operations further comprising:

after delivering the first neuromodulation pulses, obtaining a second physiological parameter of the patient;

based on the second physiological parameter of the patient, generating second neuromodulation pulses; and delivering the second neuromodulation pulses to the CSN afferent fibers via the second group of the lead electrodes different from the first group of the lead electrodes.

19. The patient treatment system of claim 1, wherein:

the lead electrodes on the first region span a first cross-sectional dimension along an axis, the lead electrodes on the second region span a second cross-sectional dimension along the axis, the intermediate region spans a third cross-sectional dimension along the axis, and in the closed configuration, the first surface is spaced apart from the second surface by the third cross-sectional dimension.

20. The patient treatment system of claim 1, wherein, in the closed configuration, the first surface is spaced apart from the second surface by a third cross-sectional dimension across an entirety of the first region.

21. The patient treatment system of claim 1, further comprising: electrical contacts each electrically coupled to a corresponding one of the lead electrodes, wherein the electrical contacts are positioned on the first and second region such that a majority of a surface area of the first surface and the second surface is covered by the electrical contacts and the lead electrodes.

22. The patient treatment system of claim 1, wherein the first region, the intermediate region, and the second region comprise a single continuous layer such that the first set of lead electrodes and the second set of lead electrodes are coplanar in the open configuration.

23. A patient treatment system, comprising:

a neuromodulator comprising a housing, and at least one base electrode carried by the housing;

an implantable signal delivery device electrically coupleable to the neuromodulator, the signal delivery device comprising a lead body including:

a first region including a first surface, a second region including a second surface, an intermediate region between the first region and the second region, wherein the signal delivery device includes (i) an open configuration in which the first region is not positioned over the second region and (ii) a closed configuration in which the second region is positioned over the first region, wherein the first surface is congruent to the second surface, a first set of lead electrodes at the first surface of the first region and spanning a first cross-sectional dimension along an axis, and a second set of lead electrodes at the second surface of the second region and spanning a second cross-sectional dimension along the axis, wherein:

the first and second sets of lead electrodes are electrically coupleable to the base electrode of the neuromodulator, at least a portion of the first and second sets of lead electrodes are positioned along a central longitudinal axis extending through the first region, the intermediate region, and the second region, in the open configuration, the first surface is coplanar with the second surface and the intermediate region spans a third cross-sectional dimension along the axis, in the closed configuration, the second region is positioned over the first region, the first surface is parallel to the second surface, and the first surface is spaced apart from the second surface by the third cross-sectional dimension, and the signal delivery device is configured to be implanted proximate to and/or at least partially around carotid sinus nerve (CSN) afferent fibers of a patient such that (i) the first set of lead electrodes are configured to be positioned over a first side of the CSN afferent fibers of the patient, and (ii) the second set of lead electrodes are configured to be positioned over a first side of the CSN afferent fibers of the patient, and (ii) the second set of lead electrodes are configured to be positioned over a second side of the CSN afferent fibers opposite the first side;

one or more processors; and tangible, non-transitory computer-readable media having instructions that, when executed by the one or more processors, cause the patient treatment system to perform operations comprising:

obtaining a physiological parameter of the patient, wherein the physiological parameter comprises at least one of heart rate or patient activity level;

based on the obtained physiological parameter, generating neuromodulation pulses, wherein an increase in the heart rate or the patient activity level corresponds to an increased frequency of the neuromodulation pulses; and delivering the neuromodulation pulses to the CSN afferent fibers via one or more of the first and second sets of lead electrodes.

24. The patient treatment system of claim 23, wherein the first set of lead electrodes includes at least five electrodes and the second set of lead electrodes includes at least five electrodes.

25. The patient treatment system of claim 24, wherein the first set of lead electrodes includes non-peripheral electrodes and peripheral electrodes laterally outward of the non-peripheral electrodes, and wherein the peripheral electrodes have a different polarity than the non-peripheral electrodes.

26. The patient treatment system of claim 23, wherein the first set of lead electrodes includes a first amount of electrodes and the second set of lead electrodes includes a second amount of electrodes different than the first amount, and wherein the first set of lead electrodes and the second set of lead electrodes span an identical width.

27. The patient treatment system of claim 23, further comprising (i) first suture holes at the first region that are laterally outward of the first set of lead electrodes, and (ii) second suture holes at the second region that are laterally outward of the second set of lead electrodes.

28. The patient treatment system of claim 23, wherein the base electrode is a first base electrode and the neuromodulator further comprises (i) a second base electrode within the housing, and wherein the operations further comprise sensing, via a vector including the first base electrode and the second base electrode, a signal associated with a cardiac depolarization event.

29. The patient treatment system of claim 23, wherein the operations further comprise sensing, via a vector including the base electrode and one of the first set of lead electrodes, a signal associated with a cardiac depolarization event.

30. The patient treatment system of claim 23, further comprising:

a first electrical contact on the first region and electrically coupled to one of the first set of lead electrodes; and a second electrical contact on the second region and electrically coupled to one of the second set of lead electrodes.

31. The patient treatment system of claim 30, wherein the first electrical contact is positioned closer to the intermediate region than the first set of lead electrodes and/or the second electrical contact is positioned closer to the intermediate region than the second set of lead electrodes.

32. The patient treatment system of claim 23, further comprising:

a first tapered tab extending laterally outward from a first side portion of the first region away from the intermediate region; and a second tapered tab extending laterally outward from a second side portion of the second region away from the intermediate region.

33. The patient treatment system of claim 23, wherein generating the neuromodulation pulses comprises generating the neuromodulation pulses such that a number of the neuromodulation pulses generated per cardiac cycle is approximately consistent.

34. The patient treatment system of claim 23, wherein the frequency of the neuromodulation pulses is inversely correlated to an R-R interval time of the patient.

* * * * *